(12) United States Patent
Forbes

(10) Patent No.: US 10,335,397 B2
(45) Date of Patent: *Jul. 2, 2019

(54) METHODS OF TREATING HEPATIC ENCEPHALOPATHY

(71) Applicant: Salix Pharmaceuticals, Ltd, Bridgewater, NJ (US)

(72) Inventor: William Forbes, Raleigh, NC (US)

(73) Assignee: Salix Pharmaceuticals, Ltd, Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/922,010

(22) Filed: Mar. 15, 2018

(65) Prior Publication Data

US 2018/0303804 A1 Oct. 25, 2018

Related U.S. Application Data

(63) Continuation of application No. 15/460,704, filed on Mar. 16, 2017, now Pat. No. 9,949,958, which is a continuation of application No. 14/612,697, filed on Feb. 3, 2015, now Pat. No. 9,629,829, which is a continuation of application No. 13/768,617, filed on Feb. 15, 2013, now Pat. No. 8,969,398, which is a continuation of application No. 13/077,373, filed on Mar. 31, 2011, now abandoned, which is a continuation of application No. PCT/US2009/059321, filed on Oct. 2, 2009.

(60) Provisional application No. 61/102,349, filed on Oct. 2, 2008.

(51) Int. Cl.

| | |
|---|---|
| *A61K 31/437* | (2006.01) |
| *A61K 31/08* | (2006.01) |
| *A61K 31/352* | (2006.01) |
| *A61K 31/395* | (2006.01) |
| *A61K 31/4164* | (2006.01) |
| *A61K 31/426* | (2006.01) |
| *A61K 31/4439* | (2006.01) |
| *A61K 31/606* | (2006.01) |
| *A61K 31/7016* | (2006.01) |
| *A61K 31/785* | (2006.01) |
| *A61K 38/14* | (2006.01) |
| *A61K 38/31* | (2006.01) |
| *A61K 45/06* | (2006.01) |

(52) U.S. Cl.
CPC ............ *A61K 31/437* (2013.01); *A61K 31/08* (2013.01); *A61K 31/352* (2013.01); *A61K 31/395* (2013.01); *A61K 31/4164* (2013.01); *A61K 31/426* (2013.01); *A61K 31/4439* (2013.01); *A61K 31/606* (2013.01); *A61K 31/7016* (2013.01); *A61K 31/785* (2013.01); *A61K 38/14* (2013.01); *A61K 38/31* (2013.01); *A61K 45/06* (2013.01)

(58) Field of Classification Search
CPC .................................................. A61K 31/437
See application file for complete search history.

(56) References Cited

U.S. PATENT DOCUMENTS

| | | | |
|---|---|---|---|
| 4,343,785 A | 8/1982 | Schmolka | |
| 4,557,866 A | 12/1985 | Cannata et al. | |
| 6,562,629 B1 | 5/2003 | Lin et al. | |
| 7,928,115 B2 | 4/2011 | Forbes et al. | |
| 8,642,573 B2 * | 2/2014 | Forbes | A61K 31/437 514/53 |
| 8,829,017 B2 * | 9/2014 | Forbes | A61K 31/437 514/279 |
| 8,946,252 B2 * | 2/2015 | Forbes | A61K 31/437 514/279 |
| 8,969,398 B2 * | 3/2015 | Forbes | A61K 31/08 514/397 |
| 9,421,195 B2 * | 8/2016 | Forbes | A61K 31/437 |
| 9,629,828 B2 * | 4/2017 | Forbes | A61K 31/437 |
| 9,629,829 B2 * | 4/2017 | Forbes | A61K 31/08 |
| 9,855,254 B2 * | 1/2018 | Forbes | A61K 31/437 |
| 9,949,958 B2 * | 4/2018 | Forbes | A61K 31/08 |
| 2002/0028764 A1 | 3/2002 | Grofte et al. | |
| 2004/0106590 A1 | 6/2004 | Eisenstein | |
| 2004/0157840 A1 | 8/2004 | Cabana et al. | |
| 2004/0229948 A1 | 11/2004 | Summar et al. | |
| 2005/0142099 A1 | 6/2005 | Halow | |
| 2005/0272754 A1 | 12/2005 | Viscomi et al. | |
| 2006/0210592 A1 | 9/2006 | Kodsi | |
| 2008/0119554 A1 | 5/2008 | Jalan et al. | |
| 2008/0132530 A1 | 6/2008 | Viscomi et al. | |
| 2008/0262012 A1 | 10/2008 | Viscomi et al. | |
| 2009/0028940 A1 | 1/2009 | Jahagirdar et al. | |
| 2009/0088423 A1 | 4/2009 | Sayada | |
| 2009/0130201 A1 | 5/2009 | Viscomi et al. | |

(Continued)

FOREIGN PATENT DOCUMENTS

| | | |
|---|---|---|
| EP | 0616808 A1 | 9/1994 |
| EP | 0858804 A1 | 8/1998 |

(Continued)

OTHER PUBLICATIONS

U.S. Appl. No. 15/824,209, filed Nov. 2017, Forbes; William.*

(Continued)

*Primary Examiner* — Svetlana M Ivanova

(74) *Attorney, Agent, or Firm* — McCarter & English, LLP; Jonathan M. Sparks; Michael J. DeGrazia

(57) ABSTRACT

The application describes treatment of hepatic encephalopathy using gastrointestinal specific antibiotics. One example of a gastrointestinal specific antibiotic is rifaximin.

13 Claims, 13 Drawing Sheets

(56) References Cited

U.S. PATENT DOCUMENTS

| | | |
|---|---|---|
| 2009/0149453 A1 | 6/2009 | Sayada |
| 2010/0069421 A1 | 3/2010 | Bettenhausen |
| 2010/0136125 A1 | 6/2010 | Jacobus et al. |
| 2010/0174064 A1 | 7/2010 | Gushurst et al. |
| 2010/0204173 A1 | 8/2010 | Forbes |
| 2010/0239664 A1 | 9/2010 | Gushurst et al. |
| 2010/0317681 A1 | 12/2010 | Forbes |
| 2011/0035232 A1 | 2/2011 | Forbes et al. |
| 2011/0071103 A1 | 3/2011 | Forbes et al. |
| 2011/0243879 A1 | 10/2011 | Forbes |

FOREIGN PATENT DOCUMENTS

| | | | |
|---|---|---|---|
| EP | 2011486 A1 | 1/2009 | |
| MX | 2010/009197 A | 11/2010 | |
| WO | 03047577 A2 | 6/2003 | |
| WO | 2007/103448 A2 | 9/2007 | |
| WO | 2008/016708 A2 | 2/2008 | |
| WO | 2008/035109 A1 | 3/2008 | |
| WO | 2009/108730 A2 | 9/2009 | |
| WO | 2009108814 A1 | 9/2009 | |
| WO | 2010040020 A1 | 4/2010 | |
| WO | 2011/005388 A1 | 1/2011 | |

OTHER PUBLICATIONS

Scarpignato, C. and Pelosini, I. (2006) Digestion 73:13-27 (EPUB: Feb. 8, 2006).
Tavares de Melo et al. (2008) Am. J. Health-Syst. Pharm. 65:818-822.
Williams, R. et al. (2000) Eur. J. Gastroenterol. Hepatol. 12:203-208.
Zeneroli, M. L. et al. (1997) Pharma. Res. 35:557-560.
Zeneroli, M. L. et al. (2005) Chemotherapy 51 (supp):90-95.
Adachi et al. Reviews of Anti-Infective Agents 42: 541-547 (2006).
Bass (2005) Hepatology AASLD Abstract No. 533.
Bass, NM (2006) Aliment Pharmacol. Ther 25(Suppl. 1):23-31.
Colecchia et al., "Efficacy of long term cyclic administration of the poorly absorbed antibiotic Rifaximin in symptomatic, uncomplicated colonic diverticular disease," World J Gastroenterol 13:264-269 (Jan. 2007).
De Marco et al. (1984) Curr. Ther. Res. 36:668674.
Di Piazza et al. (1991) 23:403-407.
Festi et al. (1993) Curr. Ther. Res. 54:598-609.
Festi, D. et al. (2006) Digestion 73(suppl 1):94-101.
Giacomo et al. (1993) Eur. J. Clin. Res. 4:57-66.
Gillis, J.C. and Brogden, R. N. (1995) Drugs 49:467-484.
Jiang et al. European Journal of Gastroenterology & Hepatology 20:1064-1070 (2008).
Kirchels et al., "Critical flicker frequency for quantification of low grade hepatic encephalopathy," Hepatology 35 (2): 357-366 (Feb. 2002)—Abstract only.
Lawrence et al. (2008) Pharmacotherapy 28:1019-1032.
Leevy et al. Hospitalizations During the Use of Rifaximin Versus Lactulose for the Treatment of Hepatic Encephalopathy, Dig. Dis. Sci. (Jan. 24, 2007) 52:737-741.
Lewis & Howdle, "The neurology of liver failure," Q J Med 96:623-633 (2003).
Maclayton, D. O. et al. (2009) Ann. Pharmacother. 43: 77-84) (EPUB:Dec. 17, 2008).
Massa et al. (1993) Eur. J. Clin. Res. 4:7-18.
NCT00298038, A Multi Center, Randomized, Double-Blind, Placebo-Controlled Trial to Evaluate the Efficacy, Safety and Tolerability of Rifaximin 550 Mg BID for 6 Months in Preventing Hepatic Encephalopathy, updated on Feb. 28, 2006.
Neff et al. (2006) Transplantation Proceedings 38:3552-3555.
Ojetti et al. (2009) Expert Opin. Drug Metab. Toxicol. 5: 675-682.
Pedretti et al. (1991) Ital. J. Gastroenterol. 23:175-78.
Pharmacology/Toxicology Review of Rifaximin by the FDA, Apr. 26, 2004.
Prescribing Information for Rifaximin, Argentina, Date Unknown, but after Apr. 23, 1985.
Prescribing Information for Rifaximin, Austria Nov. 2005.
Prescribing Information for Rifaximin, Bulgaria, Jun. 2007.
Prescribing Information for Rifaximin, China, Oct. 2006.
Prescribing Information for Rifaximin, Czech Republic Mar. 2008.
Prescribing Information for Rifaximin, Greece 2001.
Prescribing Information for Rifaximin, Hungary Apr. 2004.
Prescribing Information for Rifaximin, Italy, Apr. 23, 1985.
Prescribing Information for Rifaximin, Korea, Jan. 2006.
Prescribing Information for Rifaximin, Lebanon, Dec. 2002.
Prescribing Information for Rifaximin, Mexico Jul. 2007.
Prescribing Information for Rifaximin, Poland Apr. 2006.
Prescribing Information for Rifaximin, Portugal Date Unknown, but after Apr. 23, 1985.
Prescribing Information for Rifaximin, Romania, Nov. 2005.
Prescribing Information for Rifaximin, Russia, Date Unknown, but after Apr. 23, 1985.
Prescribing Information for Rifaximin, Slovakia Sep. 2003.
Prescribing Information for Rifaximin, Spain, Date Unknown, but after Apr. 23, 1985.
Prescribing Information for Rifaximin, Tunesia, Mar. 2004.
Prescribing Information for Rifaximin, Turkey Sep. 2007.
Prescribing Information for Rifaximin, United States, Mar. 2010.
Prescribing Information for Rifaximin, Venezeula Sep. 2008.
Rifaximin Tablet Label, Jul. 2006.
Riggio et al (World J Gastrointest Pharmacol Ther 1:54-63, 2010).
Riggio, O. et al. (2005) J. Hepatol. 42:6740679.
Salix Pharmaceutical's Press Release (available online at www.redOorbit.com, Jan. 11, 2006).
Sama, C. et al. (2004) Curr. Ther. Res. 5:413-422.
Scarpignato, C. and Pelosini, I. (2005) Chemotherapy 51(Supp):36-66.
Loguercio et al., Cyclic treatment of chronic hepatic encephalopathy with rifaximin. Results of a double-blind clinical study. Minerva Gastroenterol. Dietol., Mar. 2003; 49(1): 53-62 (Abstract only) ("Loguercio").
Salix Pharmaceuticals Development Update; XIFAXAN® Trials Initiated in C. Difficile-Associated Diarrhea, Irritable Bowel Syndrome and Hepatic Encephalopathy, posted on Jan. 11, 2006, Business Wire ("Xifaxan").
Puxeddu et al., Rifaximin in the treatment of chronic hepatic encephalopathy, Current Medical Research and Opinion, vol. 13, No. 5, pp. 274-281,1995.
Mas et al., Comparison of rifaximin and lactitol in the treatment of acute hepatic encephalopathy: results of a randomized, double-blind, double-dummy, controlled clinical trial, Journal of Hepatology 38 (2003) 51-58.
Yong-Han et al., Comparison of rifaximin and lactitol in the treatment of acute hepatic encephalopathy: a prospective randomized study. Yonsei Medical Journal, vol. 46, No.3, pp. 399-407, 2005 ("Yong-Han"; of record).
Paik et al. Comparison of rifaximin and lactulose for the treatment of hepatic encephalopathy: a prospective randomized study. Jun. 2005 Yonsei Medical Journal, vol. 46, N 3, p. 399-407; abstract; table 3-4, figure 1, p. 399, col. 2, para 2; p. 402; col. 1, para 1, col. 2, para 4; p. 403, col. 1, para 1.
Romero-Gomez. Critical flicker frequency: It is time to break down barriers surrounding minimal hepatic encephalopathy; Journal fo Hepatology 47 2007, p. 10-11. p. 10, col. 2, para 1; p. 11, col. 1, para 1.
Saab et al. MELD Fails to Measure Quality of Life in Liver Transplant Candidates. Liver Transplantation, 2005, vol. 11, No. 2; pp. 218-223; p. 218, col. 2, para 3; p. 219, col. 1, para 5-7, col. 2, para 3.
Bajaj et al. Minimal hepatic encephalopathy matters in daily life. World J Gastroenterol. Jun. 21, 2008, 14(23): 3609-3615; p. 3610, col. 2, para 2.
Ma et al. Rifaximin is a Gut-Specific Human Pregnane X Receptor Activator. The Journal of Pharmacology and Experimental Therapeutics. 2007 vol. 322, No. 1. abstract; p. 396, col. 2, para 3.
Baker Current FDA-related drug information; Hospital Pharmacy 2003 vol. 38, No. 6, pp. 582-597; table 3.

(56) References Cited

OTHER PUBLICATIONS

Xifaxan Prescribing Information datasheet. Mar. 2008. retrieved from internet at <http://www.salix.com/assets/pdf/prescribe_info/xifaxanpi.pdf>. p. 1, col. 1, para 7.

Gintant et al. Utility of hERG Assays as Surrogate Markers of Delayed Cardiac Repolarization and QT Safety. Toxicologic Pathology, 2006, 34:81-90; abstract.

Yoo et al (Am J Gastroenterol 98: 1395-1399, 2003—Abstract only).

Taylor, et al. "Systemic Pharmacokinetics of Rifaximin in Volunteers with Shigellosis", Mar. 2008(Mar. 2008), Antimicrobial Agents and Chemotherapy, vol. 52, No. 3; p. 1179-1181; Table 1; pp. 1179, col. 1, Para. 1, col. 2, Para 4; p. 1180, col. 1, Para. 1; p. 1181, col. 1, Para 1-2.

Gionchetti et al., "Antibiotic Treatment in Inflammatory Bowel Disease: Rifaximin a New Possible Approach", European Review for Medical and Pharmacological Sciences; 1999, vol. 3; p. 27-30; p. 29, col. 1, Para. 1.

Vignali et al., "Tips with Expanded Polytetrafluoroethylene Overed Stent", Results of an Italian Multicenter Study; Aug. 2005 (Aug. 2005) American Roentgen Ray Society, 185:472?480; Table 1, Figure 5, Abstract; p. 474, col. 1, Para 2; p. 478, col. 3, Para 1.

Chari et al., "Treatment of Hepatic Failure with ex Vivo Pig-Liver Perfusion Followed by Liver Transplantation", Jul. 28, 1994 (Jul. 28, 1994) The New England Journal of Medicine, vol. 331, No. 4; p. 235, col. 1, Para 1, col. 2, Para 1; p. 236, col. 2, Para 1.

International Search Report, International Patent Application No. PCT/US2010/038742, dated: Dec. 29, 2011 (Dec. 29, 2011).

Gerard et al. Expert Reviews of Anti Infective Therapeutics 3(2):201-211 (2005).

Prescribing Information for Rifaximin, United States, May 2004.

Prescribing Information for Rifaximin, United States, Jan. 2007.

Package Insert for the commercial product Xifaxan tablets from Physicians Desk Reference (PDR), (retrieved Jan. 2010), http://www.pdrel.com/View/Common/PrintReady.

Sharma et al., Critical flicker frequency: Diagnostic tool for minimal hepatic encephalopathy, Journal of Hepatology 47 (2007) 67-63.

Romero-Gomez et al., Value of the critical flicker frequency in patients with minimal hepatic encephalopathy, Hepatology, Apr. 2007, 879-885.

Miglio et al., Rifaximin, a non-absorbable rifamycin, for the treatment of hepatic encephalopathy. A double-blind, randomized trial, Curr Med Res Op 13:593-601, 1997 (Abstract Only).

Bustamante et al (J Hepatol 30:890-895, 1999).

Bass N. et al: "93 Rifaximin is Effective in Maintaining Remission in Hepatic Encephalopathy: Results of a Large, Randomized, Placebo-Controlled Trial", Journal of Hepatology, Munksgaard International Publishers, Copenhagen, DK, vol. 50, Apr. 1, 2009, p. S39.

Ninni A.: "Il trattamento con rifamicina SV negli epatopazienti non peggiora lo stato di sofferenza preesistente e fa rilevare concentrazioni ematiche piu elevate" Chemotherapy, Jan. 1, 1963, pp. 567-568. Abstract.

Baker, Daniel E., et al., New Drugs Approved by the FDA; New Dosage Forms and Indications; Agents Pending FDA Approval; Significant Labeling Changes Related to Safety; Hospital Pharmacy, 2003, vol. 38, No. 12, pp. 1163-1174; table 3.

Bass, et al., "Emerging Therapies for the Management of Hepatic Encephalopathy," Seminars in Liver Disease, Thieme Medical Publishers, US, vol. 27, No. Suppl. 2, Aug. 1, 2007, pp. 18-25.

Zhao Liyun, "Clinical Study on New Medicine Rifaximin," Hainan Medical Journal, 2005, vol. 16, No. 5.

Liu Houyu et al., "Hepatic encephalopathy (II)," Chinese Journal of Gastroenterology, 2003, vol. 8, No. 1.

Hiroshi Ishii and 3 others, D-009, "A Case of Refractory Hepatic Encephalopathy Successfully Treated with Vancomycin Hydrochloride," Proceedings of the Symposium of the Japanese Society of Social Insurance Medicine, Oct. 1999, 37th., p. 106.

Rifaximin Demonstrates Highly Statistically Significant Results in Prevention of Hepatic Encephalopathy in Pivotal Phase 3 Study, published on Oct. 6, 2008 on website http://www.salix.com/news-media/news/previous-years-news/rifaximin-demonstrates-highly-statistically-significant-results-in-prevention-of-hepatic-encephalopathy-in-pivotal-phase-3-study.aspx.

Jiang, et al., "Rifaximin: In vitro and in vivo Antibacterial Activity—A Review," Chemotherapy, 51(suppl 1):67-72, 2005.

Jane E. Henney, a report from the Commissioner of the United States Food and Drug Administration, Department of Health and Human Services, "Issues Related to Antimicrobial Resistance," Sep. 20, 2000.

Dupont et al., Influence of rifaximin treatment on the susceptibility of intestinal Gram-negative flora and enterococci. Clin Microbiol Infect. 10(11):1009-11 (2004).

Hufnagel et al., A putative sugar-binding transcriptional regulator in a novel gene locus in Enterococcus faecalis contributes to production of biofilm and prolonged bacteremia in mice. J Infect Dis. 189(3):420-30 (2004).

Copending U.S. Appl. No. 15/824,209, filed Nov. 28, 2017.

Bolukbas et al., Child-Pugh classification dependent alterations in serum leptin levels among cirrhotic patients: a case controlled study. BMC Gastroenterol. Sep. 23, 2004;4:23. 6 pages.

Dupont et al., Treatment of travelers' diarrhea: randomized trial comparing rifaximin, rifaximin plus loperamide, and loperamide alone. Clin Gastroenterol Hepatol. Apr. 2007;5(4):451-6.

Garey et al., Rifamycin antibiotics for treatment of Clostridium difficile-associated diarrhea. Ann Pharmacother. Jun. 2008;42(6):827-35.

GenBank Accession No. AC025038, Homo sapiens chromosome 10 clone RP11-443O13, complete sequence. 68 pages, Apr. 9, 2002.

GenBank Accession No. BAB47425, KIAA1796 protein, partial [Homo sapiens]. 2 pages, Jul. 21, 2016.

GenBank Accession No. NM_001143774, Homo sapiens phytanoyl-CoA 2-hydroxylase interacting protein like (PHYHIPL), transcript variant 2, mRNA. 6 pages, Jun. 24, 2018.

GenBank Accession No. NM_032439, Homo sapiens phytanoyl-CoA 2-hydroxylase interacting protein like (PHYHIPL), transcript variant 1, mRNA. 6 pages, Jun. 23, 2018.

GenBank Accession No. NP_001137246, phytanoyl-CoA hydroxylase-interacting protein-like isoform 2 [Homo sapiens]. 4 pages, Jun. 24, 2018.

GenBank Accession No. NP_115815, phytanoyl-CoA hydroxylase-interacting protein-like isoform 1 [Homo sapiens]. 4 pages, Jun. 23, 2018.

GenBank Accession No. NT_030059, Homo sapiens chromosome 10 genomic scaffold, GRCh38.p12 Primary Assembly HSCHR10_CTG5. 18 pages, Mar. 26, 2018.

GenBank Accession No. Q96FC7, RecName: Full=Phytanoyl-CoA hydroxylase-interacting protein-like. 10 pages, Sep. 12, 2018.

Gomi et al., In vitro antimicrobial susceptibility testing of bacterial enteropathogens causing traveler's diarrhea in four geographic regions. Antimicrob Agents Chemother. Jan. 2001;45(1):212-6.

Halsey, Current and future treatment modalities for Clostridium difficile-associated disease. Am J Health Syst Pharm. Apr. 15, 2008;65(8):705-15.

Hartley et al., DNA cloning using in vitro site-specific recombination. Genome Res. Nov. 2000;10(11):1788-95.

Nagase et al., Prediction of the coding sequences of unidentified human genes. XX. The complete sequences of 100 new cDNA clones from brain which code for large proteins in vitro. DNA Res. Apr. 27, 2001;8(2):85-95.

Ruiz et al., In vitro antimicrobial activity of rifaximin against enteropathogens causing traveler's diarrhea. Diagn Microbiol Infect Dis. Dec. 2007;59(4):473-5.

Simpson et al., Systematic subcellular localization of novel proteins identified by large-scale cDNA sequencing. EMBO Rep. Sep. 2000;1(3):287-92.

Taylor et al., A randomized, double-blind, multicenter study of rifaximin compared with placebo and with ciprofloxacin in the treatment of travelers' diarrhea. Am J Trop Med Hyg. Jun. 2006;74(6):1060-6.

Vilstrup et al., Hepatic Encephalopathy in Chronic Liver Disease: 2014 Practice Guideline by AASLD and EASL. The American Association for Study of Liver Diseases. 74 pages, (2014).

(56) References Cited

OTHER PUBLICATIONS

Wiemann et al., Toward a catalog of human genes and proteins: sequencing and analysis of 500 novel complete protein coding human cDNAs. Genome Res. Mar. 2001;11(3):422-35.
Wolf, Encephalopathy, Hepatic. Emedicine. Retrieved online at: http://basic.shsmu.edu.cn/jpkc/pathology/6/gxnb/htm. 7 pages. May 20, 2014.

\* cited by examiner

METHODS OF TREATING HEPATIC ENCEPHALOPATHY

RELATED APPLICATIONS

This application is a continuation of U.S. application Ser. No. 15/460,704, filed Mar. 16, 2017, which is a continuation of U.S. application Ser. No. 14/612,697, filed Feb. 3, 2015, which is a continuation of U.S. application Ser. No. 13/768, 617, filed Feb. 15, 2013, which is a continuation of U.S. application Ser. No. 13/077,373, filed Mar. 31, 2011, which claims benefit of International Patent Application PCT/US2009/059321, filed Oct. 2, 2009, which claims benefit of U.S. Provisional Application No. 61/102,349, filed Oct. 2, 2008. The entire contents of each of the aforementioned applications are hereby expressly incorporated herein by reference.

BACKGROUND

Hepatic encephalopathy (HE) is caused by a reversible decrease in neurologic function associated with liver failure and portosystemic venous shunting. HE occurs in 1 of every 3 cases of cirrhosis, in cases of fulminant hepatic failure reported in the United States (US), and is present in nearly half of patients reaching end-stage liver disease. It may occur at any age, but the peaks parallel those of fulminant liver disease (peak=40's), and cirrhosis (peak=late 50's).

The incidence of HE is likely to increase with the incidence of hepatitis C in the general population and cirrhotics in aging patients. Acute HE signifies a serious prognosis with a 40% likelihood of survival for 1 year. There is a need in the art for a compositions and methods for treating and preventing HE.

SUMMARY

Provided herein are compositions and methods for the prevention and treatment of hepatic encephalopathy.

One embodiment is a method of treating or preventing hepatic encephalopathy (HE) in a subject comprising administering to a subject a gastrointestinal (GI) specific antibiotic. In one embodiment the GI specific antibiotic is rifaximin. In another embodiment, the rifaximin is 1100 mg/day of rifaximin.

Another embodiment is a method of decreasing a subject's risk of a hepatic encephalopathy HE breakthrough episode by administering a GI specific antibiotic to a subject suffering from HE.

Yet another embodiment is a method of maintaining remission of hepatic encephalopathy in a subject by administering a GI specific antibiotic to a subject suffering from HE.

Still another embodiment is a method of reducing the frequency of hospitalization visits by an HE patient, comprising administering a GI specific antibiotic to a subject suffering from HE.

DETAILED DESCRIPTION

Figure 1:
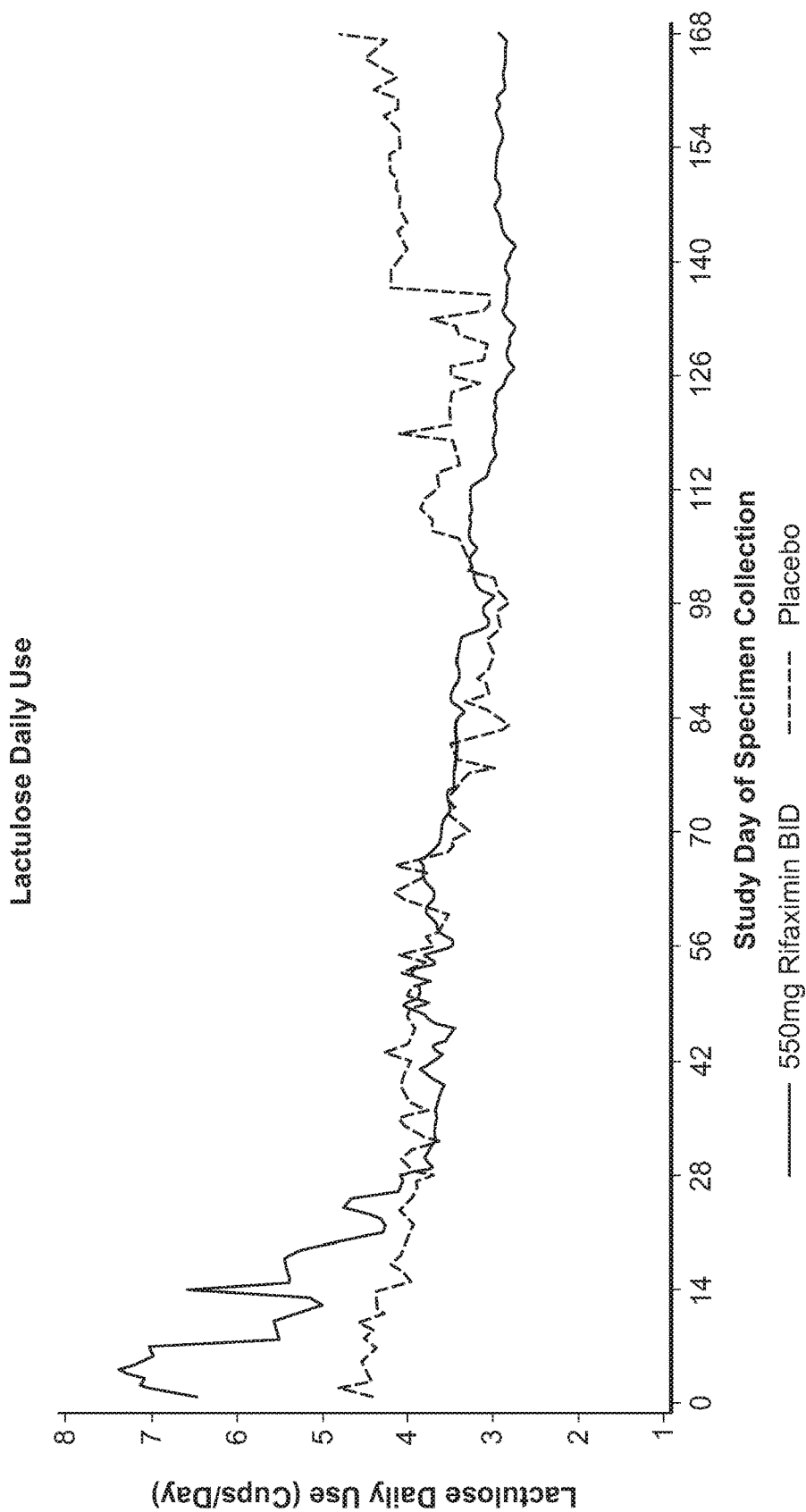
FIG. 1 is a line graph comparing lactulose daily use between subjects taking placebos and subjects taking rifaximin.

The main pathogenesis of HE is related to nitrogenous substances derived from the gut adversely affecting brain function. The most influential of these compounds is thought to be ammonia, a byproduct of protein digestion that is normally detoxified by the liver. Correlation of blood levels with mental state in cirrhosis, however, is inaccurate, in part, because the blood-brain barrier permeability to ammonia is increased in patients with HE. Other gut-derived toxins have also been proposed as being responsible for HE.

In patients with chronic liver disease, the occurrence of hepatic encephalopathy is associated with a low quality of life compared to age-matched patients without HE. Overt HE episodes are debilitating, can present without warning, render the patient incapable of self-care, and frequently result in hospitalization. Patients with HE experience symptoms including fatigue, daytime sleepiness, and lack of awareness (Conn score 1); and confusion and disorientation (Conn score 2) that significantly interfere with day-to-day function and decreased ability for self care. Often, this lack of self care leads to improper nutrition and non-adherence to therapy and further escalates into more severe symptoms such as increased somnolence, gross disorientation and stupor (Conn score 3) or coma (Conn score 4).

A history of overt HE episodes and the severity of HE episodes were also found to be predictive of decreased survival in patients with chronic liver disease. In patients with liver cirrhosis and a history of overt HE episodes, survival probability was 42% at 1 year and 23% at 3 years after experiencing an HE episode. In another analysis, the occurrence of an HE episode of Conn score 2 in patients with cirrhosis was associated with a 4-fold increase in the risk of death.

These toxic compounds gain access to the systemic circulation as a result of decreased hepatic function or portal-systemic shunts. Once in brain tissue, the compounds produce alterations of neurotransmission that affect consciousness and behavior. HE is attributed to global central nervous system depression from nitrogenous compounds that result in excitation of gamma-aminobutyric acid (GABA) and decreased neurotransmission of glutamate.

Precipitating factors include azotemia (29%), sedatives, tranquilizers, analgesics (24%), gastrointestinal bleeding (18%), excess dietary protein (9%), metabolic alkalosis (11%), infection (3%), constipation (3%). Surgery, particularly transjugular intrahepatic portal-systemic shunt (TIPS) procedures, also may precipitate HE. HE due to unknown causes accounts for only 2% of cases.

Initial manifestations are subclinical and require psychometric testing for diagnosis. There are 4 progressive stages of impairment known as the West Haven criteria (or Conn score) which range from Stage 0 (Lack of detectable changes in personality) to Stage 4 (Coma, decerebrate posturing, dilated pupils) as discussed in more detail below.

HE is manifested as a continuum of psychomotor dysfunction, impaired memory, increased reaction time, sensory abnormalities, poor concentration and in severe forms, as coma. Changes may be observed in personality, consciousness, behavior and neuromuscular function. Neurologic signs may include hyperreflexia, rigidity, myoclonus and asterixis (coarse "flapping" muscle tremor). Cognitive tasks such as connecting numbers with lines can be abnormal. Fetor hepaticus (sweet breath odor) may be present. Electroencephalogram (EEG) tracings show nonspecific slow, triphasic wave activity mainly over the frontal areas. Prothrombin time may be prolonged and not correctable with Vitamin K. A computed tomography scan of the head may be normal or show general atrophy. Finally, signs of liver disease such as jaundice and ascites may be noted.

Diagnosis of HE is made on the basis of medical history, and physical and mental status examinations with the required clinical elements being knowledge of existent liver disease, precipitating factor(s), and/or prior history of HE. An EEG may show slow-wave activity, even in mild cases. An elevated serum ammonia level is characteristic but not essential, and correlates poorly with the level of encephalopathy Management of patients with chronic HE includes 1) provision of supportive care, 2) identification and removal of precipitating factors, 3) reduction of nitrogenous load from the gut, and 4) assessment of the need for long term therapy. The nitrogenous load from the gut is typically reduced using non-absorbable disaccharide (lactulose) and/or antibiotics.

Lactulose is considered a first-line treatment in the United States, but is not currently approved in the U.S. for either the treatment or prevention of HE. Lactulose is metabolized by the intestinal bacteria of the colon, which leads to reduced fecal pH, then to a laxative effect, and finally to fecal elimination. The reduced fecal pH ionizes ammonia ($NH_3$) to the ammonium ion ($NH_4^+$) which is used by the bacteria for amino acid and protein synthesis. This lowers the serum ammonia levels and improves mental function.

Conventional therapy aims to lower the production and absorption of ammonia. Lactulose is typically used in doses of 30-60 g daily. However, the dose can be titrated up to 20-40 g TID-QID to affect 2-3 semi-formed bowel movements per day. If lactulose cannot be administered orally or per nasogastric tube, for example to patients with stage 3 and 4 HE, it may be given as a 300 cc (200 g) retention enema. For acute encephalopathy, lactulose can be administered either orally, by mouth or through a nasogastric tube, or via retention enemas. The usual oral dose is 30 g followed by dosing every 1 to 2 hours until evacuation occurs. At that point, dosing is adjusted to attain two or three soft bowel movements daily.

Lactulose for is readily available over-the-counter. A convenient and relatively tasteless formulation, often referred to in the trade as "lactulose powder for oral solution" can be obtained, for example, from Bertek Pharmaceuticals, Sugarland, Tex. as Kristalose® in 10 and 20 gm packets. The lactulose syrups commonly sold as laxatives include Cephulac® Chronulac®, Cholac® and Enulose® These syrups can be substituted for lactulose powder by using sufficient syrup to provide the desired dosage of lactulose; typically, the named syrups contain about 10 gm lactulose in 15 ml of syrup.

Broad-spectrum, GI-active antibiotics including neomycin, metronidazole, vancomycin and paromomycin have been used with or without lactulose. Current guidelines recommend neomycin at 1 to 2 g/day by mouth with periodic renal and annual auditory monitoring or metronidazole at 250. Lactulose can induce diarrhea leading to dehydration, a precipitating factor of HE. Additionally, compliance with lactulose is limited by patient dislike of its overly sweet taste. In addition, a dosing schedule that is linked to bowel habits and side effects of flatulence, bloating, diarrhea (which leads to dehydration), and acidosis make lactulose difficult to use long-term.

Antibiotic use in treatment of HE is hampered by toxicity associated with long-term use. Specifically, systemic absorption of neomycin, metronidazole and ampicillin has led to rare cases of nephrotoxicity, ototoxicity, *S. enterocolitis*, and/or development of resistant bacterial strains. Additionally, neomycin inhibits only aerobic bacteria. Metronidazole is metabolized slowly in patients with hepatic dysfunction, has a potential for alcohol interactions (disulfiram-like effect), and high blood levels may result in seizures.

One gastrointestinal specific antibiotic is rifaximin. Rifaximin is a nonaminoglycoside, semisynthetic antibiotic derived from rifamycin O. It is a non-systemic, non-absorbed, broad-spectrum, oral antibiotic specific for enteric pathogens of the GI tract. Rifaximin was found to be advantageous in treatment of HE relative to previously used antibiotics; e.g., negligible systemic absorption (<0.4%) regardless of food intake or presence of GI disease and exhibits no plasma accumulation with high or repeat doses. The lack of systemic absorption makes rifaximin safe and well tolerated, thus improving patient compliance and reducing side effects associated with currently known treatments.

Rifaximin (INN; see The Merck Index, XIII Ed., 8304) is an antibiotic belonging to the rifamycin class of antibiotics, e.g., a pyrido-imidazo rifamycin. Rifaximin exerts its broad antibacterial activity, for example, in the gastrointestinal tract against localized gastrointestinal bacteria that cause infectious diarrhea, irritable bowel syndrome, small intestinal bacterial overgrowth, Crohn's disease, and/or pancreatic insufficiency. It has been reported that rifaximin is characterized by a negligible systemic absorption, due to its chemical and physical characteristics (Descombe J. J. et al. Pharmacokinetic study of rifaximin after oral administration in healthy volunteers. Int J Clin Pharmacol Res, 14 (2), 51-56, (1994)).

Rifaximin is described in Italian Patent IT 1154655 and EP 0161534. EP patent 0161534 discloses a process for rifaximin production using rifamycin O as the starting material (The Merck Index, XIII Ed., 8301). U.S. Pat. No.

7,045,620 B1 discloses polymorphic forms of rifaximin. The applications and patents referred to here are incorporated herein by reference in their entirety for all purposes A rifamycin class antibiotic is, for example, a compound having the structure of Formula I:

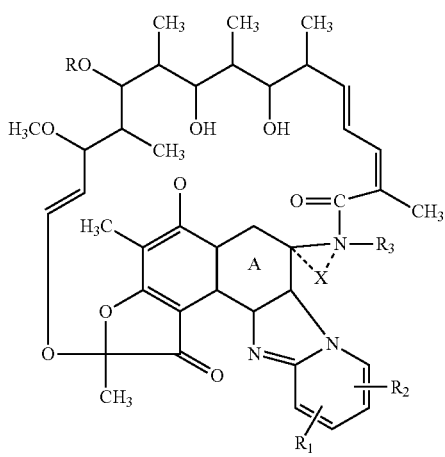

wherein A may be the structure $A_1$:

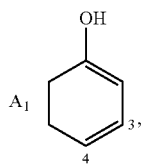

or the structure $A_2$

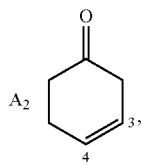

wherein, -x- is a covalent chemical bond or nil; R is hydrogen or acetyl;

$R_1$ and $R_2$ independently represent hydrogen, $(C_{1-4})$ alkyl, benzyloxy, mono- and di-$(C_{1-3})$ alkylamino-$(C_{1-4})$ alkyl, $(C_{1-3})$alkoxy-$(C_{1-4})$alkyl, hydroxymethyl, hydroxy-$(C_{2-4})$-alkyl, nitro or $R_1$ and $R_2$ taken together with two consecutive carbon atoms of the pyridine nucleus form a benzene ring unsubstituted or substituted by one or two methyl or ethyl groups; $R_3$ is a hydrogen atom or nil; with the proviso that, when A is $A_1$, -x- is nil and $R_3$ is a hydrogen atom; with the further proviso that, when A is $A_2$, -x- is a covalent chemical bond and $R_3$ is nil.

Also described herein is a compound as defined above, wherein A is $A_1$ or $A_2$ as above indicated, -x- is a covalent chemical bond or nil, R is hydrogen or acetyl, $R_1$ and $R_2$ independently represent hydrogen, $(C_{1-4})$alkyl, benzyloxy, hydroxy-$(C_{2-4})$ alkyl, di-$(C_{1-3})$ alkylamino-$(C_{1-4})$ alkyl, nitro or $R_1$ and $R_2$ taken together with two consecutive carbon atoms of the pyridine nucleus form a benzene ring and $R_3$ is a hydrogen atom or nil; with the proviso that, when A is $A_1$, -x- is nil and $R_3$ is a hydrogen atom; with the further proviso that, when A is $A_2$, -x- is a covalent chemical bond and $R_3$ is nil.

Also described herein is a compound as defined above, wherein A is $A_1$ or $A_2$ as above indicated, -x- is a covalent chemical bond or nil, R is acetyl, $R_1$ and $R_2$ independently represent hydrogen, $(C_{1-4})$ alkyl or $R_1$ and $R_2$ taken together with two consecutive carbon atoms of the pyridine nucleus form a benzene ring and $R_3$ is a hydrogen atom or nil; with the proviso that, when A is $A_1$, -x- is nil and $R_3$ is a hydrogen atom; with the further proviso that, when A is $A_2$, -x- is a covalent chemical bond and $R_3$ is nil.

Also described herein is a compound as defined above, which is 4-deoxy-4'-methyl-pyrido[1',2'-1,2]imidazo [5,4-c] rifamycin SV. Also described herein is a compound as defined above, which is 4-deoxy-pyrido [1',2':1,2]imidazo [5,4-c] rifamycin SV.

Also described herein is a compound as defined above, wherein A is as described above, -x- is a covalent chemical bond or nil; R is hydrogen or acetyl; $R_1$ and $R_2$ independently represent hydrogen, $(C_{1-4})$ alkyl, benzyloxy, mono- and di-$(C_{1-3})$alkylamino$(C_{1-4})$alkyl, $(C_{1-3})$alkoxy-$(C_{1-4})$ alkyl, hydroxymethyl, hydroxy-$(C_{2-4})$-alkyl, nitro or $R_1$ and $R_2$ taken together with two consecutive carbon atoms of the pyridine nucleus form a benzene ring unsubstituted or substituted by one or two methyl or ethyl groups; $R_3$ is a hydrogen atom or nil; with the proviso that, when A is $A_1$, -x- is nil and $R_3$ is a hydrogen atom; with the further proviso that, when A is $A_2$, -x- is a covalent chemical bond and $R_3$ is nil.

Rifaximin is a compound having the structure of formula II:

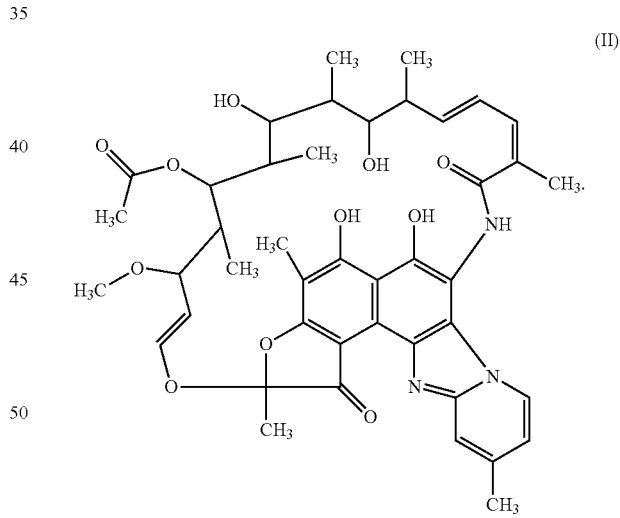

In certain embodiments, the antibiotic comprises one or more of a rifamycin, aminoglycoside, amphenicol, ansamycin, β-Lactam, carbapenem, cephalosporin, cephamycin, monobactam, oxacephem, lincosamide, macrolide, polypeptide, tetracycline, or a 2,4-diaminopyrimidine class antibiotic. Exemplary antibiotics of these classes are listed below.

Rifaximin exerts a broad antibacterial activity in the gastrointestinal tract against localized gastrointestinal bacteria that cause infectious diarrhea, including anaerobic strains. It has been reported that rifaximin is characterized by a negligible systemic absorption, due to its chemical and physical characteristics (Descombe J. J. et al. *Pharmacoki-*

*netic study of rifaximin after oral administration in healthy volunteers. Int J Clin Pharmacol Res,* 14 (2), 51-56, (1994)).

Without wishing to be bound by any particular scientific theories, rifaximin acts by binding to the beta-subunit of the bacterial deoxyribonucleic acid-dependent ribonucleic acid (RNA) polymerase, resulting in inhibition of bacterial RNA synthesis. It is active against numerous gram (+) and (−) bacteria, both aerobic and anaerobic. In vitro data indicate rifaximin is active against species of *Staphylococcus, Streptococcus, Enterococcus,* and Enterobacteriaceae. Bacterial reduction or an increase in antimicrobial resistance in the colonic flora does not frequently occur and does not have a clinical importance. Rifaximin is currently approved in 17 countries outside the US and was licensed by the Food and Drug Administration (FDA) for the US in May 2004.

It is to be understood that both the foregoing general description and the following detailed description are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

All documents, or portions of documents, cited in this application, including but not limited to patents, patent applications, articles, books, and treatises, are hereby expressly incorporated by reference in their entirety for any purpose.

One embodiment is a method of treating or preventing hepatic encephalopathy (HE) by administering a therapeutically effective amount of a gastrointestinal (GI) specific antibiotic to a subject. Examples of gastrointestinal antibiotics as used herein include rifamycin class antibiotics, such as rifaximin.

Embodiments of the invention relate to the discovery of the efficacy of gastrointestinal (GI) specific antibiotics for the treatment and prevention of Hepatic Encephalopathy. Embodiments relate to the use of GI specific antibiotics to prevent the onset of HE symptoms and also to lengthen the time to a first breakthrough HE episode. In one embodiment, the time to a first breakthrough HE episode was measured by an increase of the Conn score to Grade $\geq 2$ (e.g., 0 or 1 to $\geq 2$) or a Conn and asterixis score increase of one grade each for those subjects that have a baseline Conn Score of 0. In another embodiment, the time to breakthrough HE episode was measured by the time to any increase from baseline in either the Conn score (mental state grade) or asterixis grade, with Kaplan-Meier estimates of cumulative proportions of subjects with any increase at Days 28, 56, 84, 112, 140, and 168.

Another embodiment was a measurement of the time to a first HE-related hospitalization or the time to development of spontaneous bacterial peritonitis (SBP). Another embodiment was a mean change from baseline in blood ammonia concentration over time or a mean change from baseline in critical flicker frequency values over time. An additional embodiment was indicated by a mean daily lactulose consumption over time, shifts from baseline in Conn scores over time; or shifts from baseline in asterixis grades over time. Unless otherwise specified, a shift of a value is the change of that value from a baseline value.

Other measures of efficacy of the treatments described herein included mean change from baseline in Chronic Liver Disease Questionnaire (CLDQ) scores over time; mean change from baseline in Epworth Sleepiness Scale scores over time; and proportion of subjects who have an Epworth Sleepiness Scale score >10. The evaluation of severity of persistent hepatic encephalopathy may also be based, for example, on Conn scores.

In another embodiment, a subject suffering from, susceptible to or in remission from hepatic encephalopathy (HE) can be administered a rifamycin class antibiotic for between about 24 weeks and 24 months. In treating HE, the rifamycin class antibiotic may be administered to the subject for 12 months and longer, for example for a subject's entire life span. In one embodiment, the antibiotic is administered daily until the death of the subject.

In one embodiment, the invention relates to a method of decreasing a subject's risk of having a breakthrough event by administering to the subject a GI specific antibiotic. In one embodiment, the for subjects having a last HE episode equal to or greater than 90 days prior to starting on treatment, the risk of failure occurrence was reduced by 58%. In another embodiment, the risk of failure occurrence was reduced by between about 30-70%. In another embodiment, the risk was reduced by about 40% to 70%.

In one embodiment, for subjects having a last HE episode more than 90 days prior to administration of a GI specific antibiotic, the risk of failure occurrence was decreased by between about 60%. In another embodiment, the risk of failure occurrence was decreased by between about 2%-80%.

In another embodiment, for subjects having two or fewer HE episodes in the six months prior to starting on treatment, the risk of a breakthrough HE episode was decreased by about a 56%. In one embodiment, the risk of a breakthrough HE episode was decreased by between about a 20%-70%.

In another embodiment, for subjects having greater than two HE episodes in the six months prior to starting on treatment, the risk of a breakthrough HE episode was reduced by about 63%. In another embodiment, the risk was reduced by about 30%-80%.

In one embodiment, the therapeutically effective amount of a gastrointestinal (GI) specific antibiotic comprises from between about 1000 mg to about 1200 mg/day.

In one embodiment, the therapeutically effective amount of a gastrointestinal (GI) specific antibiotic comprises from between about 1100 mg to about 1200 mg/day.

According to one embodiment, the therapeutically effective amount of a gastrointestinal (GI) specific antibiotic comprises about 1150 mg/day.

In another embodiment, the therapeutically effective amount is a dosage regimen of one capsule or tablet of the formulation two times each day, wherein each tablet comprises about 550 mg of the gastrointestinal (GI) specific antibiotic, such as rifaximin.

In one embodiment, the therapeutically effective amount is a dosage regimen of two capsules or tablets three times each day, wherein each capsule comprises about 200 mg of the gastrointestinal (GI) specific antibiotic.

In one embodiment, the therapeutically effective amount is a dosage of 275 mg of a gastrointestinal (GI) specific antibiotic administered four times per day. In another embodiment, 275 mg of a gastrointestinal (GI) specific antibiotic is administered as two dosage forms two times per day.

Another embodiment is a method of maintaining remission of HE in a subject by administering a GI specific antibiotic to the subject.

Another embodiment is a method of increasing time to hospitalization for treatment of HE by administering to the subject a GI specific antibiotic. In one embodiment, the administration of a GI specific antibiotic reduces hospitalization frequency by about 48%. In another embodiment, a GI specific antibiotic reduces hospitalization frequency by from between about 13% to about 69%.

In one embodiment, treatment with the gastrointestinal (GI) specific antibiotic maintains remission of HE in the subject.

In one embodiment, the GI specific antibiotic is administered to the subject for six months, one year, two to three years or daily until the subject's death.

In one embodiment, a Conn score for the subject is improved over baseline following administration of a GI specific antibiotic.

In one embodiment, a quality of life (QoL) measurement is improved from baseline with administration of a GI specific antibiotic over a course of treatment with rifaximin.

In one embodiment, the GI specific antibiotic is administered to the subject with lactulose, prior to treatment with lactulose, or following treatment with lactulose.

In one embodiment, the GI specific antibiotic is administered with one or more of align, alinia, Lactulose, pentasa, cholestyramine, sandostatin, vancomycin, lactose, amitiza, flagyl, zegerid, prevacid, or miralax.

In one embodiment, following treatment with GI specific antibiotic, a Conn score (mental state grade) of a subject decreases.

In one embodiment, following treatment with a GI specific antibiotic, a Conn score increase from baseline is increased.

In one embodiment, following treatment with a GI specific antibiotic, a delay in time to an increase in Conn score is about 54%. For example, the percentage delay in time to increase in Conn score may be between about 30% to about 70%.

In another embodiment, administration of the GI specific antibiotic prevents an increase in Conn score. For example, administration of the GI specific antibiotic increases the time to an increase from baseline in a Conn score.

In one embodiment, administration of the GI specific antibiotic results in an increase of time to an increase from baseline in an asterixis grade.

In another embodiment, administration of the GI specific antibiotic results in a delay in the time to increase in asterixis grade.

In another embodiment, administration of the GI specific antibiotic results in an increase in time to first HE-related hospitalization.

In another embodiment, administration of the GI specific antibiotic results in an increase in the time to development of spontaneous bacterial peritonitis (SBP).

In another embodiment, administration of the GI specific antibiotic results in a decrease in blood ammonia concentration from baseline after administration of rifaximin. For example, the decrease in blood ammonia concentration may be from baseline to 170 days of about 6 µg/dL.

In another embodiment, administration of the GI specific antibiotic results in an increase in critical flicker frequency values from baseline after administration of rifaximin.

In another embodiment, administration of the GI specific antibiotic results in a decrease in daily lactulose consumption from baseline over time after administration with rifaximin.

In another embodiment, administration of the GI specific antibiotic results in a decrease in daily lactulose consumption is from between about 7 doses of lactulose to about 2 doses of lactulose.

In another embodiment, administration of the GI specific antibiotic results in a lactulose use that initially increases from baseline. For example, the lactulose use may be from between about 1 and about 30 days.

In another embodiment, administration of the GI specific antibiotic results in a shift in baseline in Conn scores over time after administration of rifaximin. For example, the shift in baseline in Conn scores may be from between about 1 to about 2.

In another embodiment, administration of the GI specific antibiotic results in a shift from baseline in asterixis grades over time.

In another embodiment, administration of the GI specific antibiotic results in a change from baseline in Chronic Liver Disease Questionnaire (CLDQ) scores over time.

In another embodiment, administration of the GI specific antibiotic results in a change from baseline in Epworth Sleepiness Scale scores over time after administration of rifaximin.

As is known, the Model for End-Stage Liver Disease (MELD) score can be utilized to predict liver disease severity based on serum creatinine, serum total bilirubin, and the international normalized ratio for prothrombin time INR. The MELD score and has been shown to be useful in predicting mortality in patients with compensated and decompensated cirrhosis. The maximum score given for MELD is 40. All values higher than 40 are given a score of 40.

In another embodiment, subjects having a MELD level of between about 1 to 24 responded to treatment for HE using administration of the GI specific. In another embodiment, subjects having a MELD level less than or equal to 10 responded to treatment with GI specific antibiotics. In another embodiment, subjects having a MELD level between 11 and 18 respond to treatment with GI specific antibiotics. In another embodiment, subjects having a MELD level between 19 and 24 respond to treatment with GI specific antibiotics.

One embodiment of the invention is a method of treating or preventing HE by administering 1100 mg of rifaximin per day to a patient for more than 28 days.

Another embodiment is a method of decreasing lactulose use in a subject. This method includes: administering rifaximin to a subject daily that is being treated with lactulose, and tapering lactulose consumption. For example, the lactulose consumption may be reduced by 1, 2, 3, 4, 5, 6 or more unit dose cups of lactulose from a baseline level. Alternatively, the lactulose use may be reduced by 5, 10, 15, 20, 25, 30, 34, 40, 45, 50, 55, 60, 65, or 70 g lactulose from a baseline level. In one embodiment, the baseline use of lactulose is no use.

One embodiment of the invention is a method of maintaining remission of HE in a subject comprising administering 550 mg of rifaximin twice a day (BID) to the subject.

Another embodiment is a method of increasing time to hospitalization for treatment of HE comprising, administering to a subject 550 mg of rifaximin two times per day (BID).

The term "administration" or "administering" includes routes of introducing a GI specific antibiotic to a subject to perform their intended function. Examples of routes of administration that may be used include injection (subcutaneous, intravenous, parenterally, intraperitoneally, intrathecal), oral, inhalation, rectal and transdermal. The pharmaceutical preparations may be given by forms suitable for each administration route. For example, these preparations are administered in tablets or capsule form, by injection, inhalation, eye lotion, eye drops, ointment, suppository, etc. administration by injection, infusion or inhalation; topical by lotion or ointment; and rectal by suppositories. Oral administration is preferred. The injection can be bolus or can be continuous infusion. Depending on the route of administration, a GI specific antibiotic can be coated with or disposed in a selected material to protect it from natural conditions that may detrimentally effect its ability to perform its intended function. A GI specific antibiotic can be administered alone, or in conjunction with either another agent or agents as described above or with a pharmaceutically-acceptable carrier, or both. A GI specific antibiotic can be administered prior to the administration of the other agent, simultaneously with the agent, or after the administration of the agent. Furthermore, a GI specific antibiotic can also be administered in a proform, which is converted into its active metabolite, or more active metabolite in vivo.

Administration "in combination with" one or more further therapeutic agents includes simultaneous (concurrent) and consecutive administration in any order.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved.

As used herein, an "increase" or "decrease" in a measurement, unless otherwise specified, is typically in comparison to a baseline value. For example, an increase in time to hospitalization for subjects undergoing treatment may be in comparison to a baseline value of time to hospitalization for subjects that are not undergoing such treatment. In some instances an increase or decrease in a measurement can be evaluated based on the context in which the term is used.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN, polyethylene glycol (PEG).

The term "effective amount" includes an amount effective, at dosages and for periods of time necessary, to achieve the desired result, e.g., sufficient to treat or prevent HE in a patient or subject. An effective amount of a GI specific antibiotic may vary according to factors such as the disease state, age, and weight of the subject, and the ability of a GI specific antibiotic to elicit a desired response in the subject. Dosage regimens may be adjusted to provide the optimum therapeutic response. An effective amount is also one in which any toxic or detrimental effects (e.g., side effects) of a GI specific antibiotic are outweighed by the therapeutically beneficial effects.

"Ameliorate," "amelioration," "improvement" or the like refers to, for example, a detectable improvement or a detectable change consistent with improvement that occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range between about any two of these values. Such improvement or change may be observed in treated subjects as compared to subjects not treated with rifaximin, where the untreated subjects have, or are subject to developing, the same or similar disease, condition, symptom or the like. Amelioration of a disease, condition, symptom or assay parameter may be determined subjectively or objectively, e.g., self assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s) or by detection of HE episodes in a subject. Amelioration may be transient, prolonged or permanent or it may be variable at relevant times during or after a GI specific antibiotic is administered to a subject or is used in an assay or other method described herein or a cited reference, e.g., within timeframes described infra, or about 1 hour after the administration or use of a GI specific antibiotic to about 28 days, or 1, 3, 6, 9 months or more after a subject(s) has received such treatment.

The "modulation" of, e.g., a symptom, level or biological activity of a molecule, or the like, refers, for example, that the symptom or activity, or the like is detectably increased or decreased. Such increase or decrease may be observed in treated subjects as compared to subjects not treated with a GI specific antibiotic, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or within any range between any two of these values. Modulation may be determined subjectively or objectively, e.g., by the subject's self assessment, by a clinician's assessment or by conducting an appropriate assay or measurement, including, e.g., quality of life assessments or suitable assays for the level or activity of molecules, cells or cell migration within a subject. Modulation may be transient, prolonged or permanent or it may be variable at relevant times during or after a GI specific antibiotic is administered to a subject or is used in an assay or other method described herein or a cited reference, e.g., within times descried infra, or about 1 hour of the administration or use of a GI specific antibiotic to about 3, 6, 9 months or more after a subject(s) has received a GI specific antibiotic.

The term "modulate" may also refer to increases or decreases in the activity of a cell in response to exposure to a GI specific antibiotic, e.g., the inhibition of proliferation and/or induction of differentiation of at least a sub-population of cells in an animal such that a desired end result is achieved, e.g., a therapeutic result of GI specific antibiotic used for treatment may increase or decrease over the course of a particular treatment.

The term "obtaining" as in "obtaining a GI specific antibiotic" is intended to include purchasing, synthesizing or otherwise acquiring a GI specific antibiotic.

The phrases "parenteral administration" and "administered parenterally" as used herein includes, for example, modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The language "a prophylactically effective amount" of a compound refers to an amount of a GI specific antibiotic which is effective, upon single or multiple dose administration to the subject, in preventing or treating HE.

The term "pharmaceutical agent composition" (or agent or drug) as used herein refers to a chemical compound, composition, agent or drug capable of inducing a desired therapeutic effect when properly administered to a patient. It does not necessarily require more than one type of ingredient.

The compositions may be in the form of tablets, capsules, powders, granules, lozenges, liquid or gel preparations. Tablets and capsules for oral administration may be in a form suitable for unit dose presentation and may contain conventional excipients. Examples of these are: binding agents such as syrup, acacia, gelatin, sorbitol, tragacanth, and polyvinylpyrrolidone; fillers such as lactose, sugar, maize-starch, calcium phosphate, sorbitol or glycine; tableting lubricants, such as magnesium stearate, silicon dioxide, talc, polyethylene glycol or silica; disintegrants, such as potato starch; or acceptable wetting agents, such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, e.g., sorbitol, syrup, methyl cellulose, glucose syrup, gelatin, hydrogenated edible fats, emulsifying agents, e.g., lecithin, sorbitan monooleate, or acacia; non-aqueous vehicles (including edible oils), e.g., almond oil, fractionated coconut oil, oily esters such as glycerine, propylene glycol, or ethyl alcohol; preservatives such as methyl or propyl p-hydroxybenzoate or sorbic acid, and, if desired, conventional flavoring or coloring agents.

The phrases "systemic administration," "administered systemically," "peripheral administration," and "administered peripherally," as used herein mean the administration of a GI specific antibiotic, drug or other material, such that it enters the subject's system and, thus, is subject to metabolism and other like processes, for example, subcutaneous administration.

The language "therapeutically effective amount" of a GI specific antibiotic refers to an amount of a GI specific antibiotic which is effective, upon single or multiple dose administration to the subject, in inhibiting the bacterial growth and/or invasion, or in decreasing symptoms, such as HE episodes, relating to bacterial growth in a subject. "Therapeutically effective amount" also refers to the amount of a therapy (e.g., a composition comprising a GI specific antibiotic), which is sufficient to reduce the severity of HE in a subject.

As used herein, the terms "prevent," "preventing," and "prevention" refer to the prevention of the recurrence, onset, or development HE episodes or more symptoms of HE. Preventing includes protecting against the occurrence and severity of HE episodes.

As used herein, the term "prophylactically effective amount" refers to the amount of a therapy (e.g., a composition comprising a GI specific antibiotic) which is sufficient to result in the prevention of the development, recurrence, or onset of HE episodes or to enhance or improve the prophylactic effect(s) of another therapy.

"Rifaximin", as used herein, includes solvates and polymorphous forms of the molecule, including, for example, $\alpha$, $\beta$, $\gamma$, $\delta$, $\varepsilon$, $\eta$, $\zeta$ and amorphous forms of rifaximin. These forms are described in more detail, for example, in U.S. Ser. Nos. 11/873,841; 11/658,702; EP 05 004 635.2, filed 3 May 2005; U.S. Pat. No. 7,045,620; U.S. 61/031,329; and G. C. Viscomi, et al., CrystEngComm, 2008, 10, 1074-1081 (April 2008). Each of these references is hereby incorporated by reference in entirety.

"Polymorphism", as used herein, refers to the occurrence of different crystalline forms of a single compound in distinct hydrate status, e.g., a property of some compounds and complexes. Thus, polymorphs are distinct solids sharing the same molecular formula, yet each polymorph may have distinct physical properties. Therefore, a single compound may give rise to a variety of polymorphic forms where each form has different and distinct physical properties, such as solubility profiles, melting point temperatures, hygroscopicity, particle shape, density, flowability, compactibility and/or x-ray diffraction peaks. The solubility of each polymorph may vary, thus, identifying the existence of pharmaceutical polymorphs is essential for providing pharmaceuticals with predictable solubility profiles. It is desirable to investigate all solid state forms of a drug, including all polymorphic forms, and to determine the stability, dissolution and flow properties of each polymorphic form. Polymorphic forms of a compound can be distinguished in a laboratory by X-ray diffraction spectroscopy and by other methods such as, infrared spectrometry. For a general review of polymorphs and the pharmaceutical applications of polymorphs see G. M. Wall, Pharm Manuf. 3, 33 (1986); J. K. Haleblian and W. McCrone, J Pharm. Sci., 58, 911 (1969); and J. K. Haleblian, J. Pharm. Sci., 64, 1269 (1975), all of which are incorporated herein by reference.

As used herein, "breakthrough HE," includes, for example, an increase of the Conn score to Grade $\geq 2$ (e.g., 0 or 1 to $\geq 2$) or a Conn and Asterixis score increase of 1 grade each for those subjects that have a baseline Conn score of 0.

As used herein, "time to the first breakthrough HE episode," includes, for example, the duration between the date of first administration of rifaximin and the date of first breakthrough HE episode.

As used herein, "time to first HE-related hospitalization," includes, for example, the duration between the first dose of rifaximin and the date of first HE-related hospitalization.

As used herein, "time to an increase from baseline in the Conn score" includes, for example, the duration between the first dose of rifaximin and the date of first increase in Conn score.

As used herein, "time to an increase from baseline in the asterixis grade", includes, for example, the duration between the first dose of rifaximin and the date of first increase in asterixis grade.

As used herein, "mean change from baseline in the fatigue domain score of Chronic Liver Disease Questionnaire (CLDQ), at end of treatment (EOT)" is the mean score with a baseline from before the first administration of rifaximin.

As used herein, "mean change from baseline in blood ammonia concentration at EOT," includes the mean score with a baseline from before the first administration of rifaximin.

As used herein, the "time to diagnosis of spontaneous bacterial peritonitis (SBP)," includes, for example, the duration between the first dose of rifaximin and the date of first episode of SBP.

As used herein, the "mean change from baseline at each post-baseline in critical flicker frequency values," is measured, for example, from a baseline established before the first administration of rifaximin.

"GI specific antibiotic," and "GI antibiotic" as used herein include antibiotic known to have an effect on GI disease. For example, a rifamycin class antibiotic (e.g., rifaximin), neomycin, metronidazole, teicoplanin, ciprofloxacin, doxycycline, tetracycline, augmentin, cephalexin, penicillin, ampicillin, kanamycin, rifamycin, vancomycin, rifaximin, and combinations thereof are useful GI specific antibiotics. Even more preferable are GI specific antibiotics with low systemic absorption, for example, rifaximin. Low systemic absorption includes, for example, less than 10% absorption, less than 5% absorption, less than 1% absorption and less than 0.5% absorption. Low systemic absorption also includes, for example, from between about 0.01-1% absorption, from between about 0.05-1% absorption, from between about 0.1-1% absorption, from between about 1-10% absorption, or from between about 5-20% absorption.

As used herein, "subject" includes organisms which are capable of suffering from a bowel disorder or other disorder treatable by rifaximin or who could otherwise benefit from the administration of a rifaximin as described herein, such as human and non-human animals. Preferred human animals include human subjects. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc. Susceptible to a bowel disorder is meant to include subjects at risk of developing a bowel disorder infection, i.e., subjects suffering from immune suppression, subjects that have been exposed to other subjects with a bacterial infection, physicians, nurses, subjects traveling to remote areas known to harbor bacteria that causes travelers' diarrhea, etc.

The language "a prophylactically effective amount" of a compound refers to an amount of a compound of the invention of formula I, formula II, or otherwise described herein which is effective, upon single or multiple dose administration to the subject, in preventing or treating hepatic encephalopathy.

Another embodiment includes articles of manufacture that comprise, for example, a container holding a pharmaceutical composition suitable for oral administration of rifaximin in combination with printed labeling instructions providing a discussion of when a particular dosage form extends remission of HE or prevents or delays future episodes of HE. The dosage can be modified for administration to a subject suffering from HE, or include labeling for administration to a subject suffering from HE. Exemplary dosage forms and administration protocols are described infra. The composition will be contained in any suitable container capable of holding and dispensing the dosage form and which will not significantly interact with the composition and will further be in physical relation with the appropriate labeling. The labeling instructions may be consistent with the methods of treatment as described hereinbefore. The labeling may be associated with the container by any means that maintain a physical proximity of the two, by way of non-limiting example, they may both be contained in a packaging material such as a box or plastic shrink wrap or may be associated with the instructions being bonded to the container such as with glue that does not obscure the labeling instructions or other bonding or holding means.

In one embodiment, the instructions will inform or advise a health care worker, prescribing physician, a pharmacist, or a subject that they should advise a patient suffering from hepatic encephalopathy that administration of rifaximin may induce cytochrome P450. In another embodiment, the instructions will inform the subject and/or the healthcare provider that there is an extended time to remission or relapse of subjects that take rifaximin. In another embodiment, the instructions will inform the subject and/or the healthcare worker or provider that rifaximin does not significantly alter the $C_{max}$, $AUC_{0-t}$, or $AUC_{0-\infty}$ of midazolam. In another embodiment, the instructions will inform the subject and/or the healthcare worker or provider that rifaximin does not increase the risk of QT prolongation.

Packaged compositions are also provided, and may comprise a therapeutically effective amount of rifaximin tablets or capsules. Kits are also provided herein, for example, kits for treating HE in a subject. The kits may contain, for example, rifaximin and instructions for use when treating a subject for an HE. The instructions for use may contain prescribing information, dosage information, storage information, and the like Kits may include pharmaceutical preparations of the GI specific antibiotics along with pharmaceutically acceptable solutions, carriers and excipients.

The α, β, γ, delta, epsilon and amorphous forms of rifaximin can be advantageously used in the production of medicinal preparations having antibiotic activity, containing rifaximin, for both oral and topical use. The medicinal preparations for oral use may contain rifaximin α or β or γ together with other excipients, for example diluting agents such as mannitol, lactose and sorbitol; binding agents such as starchs, gelatines, sugars, cellulose derivatives, natural gums and polyvinylpyrrolidone; lubricating agents such as talc, stearates, hydrogenated vegetable oils, polyethylenglycol and colloidal silicon dioxide; disintegrating agents such as starchs, celluloses, alginates, gums and reticulated polymers; coloring, flavoring and sweetening agents.

Solid preparations of gastrointestinal specific antibiotics administrable by the oral route include for instance coated and uncoated tablets, soft and hard gelatin capsules, sugar-coated pills, lozenges, wafer sheets, pellets and powders in sealed packets.

Medicinal preparations may contain gastrointestinal specific antibiotics together with usual excipients, such as white petrolatum, white wax, lanoline and derivatives thereof, stearylic alcohol, red iron oxide, propylene glycol, talc, sodium lauryl sulfate, ethers of fatty polyoxyethylene alcohols, disodium edentate, glycerol palmitostearate, esters of fatty polyoxyethylene acids, sorbitan monostearate, glyceryl monostearate, propylene glycol monostearate, hypromellose, polyethylene glycols, sodium starch glycolate, methylcellulose, hydroxymethyl propylcellulose, sodium carboxymethylcellulose, microcrystalline cellulose, colloidal aluminium and magnesium silicate, titanium dioxide, propylene glycol, colloidal silicon dioxide, or sodium alginate.

West Haven Criteria (Conn Score):

Measurements of change in mental status may be done, for example, by the Conn score (also known as the West Haven score). The Conn score has been widely used as a measure of mental state in HE studies and is based on the criteria of Parsons-Smith as modified by Conn. Asterixis will not be considered when assessing the subject's status using the Conn scoring criteria listed below.

The scale used in the Conn scoring system is provided below.

Grade 0=No personality or behavioral abnormality detected

Grade 1=Trivial lack of awareness, euphoria or anxiety; shortened attention span; impairment of addition or subtraction Grade 2=Lethargy; disorientation for time; obvious personality change; inappropriate behavior Grade 3=Somnolence to semi-stupor, responsive to stimuli; confused; gross disorientation; bizarre behavior Grade 4=Coma; unable to test mental state

EXAMPLES

It should be appreciated that embodiments of the invention should not be construed to be limited to the examples, which are now described; rather, the invention should be construed to include any and all applications provided herein and all equivalent variations within the skill of the ordinary artisan.

Example 1

Subjects were instructed to take one tablet of 550 mg of rifaximin by mouth 2 times per day—approximately every 12 hours. The rifaximin may be co-administered with other medications, for example, lactulose, antidepressants, anti-inflammatory, methadone, prescription and non-prescription sleep aids (e.g., Lunesta™ (eszopiclone) and Ambien® (zolpidem tartrate)), and antihistamines, diuretics, laxatives or stool softeners, neurontin (gabapentin) and lyrica (pregabalin).

Lactulose use was optional for subjects. For subjects who used lactulose, it was titrated to a dose during the 3 to 7-day observation period according to accepted medical practice.

Asterixis Grade

Asterixis (flapping tremor) was determined with the subject holding both arms and forearms extended with wrists dorsiflexed and fingers open for ≥30 seconds. Asterixis was measured on a continuum of 5 grades, e.g., grades 0 and 4=no abnormal movement vs. almost continuous flapping motions, respectively as shown below:

Grade 0=No tremors;

Grade 1=Rare flapping motions;

Grade 2=Occasional, irregular flaps;

Grade 3=Frequent flaps; and

Grade 4=Almost continuous flapping motions.

Efficacy in regard to asterixis grade was measured as time to any increase from baseline in asterixis grade. Time to an increase in asterixis grade was computed as the number of days from the first dose of rifaximin to the initial occurrence of an increase from baseline in asterixis grade.

Breakthrough HE Episode

Relative risk of experiencing a breakthrough HE episode (e.g., Conn score Grade ≥2, (e.g., 0 or 1 to ≥2) or a Conn and asterixis score increase of 1 grade each) for each subject in the trial taking either rifaximin or the placebo was measured. The analysis compared time to first breakthrough HE episode for rifaximin versus placebo using survival analysis methods. Time to first breakthrough HE episode was computed as the number of days from the first dose of rifaximin to the initial occurrence of breakthrough HE (e.g., Conn score Grade ≥2, or a Conn and asterixis score increase of 1 grade each).

Change in mental status was measured by the Conn score (also known as the West Haven score). The Conn score has been widely used as a measure of mental state in HE studies and is based on the criteria of Parsons-Smith as modified by Conn. The scale used in the Conn scoring system is described above.

Subjects had a Conn score of 0 or 1. An increase in the Conn score of greater than or equal to grade 2 was considered as a breakthrough HE episode.

Hepatic Encephalopathy Scoring Algorithm (HESA)

The Hepatic Encephalopathy Scoring Algorithm (HESA) is a method that uses both clinical and neuropsychological assessments to assess mental status. The Algorithm has been validated previously and has been correlated with the Conn criteria.

Critical Flicker Frequency scores

The critical flicker frequency (CFF) was assessed for each subject using a specialized CFF instrument. The CFF is the frequency at which the subject observes a constant light transition to a flickering light and is measured in Hertz (Hz). CFF is an objective assessment of mental status. A CFF value of 39 Hz has been shown to be the threshold for separation between subjects who have manifest HE (e.g., Conn ≥1) and those without HE symptoms (e.g., Conn=0), with a lower CFF value indicating more severe HE[43].

The CFF was measured on a continuous scale and was the mean of 8 separate fusion-to-flicker transition tests performed in rapid succession.

Ammonia Concentrations

Venous blood samples (10 mL) were collected and ammonia concentrations were obtained by methods known in the art.

Time to increase from baseline in either the Conn score (mental state grade) or asterixis grade To analyze the time to a first breakthrough HE episode, survival analysis methods were used to assess the effectiveness of the rifaximin treatment on the time to increase from baseline in either the Conn score (mental state grade) or asterixis grade. Time to increase in either the Conn score or asterixis grade was computed as the number of days from the first dose of rifaximin to the initial occurrence of either an increase from baseline in Conn score or asterixis grade. The analysis of time to increase in either Conn score or asterixis grade were based on the comparison of time to event between rifaximin and placebo.

Time to First HE-Related Hospitalization

The effect of rifaximin on time to first HE-related hospitalization was determined. Time to first HE-related hospitalization was computed as the number of days from the first dose of rifaximin to the first hospitalization for an HE related event. The analysis of time to first HE-related hospitalization was based on the comparison of time to hospitalization between rifaximin and placebo.

Time to Development of Spontaneous Bacterial Peritonitis

The effect of rifaximin on time to development of spontaneous bacterial peritonitis (SBP) was determined. Time to development of SBP was computed as the number of days from the first dose of rifaximin to the time of peritoneal fluid collection that resulted in a positive test for SBP. The analysis of time to development of SBP was based on the comparison of time to event between rifaximin and placebo.

Mean Change from Baseline in Blood Ammonia Concentration and Critical Flicker Frequency Values Over Time Mean values and mean changes from baseline in blood ammonia concentration and critical flicker frequency values were collected. Analyses of blood ammonia concentrations and critical flicker frequency values were based upon quantitative values (not qualitative grades). Treatment differences for mean change from baseline in these parameters was estimated using a mixed effects model with fixed effects for time and baseline value.

Mean Daily Lactulose Consumption Over Time

A subject's daily lactulose consumption was used to compute mean daily lactulose consumption for each month. Treatment differences for mean change from baseline in mean daily lactulose consumption were estimated.

CLDQ

The CLDQ includes 29 items in the following six domains: abdominal symptoms (three items), fatigue (five items), systemic symptoms (five items), activity (three items), emotional function (eight items), and worry (five items). Summary scores for the CLDQ overall and each of the six domains were computed and summarized at baseline and Days 28, 56, 84, 112, 140 and 168 using descriptive statistics. Treatment differences for mean change in overall score and domain scores from baseline to Days 28, 56, 84, 112, 140 and 168 were collected summarized and compared between treatments.

Treatment differences for mean change from baseline to EOT were determined as the change from baseline at EOT in fatigue domain score of Chronic Liver Disease Questionnaire (CLDQ). Similarly, the mean change from baseline in blood ammonia concentration at EOT was also determined.

Assessment of Quality of Life

The SF-36, Chronic Liver Disease Questionnaire (CLDQ), and Epworth Sleepiness Scale were used to measure health related quality of life. The 29 item CLDQ questionnaire consists of the following domains: fatigue, activity, emotional function, abdominal symptoms, systemic symptoms, and worry.

Epworth Sleepiness Scale

Total scores for the Epworth Sleepiness Scale were computed and summarized at baseline and Days 28, 56, 84, 112, 140 and 168 using descriptive statistics. Treatment differences for mean change in total scores from baseline to Days 28, 56, 84, 112, 140 and 168 were summarized and compared between treatments.

FIG. 1 is a line graph showing Lactulose daily use between subjects taking placebos and subjects taking rifaximin as described above.

Figure 2:
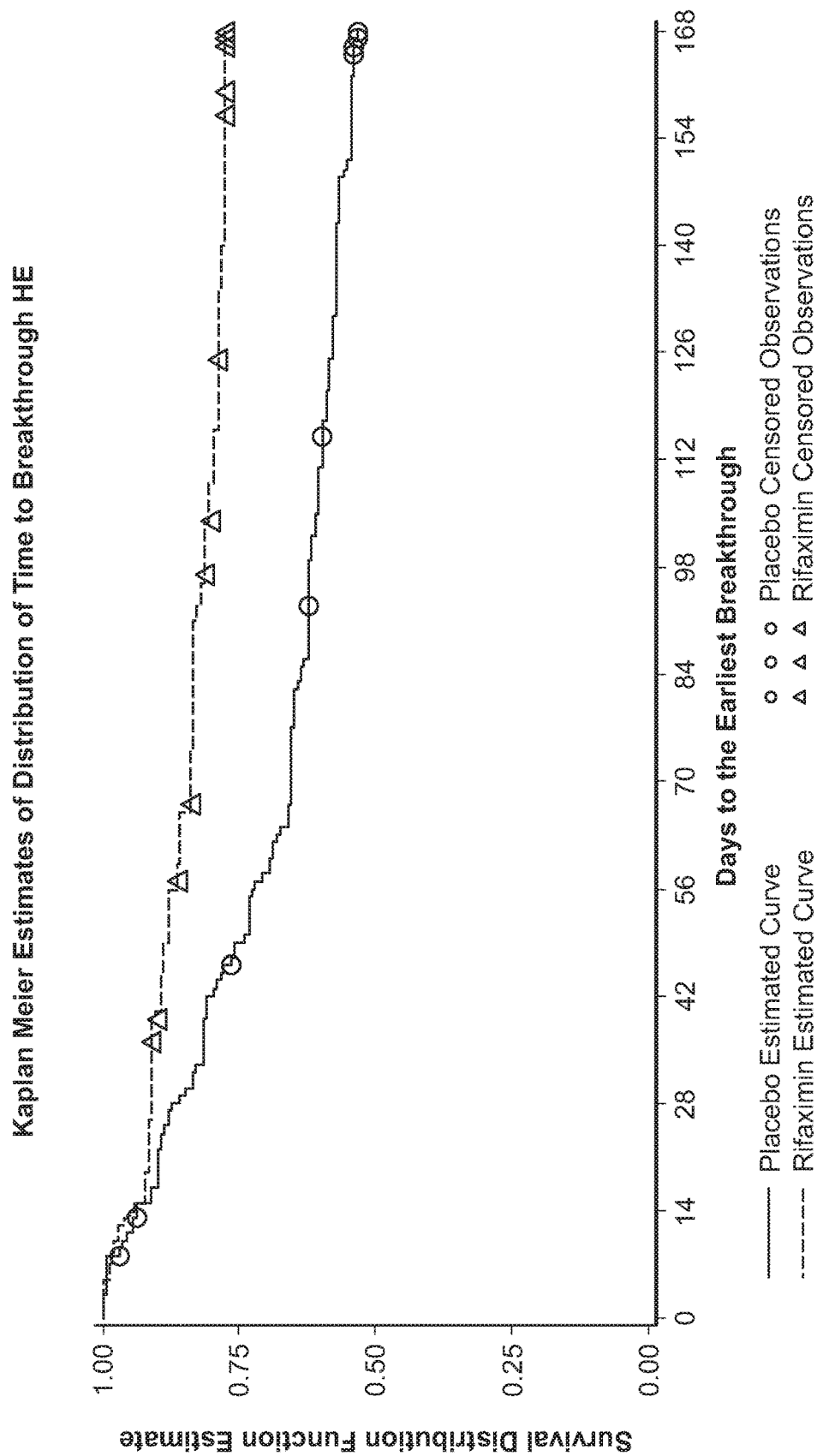
FIG. 2 is a line graph showing Kaplan Meier estimates of the distribution of time to a breakthrough HE event.

FIG. 2 is a line graph showing Kaplan Meier estimates of the distribution of time to a breakthrough HE event for the placebo group and the rifaximin group. As indicated there was an increased time to breakthrough HE events for subjects taking rifaximin in comparison to subjects taking the placebo.

Figure 3:
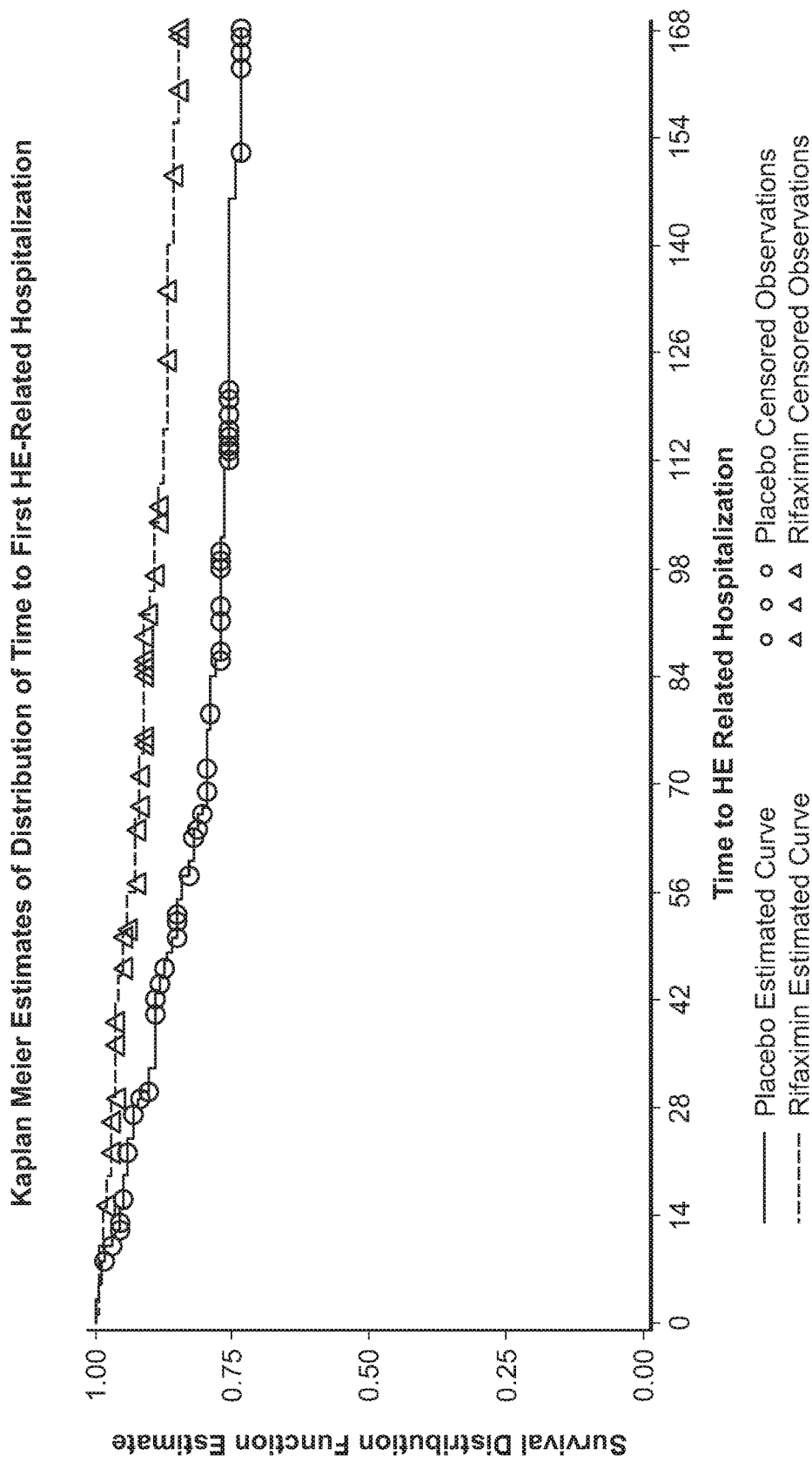
FIG. 3 is a line graph showing Kaplan Meier estimates of the distribution of time to a first HE related hospitalization.

FIG. 3 is a line graph showing Kaplan Meier estimates of the distribution of time to a first HE related hospitalization. As indicated there was an increased time to hospitalization for subjects taking rifaximin in comparison to the placebo group.

Figure 4:
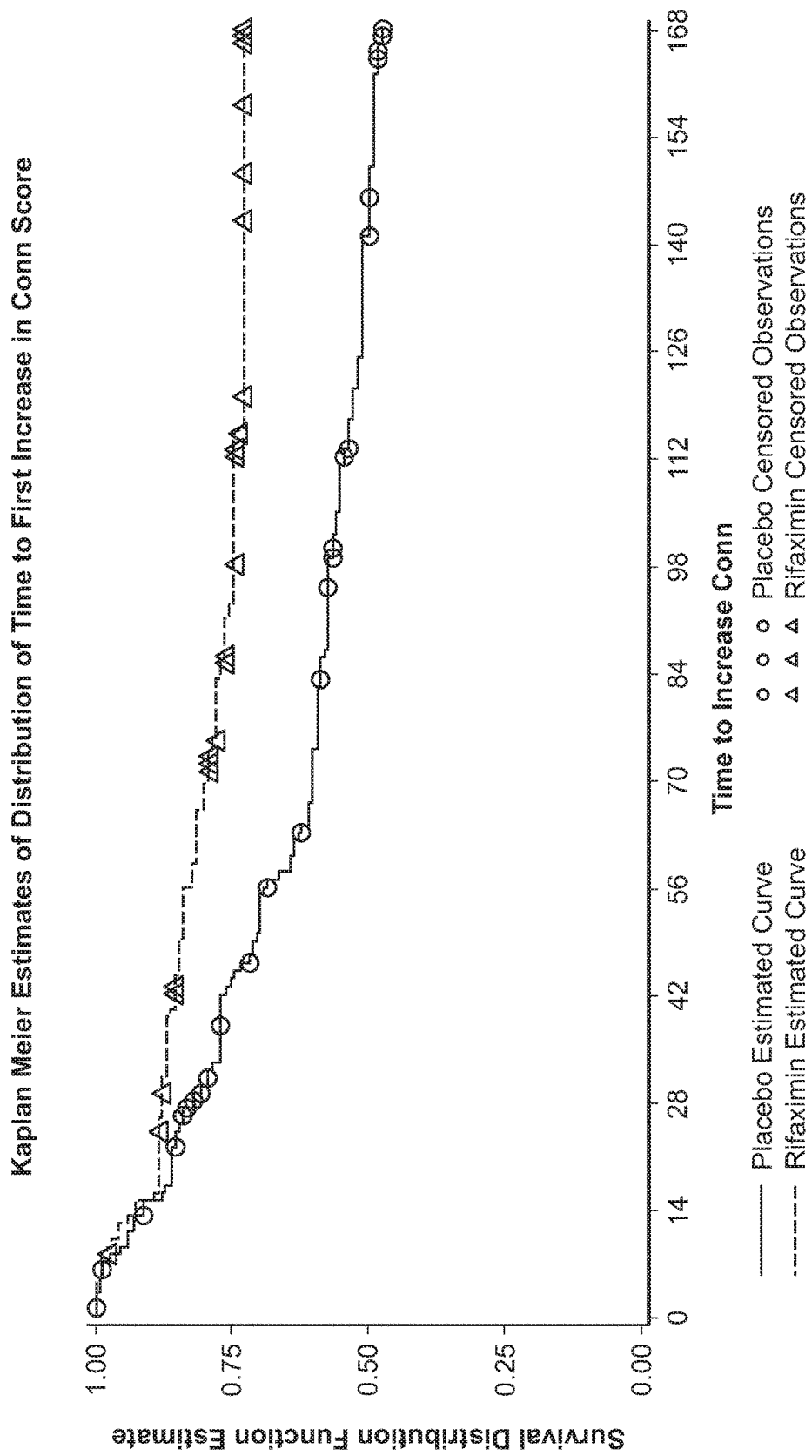
FIG. 4 is a line graph showing Kaplan Meier estimates of the distribution of time to a first increase in Conn scores.

FIG. 4 is a line graph showing Kaplan Meier estimates of the distribution of time to a first increase in Conn scores. As indicated there was an increased time to the first increase in Conn scores for subjects taking rifaximin in comparison to the placebo group.

Figure 5:
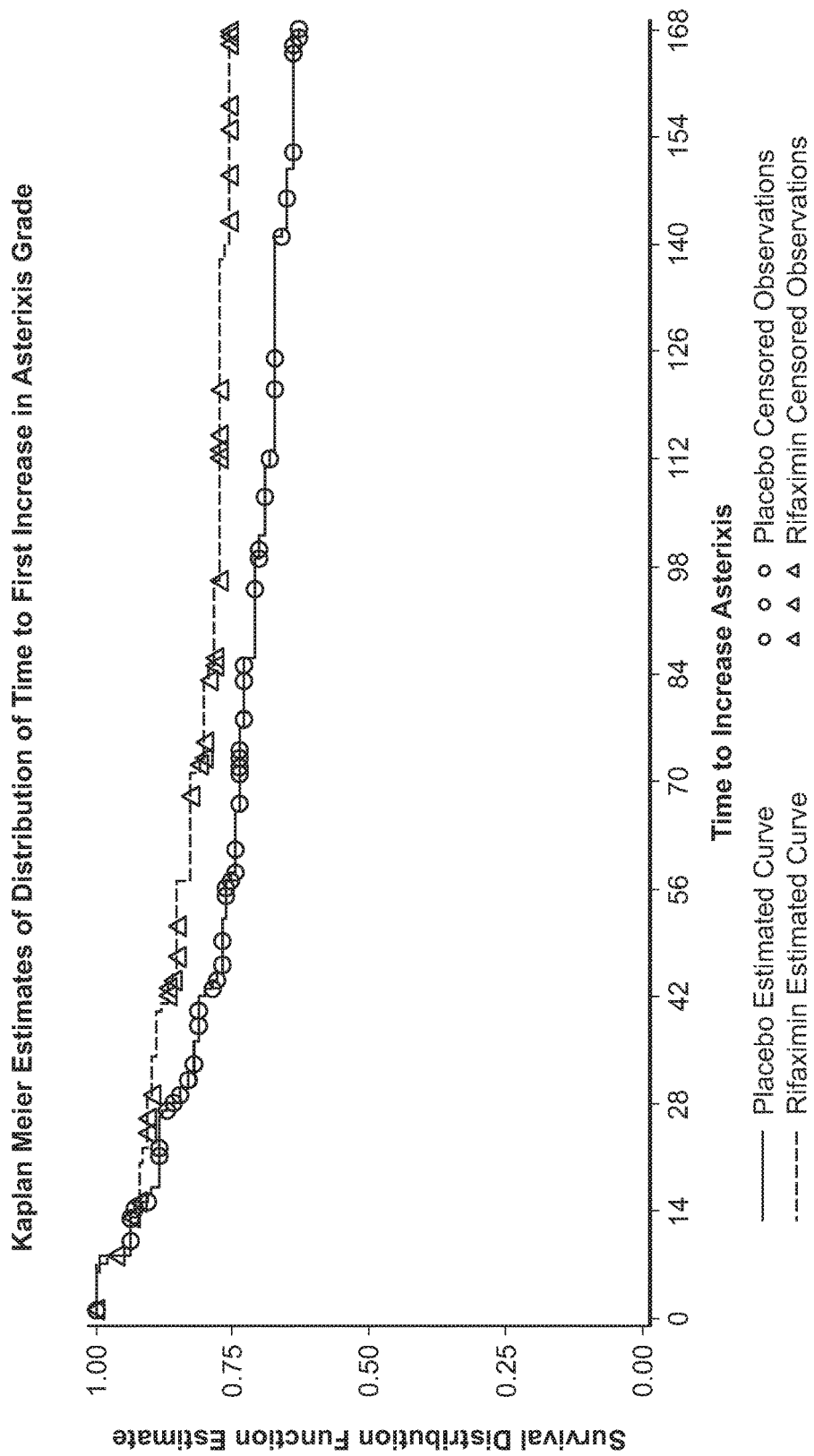
FIG. 5 is a line graph showing Kaplan Meier estimates of the distribution of time to a first increase in an Asterixis grade.
Figure 6:
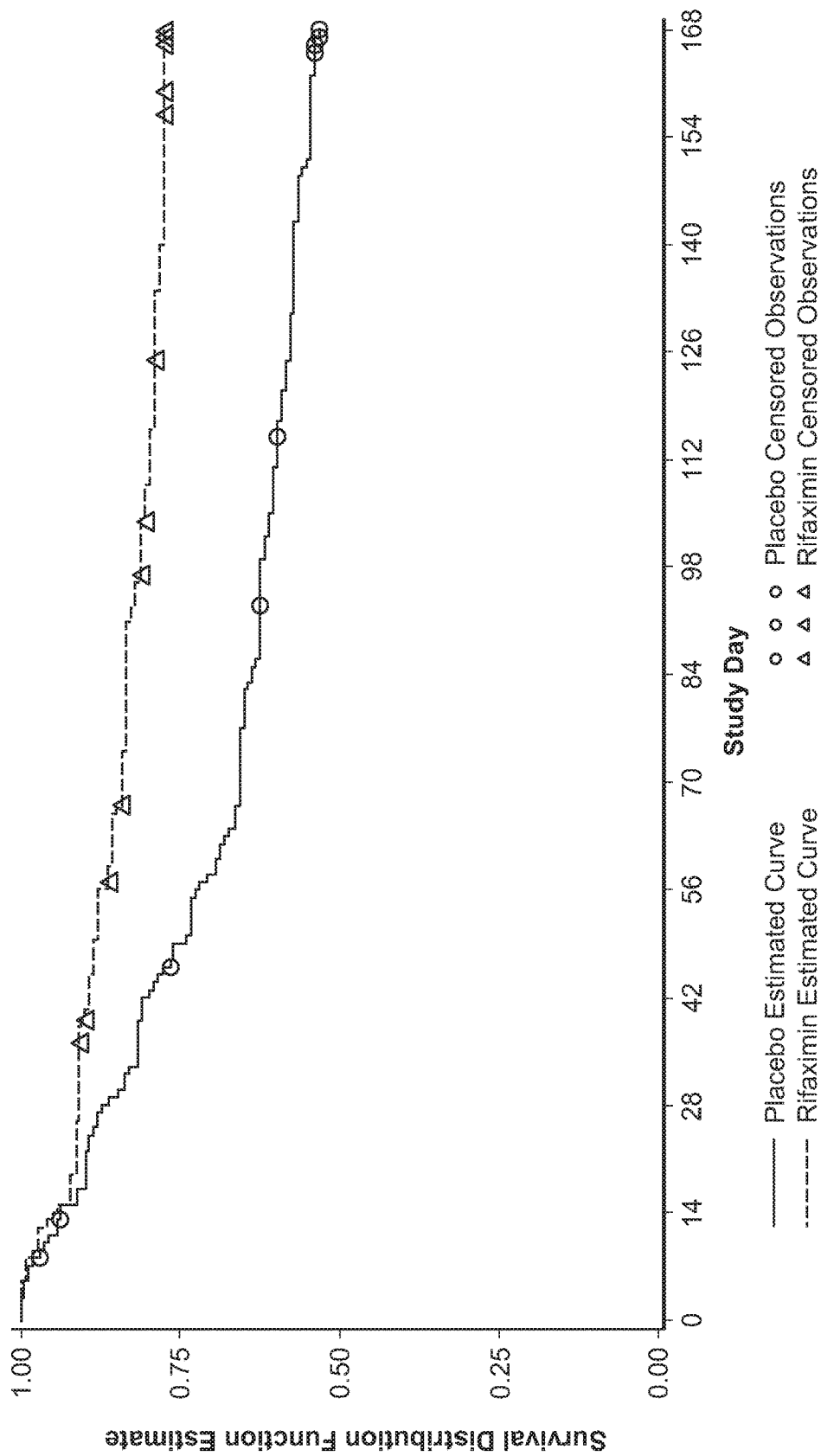
FIG. 6 depicts the time to first breakthrough over the episode (up to 6 months of treatment, day 170 in the first study) (ITT Population).

FIG. 5 is a line graph showing Kaplan Meier estimates of the distribution of time to a first increase in Asterixis grade. As indicated there was an increased time to the first increase in Asterixis grade for subjects taking rifaximin in comparison to the placebo group.

Example 2

The following tables provide further evidence supporting the advantageous use of GI specific antibiotics, such as rifaximin, to treat subjects suffering from HE.

TABLE 1

Time to Onset of Breakthrough HE Episode

| | Placebo (N = 159) | | | | | 550 mg Rifaximin BID (N = 140) | | | | |
|---|---|---|---|---|---|---|---|---|---|---|
| Days | At Risk | Occurrences of Events | Cumulative Occurrences of Events | Conditional Probability of Events (SE) | Survival | At Risk | Occurrences of Events | Cumulative Occurrences of Events | Conditional Probability of Events (SE) | Survival |
| [0-28) | 158 | 20 | 20 | 0.13 (0.03) | 1.0000 | 140 | 13 | 13 | 0.09 (0.02) | 1.0000 |
| [28-56) | 137 | 23 | 43 | 0.17 (0.03) | 0.8734 | 126 | 4 | 17 | 0.03 (0.02) | 0.9071 |
| [56-84) | 113 | 14 | 57 | 0.12 (0.03) | 0.7262 | 120 | 6 | 23 | 0.05 (0.02) | 0.8783 |
| [84-140) | 98 | 10 | 67 | 0.10 (0.03) | 0.6363 | 112 | 7 | 30 | 0.06 (0.02) | 0.8344 |
| [140-168) | 84 | 6 | 73 | 0.07 (0.03) | 0.5713 | 98 | 1 | 31 | 0.01 (0.01) | 0.7820 |
| >=168 | 38 | 0 | 73 | 0.00 (0.00) | 0.5305 | 46 | 0 | 31 | 0.00 (0.00) | 0.7740 |

Harzard Ratio: 0.421
95% CI: (0.276, 0.641)
p-value: <.0001

TABLE 2

Time to Onset of Breakthrough HE Episode by Baseline Conn Score Level

| | Placebo (N = 107) | | | | | 550 mg Rifaximin BID (N = 93) | | | | |
|---|---|---|---|---|---|---|---|---|---|---|
| Days | At Risk | Occurrences of Events | Cumulative Occurrences of Events | Conditional Probability of Events (SE) | Survival | At Risk | Occurrences of Events | Cumulative Occurrences of Events | Conditional Probability of Events (SE) | Survival |
| [0-28) | 107 | 13 | 13 | 0.12 (0.03) | 1.0000 | 93 | 11 | 11 | 0.12 (0.03) | 1.0000 |
| [28-56) | 93 | 16 | 29 | 0.17 (0.04) | 0.8779 | 81 | 3 | 14 | 0.04 (0.02) | 0.8817 |
| [56-84) | 77 | 7 | 36 | 0.09 (0.03) | 0.7269 | 77 | 1 | 15 | 0.01 (0.01) | 0.8491 |
| [84-140) | 69 | 5 | 41 | 0.07 (0.03) | 0.6608 | 75 | 3 | 18 | 0.04 (0.02) | 0.8380 |
| [140-168) | 61 | 4 | 45 | 0.07 (0.03) | 0.6129 | 68 | 1 | 19 | 0.01 (0.01) | 0.8042 |
| >=168 | 27 | 0 | 45 | 0.00 (0.00) | 0.5724 | 32 | 0 | 19 | 0.00 (0.00) | 0.7924 |

Harzard Ratio: 0.441
95% CI: (0.258, 0.754)
p-value: 0.0028

TABLE 3

Time to Onset of Breakthrough HE Episode by Prior Lactulose Use

| | Placebo (N = 142) | | | | | 550 mg Rifaximin BID (N = 123) | | | | |
|---|---|---|---|---|---|---|---|---|---|---|
| Days | At Risk | Occurrences of Events | Cumulative Occurrences of Events | Conditional Probability of Events (SE) | Survival | At Risk | Occurrences of Events | Cumulative Occurrences of Events | Conditional Probability of Events (SE) | Survival |
| [0-28) | 141 | 19 | 19 | 0.13 (0.03) | 1.0000 | 123 | 12 | 12 | 0.10 (0.03) | 1.0000 |
| [28-56) | 121 | 21 | 40 | 0.17 (0.03) | 0.8652 | 110 | 4 | 16 | 0.04 (0.02) | 0.9024 |
| [56-84) | 100 | 13 | 53 | 0.13 (0.03) | 0.7151 | 104 | 5 | 21 | 0.05 (0.02) | 0.8696 |
| [84-140) | 86 | 10 | 63 | 0.12 (0.03) | 0.6221 | 97 | 7 | 28 | 0.07 (0.03) | 0.8278 |
| [140-168) | 73 | 5 | 68 | 0.07 (0.03) | 0.5498 | 84 | 1 | 29 | 0.01 (0.01) | 0.7678 |
| >=168 | 33 | 0 | 68 | 0.00 (0.00) | 0.5121 | 39 | 0 | 29 | 0.00 (0.00) | 0.7586 |

Harzard Ratio: 0.424
95% CI: (0.274, 0.655)
p-value: 0.0001

TABLE 4

Time to Onset of First HE-Related Hospitalization

| | Placebo (N = 159) | | | | | 550 mg Rifaximin BID (N = 140) | | | | |
|---|---|---|---|---|---|---|---|---|---|---|
| Days | At Risk | Occurrences of Events | Cumulative Occurrences of Events | Conditional Probability of Events (SE) | Survival | At Risk | Occurrences of Events | Cumulative Occurrences of Events | Conditional Probability of Events (SE) | Survival |
| [0-28) | 154 | 11 | 11 | 0.07 (0.02) | 1.0000 | 138 | 6 | 6 | 0.04 (0.02) | 1.0000 |
| [28-56) | 121 | 14 | 25 | 0.11 (0.03) | 0.9286 | 125 | 4 | 10 | 0.03 (0.02) | 0.9564 |
| [56-84) | 106 | 7 | 32 | 0.07 (0.02) | 0.8293 | 113 | 5 | 15 | 0.04 (0.02) | 0.9258 |
| [84-140) | 86 | 8 | 40 | 0.09 (0.03) | 0.7743 | 100 | 5 | 20 | 0.05 (0.02) | 0.6848 |
| [140-168) | 66 | 2 | 42 | 0.03 (0.02) | 0.7023 | 86 | 3 | 23 | 0.04 (0.02) | 0.8403 |
| >=168 | 30 | 0 | 42 | 0.00 (0.00) | 0.6810 | 39 | 0 | 23 | 0.00 (0.00) | 0.8108 |

Harzard Ratio: 0.521
95% CI: (0.313, 0.868)
p-value: 0.0107

TABLE 5

Time to Any Increase from Baseline in Conn Score

| | Placebo (N = 159) | | | | | 550 mg Rifaximin BID (N = 140) | | | | |
|---|---|---|---|---|---|---|---|---|---|---|
| Days | At Risk | Occurrences of Events | Cumulative Occurrences of Events | Conditional Probability of Events (SE) | Survival | At Risk | Occurrences of Events | Cumulative Occurrences of Events | Conditional Probability of Events (SE) | Survival |
| [0-28) | 156 | 26 | 26 | 0.17 (0.03) | 1.0000 | 139 | 17 | 17 | 0.12 (0.03) | 1.0000 |
| [28-56) | 125 | 21 | 47 | 0.17 (0.03) | 0.8333 | 119 | 5 | 22 | 0.04 (0.02) | 0.8777 |
| [56-84) | 100 | 15 | 62 | 0.15 (0.04) | 0.6928 | 109 | 9 | 31 | 0.08 (0.03) | 0.8407 |
| [84-140) | 80 | 10 | 72 | 0.13 (0.04) | 0.5883 | 94 | 5 | 36 | 0.05 (0.02) | 0.7713 |
| [140-168) | 62 | 5 | 77 | 0.08 (0.03) | 0.5143 | 79 | 0 | 36 | 0.00 (0.00) | 0.7302 |
| >=168 | 27 | 0 | 77 | 0.00 (0.00) | 0.4729 | 37 | 1 | 37 | 0.03 (0.03) | 0.7302 |
| Harzard Ratio: | | | | | | 0.463 | | | | |
| 95% CI: | | | | | | (0.312, 0.685) | | | | |
| p-value: | | | | | | <.0001 | | | | |

TABLE 6

Time to Onset of Breakthrough HE Episode by Baseline MELD Score Level

| | Placebo (N = 44) | | | | | 550 mg Rifaximin BID (N = 34) | | | | |
|---|---|---|---|---|---|---|---|---|---|---|
| Days | At Risk | Occurrences of Events | Cumulative Occurrences of Events | Conditional Probability of Events (SE) | Survival | At Risk | Occurrences of Events | Cumulative Occurrences of Events | Conditional Probability of Events (SE) | Survival |
| [0-28) | 44 | 2 | 2 | 0.05 (0.03) | 1.0000 | 34 | 1 | 1 | 0.03 (0.03) | 1.0000 |
| [28-56) | 42 | 4 | 6 | 0.10 (0.05) | 0.9545 | 33 | 0 | 1 | 0.00 (0.00) | 0.9706 |
| [56-84) | 38 | 1 | 7 | 0.03 (0.03) | 0.8636 | 32 | 0 | 1 | 0.00 (0.00) | 0.9706 |
| [84-140) | 37 | 3 | 10 | 0.08 (0.04) | 0.8409 | 32 | 1 | 2 | 0.03 (0.03) | 0.9706 |
| [140-168) | 33 | 4 | 14 | 0.12 (0.06) | 0.7727 | 28 | 0 | 2 | 0.00 (0.00) | 0.9398 |
| >=168 | 14 | 0 | 14 | 0.00 (0.00) | 0.6791 | 13 | 0 | 2 | 0.00 (0.00) | 0.9398 |
| Harzard Ratio: | | | | | | 0.171 | | | | |
| 95% CI: | | | | | | (0.039, 0.754) | | | | |
| p-value: | | | | | | 0.0197 | | | | |

TABLE 7

Time to Onset of Breakthrough HE Episode by Baseline MELD Score Level

| | Placebo (N = 86) | | | | | 550 mg Rifaximin BID (N = 85) | | | | |
|---|---|---|---|---|---|---|---|---|---|---|
| Days | At Risk | Occurrences of Events | Cumulative Occurrences of Events | Conditional Probability of Events (SE) | Survival | At Risk | Occurrences of Events | Cumulative Occurrences of Events | Conditional Probability of Events (SE) | Survival |
| [0-28) | 86 | 15 | 15 | 0.18 (0.04) | 1.0000 | 85 | 8 | 8 | 0.09 (0.03) | 1.0000 |
| [28-56) | 70 | 13 | 28 | 0.19 (0.05) | 0.8246 | 77 | 2 | 10 | 0.03 (0.02) | 0.9059 |
| [56-84) | 56 | 11 | 39 | 0.20 (0.05) | 0.6703 | 73 | 3 | 13 | 0.04 (0.02) | 0.8822 |
| [84-140) | 45 | 7 | 46 | 0.16 (0.05) | 0.5387 | 68 | 6 | 19 | 0.09 (0.03) | 0.8459 |
| [140-168) | 36 | 2 | 48 | 0.06 (0.04) | 0.4539 | 58 | 1 | 20 | 0.02 (0.02) | 0.7713 |
| >=168 | 16 | 0 | 48 | 0.00 (0.00) | 0.4284 | 27 | 0 | 20 | 0.00 (0.00) | 0.7580 |
| Harzard Ratio: | | | | | | 0.329 | | | | |
| 95% CI: | | | | | | (0.195, 0.556) | | | | |
| p-value: | | | | | | <.0001 | | | | |

TABLE 8

Time to Onset of Breakthrough HE Episode by Baseline MELD Score Level

| | Placebo (N = 14) | | | | | 550 mg Rifaximin BID (N =11) | | | | |
|---|---|---|---|---|---|---|---|---|---|---|
| Days | At Risk | Occurrences of Events | Cumulative Occurrences of Events | Conditional Probability of Events (SE) | Survival | At Risk | Occurrences of Events | Cumulative Occurrences of Events | Conditional Probability of Events (SE) | Survival |
| [0-28) | 14 | 3 | 3 | 0.21 (0.11) | 1.0000 | 11 | 1 | 1 | 0.09 (0.09) | 1.0000 |
| [28-56) | 11 | 4 | 7 | 0.36 (0.15) | 0.7857 | 10 | 0 | 1 | 0.00 (0.00) | 0.9091 |
| [56-84) | 7 | 2 | 9 | 0.29 (0.17) | 0.5000 | 10 | 3 | 4 | 0.30 (0.14) | 0.9091 |
| [84-140) | 5 | 0 | 9 | 0.00 (0.00) | 0.3571 | 7 | 0 | 4 | 0.00 (0.00) | 0.6364 |
| [140-168) | 4 | 0 | 9 | 0.00 (0.00) | 0.3571 | 7 | 0 | 4 | 0.00 (0.00) | 0.6364 |
| >=168 | 2 | 0 | 9 | 0.00 (0.00) | 0.3571 | 3 | 0 | 4 | 0.00 (0.00) | 0.6364 |
| Harzard Ratio: | | | | | | 0.403 | | | | |
| 95% CI: | | | | | | (0.123, 1.313) | | | | |
| p-value: | | | | | | 0.1315 | | | | |

TABLE 9

Time to Onset of Breakthrough HE Episode by Prior Lactulose Use

| | Placebo (N = 134) | | | | | 550 mg Rifaximin BID (N = 127) | | | | |
|---|---|---|---|---|---|---|---|---|---|---|
| Days | At Risk | Occurrences of Events | Cumulative Occurrences of Events | Conditional Probability of Events (SE) | Survival | At Risk | Occurrences of Events | Cumulative Occurrences of Events | Conditional Probability of Events (SE) | Survival |
| [0-28) | 134 | 18 | 18 | 0.13 (0.03) | 1.0000 | 127 | 12 | 12 | 0.09 (0.03) | 1.0000 |
| [28-56) | 115 | 20 | 38 | 0.17 (0.04) | 0.8652 | 114 | 4 | 16 | 0.04 (0.02) | 0.9055 |
| [56-84) | 95 | 14 | 52 | 0.15 (0.04) | 0.7147 | 108 | 6 | 22 | 0.06 (0.02) | 0.8737 |
| [84-140) | 80 | 9 | 61 | 0.11 (0.04) | 0.6094 | 100 | 6 | 28 | 0.06 (0.02) | 0.8252 |
| [140-168) | 68 | 5 | 66 | 0.07 (0.03) | 0.5408 | 88 | 1 | 29 | 0.01 (0.01) | 0.7754 |
| >=168 | 31 | 0 | 66 | 0.00 (0.00) | 0.5011 | 41 | 0 | 29 | 0.00 (0.00) | 0.7666 |
| Harzard Ratio: | | | | | | 0.399 | | | | |
| 95% CI: | | | | | | (0.258, 0.618) | | | | |
| p-value: | | | | | | <.0001 | | | | |

TABLE 10

Time to Any Increase from Baseline in Asterixis Grade

| | Placebo (N = 159) | | | | | 550 mg Rifaximin BID (N = 140) | | | | |
|---|---|---|---|---|---|---|---|---|---|---|
| Days | At Risk | Occurrences of Events | Cumulative Occurrences of Events | Conditional Probability of Events (SE) | Survival | At Risk | Occurrences of Events | Cumulative Occurrences of Events | Conditional Probability of Events (SE) | Survival |
| [0-28) | 154 | 20 | 20 | 0.13 (0.03) | 1.0000 | 137 | 13 | 13 | 0.10 (0.03) | 1.0000 |
| [28-56) | 120 | 15 | 35 | 0.13 (0.03) | 0.8697 | 116 | 7 | 20 | 0.06 (0.02) | 0.9048 |
| [56-84) | 91 | 4 | 39 | 0.04 (0.02) | 0.7610 | 101 | 7 | 27 | 0.07 (0.03) | 0.8499 |
| [84-140) | 76 | 6 | 45 | 0.08 (0.03) | 0.7275 | 87 | 3 | 30 | 0.03 (0.02) | 0.7910 |
| [140-168) | 61 | 4 | 49 | 0.07 (0.03) | 0.6701 | 74 | 1 | 31 | 0.01 (0.01) | 0.7637 |
| >=168 | 27 | 1 | 50 | 0.04 (0.04) | 0.6262 | 34 | 1 | 32 | 0.03 (0.03) | 0.7534 |
| Harzard Ratio: | | | | | | 0.646 | | | | |
| 95% CI: | | | | | | (0.414, 1.008) | | | | |
| p-value: | | | | | | 0.0523 | | | | |

TABLE 11

Mean Change from Baseline in Blood Ammonia Concentration (μg/dL)

| Assessment Time | Placebo (N = 159) | 550 mg Rifaximin BID (N = 140) | P-value |
|---|---|---|---|
| Day 28 | | | |
| n | 126 | 121 | |
| Mean | 89.3 | 88.4 | |
| SD | 48.19 | 49.02 | |
| Median | 87.0 | 74.0 | |
| Min | 2 | 25 | |
| Max | 315 | 326 | |

TABLE 11-continued

Mean Change from Baseline in Blood Ammonia Concentration (μg/dL)

| Assessment Time | Placebo (N = 159) | 550 mg Rifaximin BID (N = 140) | P-value |
|---|---|---|---|
| Change from Baseline to Day 28 | | | |
| n | 117 | 117 | 0.6268 |
| Mean | −1.1 | −2.1 | |
| SD | 48.32 | 44.37 | |
| Median | 1.0 | −2.0 | |
| Min | −252 | −164 | |
| Max | 133 | 176 | |

TABLE 12

Mean Change from Baseline in Critical Flicker Frequency Test (Hz)

| Assessment Time | Placebo (N = 159) | 550 mg Rifaximin BID (N = 140) | P-value |
|---|---|---|---|
| Day 140 | | | |
| n | 70 | 87 | |
| Mean | 38.7 | 38.7 | |
| SD | 5.47 | 4.76 | |
| Median | 38.8 | 38.9 | |
| Min | 26 | 27 | |
| Max | 50 | 49 | |
| Change from Baseline to Day 140 | | | |
| n | 70 | 87 | 0.0266 |
| Mean | 1.1 | 1.4 | |
| SD | 4.10 | 4.84 | |
| Median | 0.9 | 1.5 | |
| Min | −12 | −15 | |
| Max | 12 | 12 | |

TABLE 13

Mean Change from Baseline in Critical Flicker Frequency Test (Hz)

| Assessment Time | Placebo (N = 159) | 550 mg Rifaximin BID (N = 140) | P-value |
|---|---|---|---|
| EOT | | | |
| n | 155 | 139 | |
| Mean | 37.6 | 37.8 | |
| SD | 5.98 | 4.88 | |
| Median | 37.9 | 37.8 | |
| Min | 21 | 25 | |
| Max | 50 | 49 | |
| Change from Baseline to EOT | | | |
| n | 155 | 139 | 0.0320 |
| Mean | 0.4 | 0.9 | |
| SD | 4.70 | 4.75 | |
| Median | 0.2 | 0.1 | |
| Min | −12 | −14 | |
| Max | 16 | 11 | |

TABLE 14

Number of Subjects in Each Level of Change from Baseline in Conn Score by Treatment Group

| Assessment Time | Statistics | Placebo (N = 159) | 550 mg Rifaximin BID (N = 140) | Odds Ratio (550 mg Rifaximin BID/Placebo) | 95% CI for Odds Ratio | P-value |
|---|---|---|---|---|---|---|
| Change from Baseline to EOT | | | | | | |
| −1 | n (%) | 18 (11.5%) | 26 (18.7%) | 2.46 | (1.49, 4.09) | 0.0005 |
| 0 | n (%) | 100 (63.7%) | 101 (72.7%) | | | |
| 1 | n (%) | 29 (18.5%) | 10 (7.2%) | | | |
| 2 | n (%) | 9 (5.7%) | 2 (1.4%) | | | |
| 3 | n (%) | 1 (0.6%) | 0 | | | |
| | n | 157 | 139 | | | |
| | Mean | 0.2 | −0.1 | | | |
| | SD | 0.74 | 0.56 | | | |
| | Median | 0.0 | 0.0 | | | |
| | Min | −1 | −1 | | | |
| | Max | 3 | 2 | | | |

TABLE 15

Number of Subjects in Each Level of Change from Baseline in Asterixis Grade by Treatment Group

| Assessment Time | Statistics | Placebo (N = 159) | 550 mg Rifaximin BID (N = 140) | Odds Ratio (550 mg Rifaximin BID/Placebo) | 95% CI for Odds Ratio | P-value |
|---|---|---|---|---|---|---|
| | | Change from Baseline to EOT | | | | |
| −2 | n (%) | 1 (0.6%) | 1 (0.7%) | 1.88 | (1.10, 3.23) | 0.0207 |
| −1 | n (%) | 14 (8.9%) | 18 (12.9%) | | | |
| 0 | n (%) | 114 (72.6%) | 108 (77.7%) | | | |
| 1 | n (%) | 18 (11.5%) | 10 (7.2%) | | | |
| 2 | n (%) | 8 (5.1%) | 2 (1.4%) | | | |
| 3 | n (%) | 1 (0.6%) | 0 | | | |
| 4 | n (%) | 1 (0.6%) | 0 | | | |
| | n | 157 | 139 | | | |
| | Mean | 0.2 | 0.0 | | | |
| | SD | 0.76 | 0.54 | | | |
| | Median | 0.0 | 0.0 | | | |
| | Min | −2 | −2 | | | |
| | Max | 4 | 2 | | | |

TABLE 16

Mean Change from Baseline for Epworth Sleepiness Total Score

| Assessment Time | Placebo (N = 159) | 550 mg Rifaximin BID (N = 140) | P-value |
|---|---|---|---|
| Day 28 | | | |
| N | 91 | 87 | |
| Mean | 9.1 | 10.0 | |
| SD | 4.84 | 5.51 | |
| Median | 8.0 | 9.0 | |
| Min | 0 | 0 | |
| Max | 21 | 23 | |
| Change from Baseline to Day 28 | | | |
| N | 90 | 86 | 0.0593 |
| Mean | −1.1 | −0.2 | |
| SD | 4.79 | 3.53 | |
| Median | −1.0 | 0.0 | |
| Min | −17 | −14 | |
| Max | 14 | 7 | |

Example 3

Induction of CYP3A4 by rifaximin was observed based on decreased midazolam AUC by ~25%. A higher systemic exposure is expected in a majority of the target patient population.

When rifaximin was orally administered at high doses (1650 mg/day) for at least 7 days, the mean $C_{max}$, $AUC_{0-t}$, and $AUC_{0-\infty}$ of midazolam were reduced by <25%. Rifaximin is a potential CYP3A4 inducer, in vitro studies have shown it to have a lower induction potency than rifampin. (The estimated intestinal lumen concentration of rifaximin is approximately 5 µM. In the in vitro study, CYP3A4 activity was induced 1.7-fold and 1.8-fold at rifaximin 1 µM and 10 µM; at the same concentrations, rifampin induced CYP3A4 3.7-fold and 4-fold, respectively. Furthermore, rifaximin's gut-targeted distribution is believed to limit its CYP3A4 induction mechanism to the intestine, sparing hepatic induction as a result of low systemic exposure. That is, there is a separation of intestinal and hepatic induction for rifaximin. This is shown in studies disclosed herein in humans receiv-

TABLE 17

Time to Onset of First HE-Related Hospitalization

| | Placebo (N = 159) | | | | | 550 mg Rifaximin BID (N = 140) | | | | |
|---|---|---|---|---|---|---|---|---|---|---|
| Days | At Risk | Occurrences of Events | Cumulative Occurrences of Events | Conditional Probability of Events (SE) | Survival | At Risk | Occurrences of Events | Cumulative Occurrences of Events | Conditional Probability of Events (SE) | Survival |
| [0-28) | 155 | 11 | 11 | 0.07 (0.02) | 1.0000 | 139 | 4 | 4 | 0.03 (0.01) | 1.0000 |
| [28-56) | 132 | 12 | 23 | 0.09 (0.03) | 0.9288 | 130 | 4 | 8 | 0.03 (0.02) | 0.9711 |
| [56-84) | 108 | 7 | 30 | 0.06 (0.02) | 0.8440 | 119 | 4 | 12 | 0.03 (0.02) | 0.9411 |
| [84-140) | 88 | 4 | 34 | 0.05 (0.02) | 0.7893 | 106 | 5 | 17 | 0.05 (0.02) | 0.9094 |
| [140-168) | 72 | 2 | 36 | 0.03 (0.02) | 0.7535 | 92 | 2 | 19 | 0.02 (0.02) | 0.8665 |
| >=168 | 34 | 0 | 36 | 0.00 (0.00) | 0.7325 | 43 | 0 | 19 | 0.00 (0.00) | 0.8475 |
| Harzard ratio: | | | | | | 0.500 | | | | |
| 95% CI: | | | | | | (0.287, 0.873) | | | | |
| p-value | | | | | | 0.0129 | | | | | ing rifaximin, as supported by the absence of induction when either intravenous or oral midazolam was administered following rifaximin 200 mg TID for up to 7.

Without wishing to be bound by any particular scientific theory, it is thought that any risk of hepatic CYP3A4 induction likely is further mitigated in hepatically impaired patients, for whom significant fractions of portal blood flow are shunted around the liver;[3] therefore, their increased systemic exposure should be accompanied by a proportional decrease in exposure to hepatocytes and the patients should incur no net increase in risk of hepatic CYP3A4 induction.

Example 4

Two clinical drug-drug interaction studies were conducted with the rifaximin 200 mg tablet and one drug-drug interaction study with the 550 mg tablet. Two studies using midazolam, a known substrate for CYP3A4, and 1 study using an oral contraceptive containing ethinyl estradiol and norgestimate were conducted to assess the effect of rifaximin on the pharmacokinetics of these drugs. Based on the results of these studies and in vitro induction and inhibition studies using human liver fractions, no clinically relevant drug interactions are anticipated with XIFAXAN.

Although in vitro studies demonstrated the potential of rifaximin to interact with cytochrome P450 3A4 (CYP3A4), a clinical drug-drug interaction study demonstrated that rifaximin did not significantly affect the pharmacokinetics of midazolam either presystemically or systemically. An additional clinical drug-drug interaction study showed no effect of rifaximin on the presystemic metabolism of an oral contraceptive containing ethinyl estradiol and norgestimate. Therefore, clinical interactions with drugs metabolized by human cytochrome P450 isoenzymes are not expected.

Two studies have been performed to evaluate the potential for drug interactions with midazolam. The first was an open-label, randomized, crossover, drug-interaction trial designed to assess the effect of rifaximin 200 mg administered orally (PO) every 8 hours (Q8H) for 3 days and every 8 hours for 7 days, on the pharmacokinetics of a single dose of either midazolam 2 mg intravenous (IV) or midazolam 6 mg PO. No significant difference was observed in the metrics of systemic exposure or elimination of IV or PO midazolam or its major metabolite, 1'-hydroxymidazolam, between midazolam alone or together with rifaximin. Therefore, rifaximin was not shown to significantly affect intestinal or hepatic CYP3A4 activity.

The second study, an open-label, drug-interaction study examined the effect of rifaximin, 550 mg three times daily, on orally administered (PO) midazolam 2 mg when dosed for 7 and 14 consecutive days. In this study rifaximin was shown to be a weak inducer of CYP3A4; given the low systemic exposure of rifaximin, this interaction is believed to be limited to the gastrointestinal tract. This induction is both dose- and dosing-duration dependent. When rifaximin was orally administered at high doses (1650 mg/day) for at least 7 days, the mean $C_{max}$, $AUC_{0-t}$, and $AUC_{0-\infty}$ of midazolam were reduced by <25%.

In vitro hERG potency and in vitro protein binding of rifaximin. In the in vitro hERG studies, rifaximin concentrations up to 300 µM failed to achieve 50% inhibition of the hERG potassium current. Due to rifaximin precipitation at 300 µM, the $IC_{50}$ was estimated to be greater than 100 µM. In fact, 50% inhibition could not be achieved; at 100 µM, mean inhibition was 34.5%. The highest $C_{max}$ observed in a hepatically impaired patient in a study was 52.2 ng/mL (0.0664 µM); the highest free fraction observed in a subset of plasma samples from patients enrolled in this study was 44.7%. Using these numbers, the highest anticipated free plasma exposure would be 0.03 µM, which represents a reduction of ≥3000-fold in comparison with the highest concentration at which rifaximin could be tested in the hERG experiments. This safety margin greatly exceeds the 30-fold separation between hERG $IC_{50}$ and unbound $C_{max}$ that is commonly associated with minimization of risk of clinical QT prolongation.[4]

Example 5

An efficacy parameter for a first study was the occurrence of an episode of breakthrough overt HE during treatment. Breakthrough overt HE episodes were measured by using the Conn score (or West Haven grade), and the asterixis grade. A breakthrough overt HE episode, as defined for the first study, was a marked, clinically significant deterioration in neurological function that can result in a deleterious effect on self care, and lead to hospitalization. The efficacy endpoint, time to first breakthrough overt HE episode, showed a highly significant protective effect of rifaximin (p<0.0001 for between-group difference in relative risk). Rifaximin treatment resulted in a 57.9% reduction, when compared with placebo, in the risk of experiencing breakthrough overt HE during the 6-month treatment period.

In addition, this study also showed that the time to first breakthrough overt HE also showed a highly significant protective effect of rifaximin when analyzed in separate geographic regions, North America versus Russia.

Rifaximin treatment results in fewer overt HE episodes that may otherwise incapacitate the patient, may alleviate the burden on family members who are required to care for the patient, and reduces the burden of hospitalization in this patient population and the healthcare system.

In a second study, similar results were shown, for example, the second study with respect to time to first breakthrough overt HE episode: the Kaplan-Meier estimates of time to first breakthrough overt HE episode were similar between the rifaximin group in the first study and new rifaximin subjects in this second study. Also, similar proportions of subjects had breakthrough overt HE in the rifaximin group of the first study (22%, 31 of 140 [rifaximin group]) and in the new rifaximin group of the second study (27.6%, 54 of 196).

Additionally, when the first study placebo subjects crossed over to rifaximin therapy by entering the second study, a protective effect of rifaximin was observed: the first study a 70% reduction in risk of experiencing breakthrough overt HE during rifaximin treatment in the second study when compared with their prior placebo experience in the first study. This reduction took place in spite of the aging and presumably progressing nature of the population with chronic liver disease.

The second study also showed that the protective effect of rifaximin was durable: the estimate of time-to-first breakthrough HE demonstrated long-term maintenance of remission from breakthrough HE when rifaximin subjects in remission after participation in the first study were followed in the second study (up to 680 days of rifaximin therapy; median exposure durations were 168 days in the first study and 253 days in the second study). The incidence of breakthrough HE episode for these rifaximin subjects relative to the first study placebo was lower, an indication of fewer breakthrough HE episodes with rifaximin treatment.

A critical flicker frequency (CFF) assessment, a recognized quantitative measure of CNS dysfunction, was an efficacy endpoint in the first study. CFF tests utilize the correlation between cerebral processing of oscillatory visual stimuli and CNS impairment due to increased HE severity.[10,11,12,13] This test identifies a frequency at which a flickering light is perceived as steady. A decline in this frequency has been associated with increasing severity of HE. Likewise, elevation in blood ammonia, another endpoint in the first study, is a quantitative assessment associated with the CNS effects underlying overt HE.

Comparisons of changes from baseline to end of study in CFF results and in venous ammonia levels showed statistically significant, greater improvement over the course of the study in the rifaximin group when compared to placebo (p=0.0320 for CFF changes and p=0.0391 for venous ammonia changes). In the first study, a correlation between CFF results and breakthrough overt HE (primary efficacy measure) was noted. Venous ammonia levels were found to be correlated to the occurrence of breakthrough overt HE in the first study.

Results for other efficacy endpoints also demonstrated protective effects of rifaximin. In particular, the other efficacy endpoint of time to first HE-related hospitalization showed a reduction in risk for rifaximin subjects.

In the first study, the analysis of time to first HE-related hospitalization (e.g., hospitalization directly resulting from HE or hospitalization complicated by HE) demonstrated that the reduction in risk of hospitalization due to HE was 50% in the rifaximin group, when compared with placebo, during the 6-month treatment period. The HE-related hospitalization rate was 0.38 event/person exposure years (PEY), rifaximin versus 0.78 event/PEY, placebo after normalization to exposure.

In the first study, the risk of HE-caused hospitalization (e.g., hospitalization directly resulting from HE only) was reduced by 56% in the rifaximin group when compared with placebo. The HE-caused hospitalization rate was 0.30 events/PEY in the rifaximin group versus 0.72 event/PEY in the placebo group.

In the first study, the risk of all-cause hospitalization rate was reduced by 30% in the rifaximin group when compared to placebo. The all-cause hospitalization rate was 0.92 events/PEY in the rifaximin group versus 1.31 event/PEY in the placebo group.

In the second study, the low HE-caused hospitalization rate was maintained at rates consistent with those in the first study: HE-caused hospitalization rate was 0.29 event/PEY and all cause hospitalization in the second study was 0.66 event/PEY. The consistently low HE-related/HE-caused hospitalization rate in rifaximin-treated subjects in the first study and in the second study was at least partly a result of maintaining remission from demonstrated HE in subjects with end-stage liver disease.

Hepatic encephalopathy is associated with a low quality of life compared to age-matched patients without HE. Patients with HE experience symptoms including fatigue, daytime sleepiness, and lack of awareness (Conn score 1); and confusion and disorientation (Conn score 2) that significantly interfere with day-to-day function and decreased ability for self care. Often, this lack of self care can lead to improper nutrition and non-adherence to therapy and can further escalate into more severe symptoms such as increased somnolence, gross disorientation and stupor, which require hospitalization. Rifaximin treatment protects against HE related/caused hospitalization, thereby improving the functional status for the patient and benefiting his/her caregiver; and reducing the economic cost related to liver cirrhosis and associated HE.

There are limited treatment options in the United States for patients with recurrent HE. Neomycin sulfate is only approved for the adjunctive therapy in hepatic coma. Conventional therapy aims to lower the production and absorption of ammonia. Nonabsorbable disaccharides, eg, lactulose or lactitol, are typically used as first-line therapy for HE. There is evidence that nonabsorbable disaccharides lower plasma levels of ammonia by changing nitrogen metabolism in colonic flora and increasing fecal excretion of nitrogen. Broadspectrum, GI-active antibiotics including neomycin, metronidazole, vancomycin, and paromomycin have been used with or without lactulose. These antibiotics appear to act indirectly by inhibiting the splitting of urea by deaminating bacteria, thus reducing the production of ammonia and other potential toxins. Current guidelines recommend (not FDA approved) antibiotic therapy with neomycin or metronidazole as an alternative to treatment with nonabsorbable disaccharides.

Common side effects of nonabsorbable disaccharide (e.g., lactulose) therapy include an unpleasant taste that can hinder treatment compliance, a dosing schedule that is linked to bowel habits, and GI side effects such as bloating, abdominal cramps, and diarrhea. Diarrhea resulting in dehydration has been reported with the use of lactulose, a significant consequence for patients with HE as electrolyte abnormalities can worsen HE and lead to renal dysfunction.

The use of systemically absorbed antibiotics such as neomycin in the treatment of HE is hampered by ototoxicity and nephrotoxicity associated with long-term use. The incidence of aminoglycoside-induced nephrotoxicity is substantially greater in patients with advanced liver disease than in patients without liver disease. The frequency of aminoglycoside-induced nephrotoxicity in the general population is 3% to 11%. Leitman reported that nephrotoxicity occurred in 73% of patients with liver disease versus 34% of patients without liver disease who received aminoglycosides by intravenous administration during hospitalization; and Cabrera reported that renal tubular damage or functional renal impairment was observed in 60% of aminoglycoside-treated cirrhotic patients (intravenous administration during hospitalization). Additionally, a high mortality rate and sustained renal damage were noted in cirrhotic patients who developed aminoglycoside-induced renal tubular damage. Therefore, aminoglycosides are now widely considered as contraindicated in patients with advanced liver disease.

Rifaximin is an attractive therapy for the treatment of patients with HE because of its demonstrated effectiveness, favorable safety profile, and because of disadvantages of systemic aminoglycosides and nonabsorbable disaccharides. Rifaximin has a broad spectrum of in vitro antibacterial activity against both Gram-positive and Gram-negative bacteria and against aerobic and anaerobic isolates.

Since rifaximin is poorly absorbed after oral administration, the drug is selectively active in the gastrointestinal tract. Additionally, there is a low risk of drug-drug interactions with the use of rifaximin Rifaximin has a lower rate of fecal eradication of pathogens compared with other commonly used antibacterial drugs and causes minimal alterations in gut flora suggesting that rifaximin has a different mechanism of action than other commonly used drugs in enteric bacterial infection, such as the fluoroquinolones. The risk of the development of antibiotic resistance is low during chronic treatment with rifaximin when compared to other systemic antibiotics such as neomycin, possibly because resistance is mediated by a mutation in host cell DNA and is not plasmid based.

In a retrospective chart review, the numbers and durations of hospitalizations due to HE, the total cost of therapy, and HE endpoints (asterixis grade, Conn score) were found to be dramatically reduced when compared to lactulose treatment in patients with HE who received lactulose daily for 6 months and then received rifaximin daily for 6 months.

The first study was designed to overcome the limitations of previous studies reported in the literature (e.g., heterogeneous subject populations, small population size, short durations, and insufficient endpoints for mental status).

First, treatment duration was increased to 6 months. This longer duration was planned to allow for a greater number of subjects to experience an HE episode than if the study was limited to ≤6 weeks. Also, the longer treatment duration provided an opportunity to evaluate the long-term safety of rifaximin in subjects with chronic hepatic cirrhosis and associated recurrent, overt, episodic HE. The study investigated consequences of HE with respect to patient care and economic cost by measuring hospitalizations due to HE episodes as a key secondary efficacy endpoint.

To evaluate overt HE episodes by using clinically relevant criteria in the first study and study the second study, mental status impairment was measured by using Conn score (West Haven criteria) and the severity of neuromotor abnormalities was measured by asterixis grade. The Conn score ranges from Stage 0 (lack of detectable changes in personality) to Stage 4 (coma, decerebrate posturing, dilated pupils). The Conn score is the recommended and widely used gold standard for grading the severity of impaired mental status in overt HE. Asterixis (flapping tremor) is a neuromotor symptom of overt HE that increases in severity with worsening neurological impairment.

The control group for the first study received matched placebo tablets in parallel with rifaximin treatments in the active group. The second study was an ongoing open-label, treatment-extension study to evaluate the long-term safety of rifaximin 550 mg BID in subjects with a history of recurrent, episodic, overt HE. In addition to safety measurements, Conn scores and asterixis grades were assessed during the course of the study to measure the protective effect of rifaximin against breakthrough overt HE during treatment for up to approximately 1 year in subjects who completed up to 6 months of rifaximin treatment in the first study and then entered the second study; in subjects who received placebo in the first study and crossed over to rifaximin treatment in the second study; and in patients with a history of HE who entered the second study as new subjects.

The dosage regimen used (550 mg BID) was based on past clinical experience with rifaximin in patients with HE and other subject populations. In several previous studies, rifaximin was safe and effective in subjects with HE at a dose of 1200 mg per day with or without concomitant lactulose. In a 6-month study of rifaximin versus neomycin (14 days on-treatment and 14 days off-treatment per month), rifaximin 1200 mg/day and neomycin (3 g/day) had comparable efficacy in patients with HE. Aminoglycoside antibiotics are contraindicated in patients with advanced liver disease because of the risk of nephrotoxicity.

An efficacy endpoint was the time to first breakthrough overt HE episode. A breakthrough overt HE episode was defined as an increase of Conn score to Grade ≥2 (e.g., 0 or 1 to ≥2) or an increase in Conn and asterixis score of 1 grade each for those subjects who entered the study with a Conn score of 0. Time to breakthrough overt HE episode was the duration from time of first dose of study drug to the first breakthrough overt HE episode. Subjects who completed the study and did not experience a breakthrough overt HE episode were censored at the time of their 6-month visit. Subjects who terminated early for reasons other than breakthrough overt HE were contacted at 6 months from randomization to determine if subjects had experienced a breakthrough overt HE episode or other outcome (e.g., mortality status); and, if the subject had no breakthrough overt HE event prior to contact, he/she was censored at the time of contact. Therefore, complete capture was achieved for breakthrough overt HE episodes up to 6 months postrandomization. Subjects in the study had ≥2 episodes of overt HE equivalent to Conn score ≥2 within 6 months prior to screening (i.e., subjects had documented recurrent, overt HE). At the baseline assessment, subjects were in remission with a Conn score of 0 or 1. A breakthrough overt HE episode, as defined above, was a marked deterioration in neurological function.

Other efficacy endpoints in the first study included, for example:
1. Time to first HE-related hospitalization;
2. Time to any increase from baseline in Conn score (mental state grade);
3. Time to any increase from baseline in asterixis grade;
4. Mean change from baseline in fatigue domain scores on the CLDQ at end of treatment; and
5. Mean change from baseline in venous ammonia concentration at end of treatment.

Presented herein are the results of the first study and second study. The first study was a double-blind, randomized, placebo-controlled study evaluating the efficacy and safety of rifaximin 550 mg BID as compared to placebo. Subjects in remission from demonstrated recurrent, overt, episodic HE associated with chronic, hepatic cirrhosis were randomized on Day 0 (Visit 2) according to a 1:1 ratio to receive rifaximin 550 mg BID or placebo for 6 months. The primary efficacy endpoint was the time to breakthrough overt HE. Breakthrough overt HE was defined as an increase of Conn score to Grade ≥2 (e.g., 0 or 1 to ≥2) or an increase in Conn and asterixis score of 1 grade each for those subjects who entered the study with a Conn score of 0. Subjects discontinued from the study at the time of breakthrough overt HE episode. After participation in the first study, subjects had the option to enroll in the open-label, treatment-extension study (the second study).

A total of 299 subjects were randomized to receive rifaximin (140 subjects) or placebo (159 subjects). All randomized subjects received at least 1 dose of study drug. A total of 251 (84%) (116 [rifaximin], 135 [placebo]) subjects completed the study as specified in the protocol (e.g., completed 6 months of treatment or withdrew from the study at the time of breakthrough overt HE).

Subjects in the study had ≥2 episodes of overt HE equivalent to Conn score ≥2 within 6 months prior to screening (e.g., subjects had recurrent, overt HE). At the baseline assessment, subjects were in remission with a Conn score of 0 or 1. A breakthrough overt HE episode was a marked deterioration in neurological function. Breakthrough overt HE episodes were experienced by 31 of 140 subjects in the rifaximin group and by 73 of 159 subjects in the placebo group during the 6-month treatment period (up to Day 170). Comparison of Kaplan-Meier estimates of time to breakthrough overt HE between groups showed a protective effect of rifaximin (p<0.0001). These data show that rifaximin treatment resulted in a 57.9% reduction, when compared with placebo, in the risk of experiencing breakthrough overt HE. Rifaximin treatment results in fewer overt HE episodes that may otherwise incapacitate the patient, may alleviate the burden on family members who are required to care for the patient, and reduces the burden of hospitalization in this patient population and the healthcare system.

The following prognostic factors were found to be predictors of breakthrough overt HE episodes: baseline age (p=0.0160), MELD score (p=0.0003), duration of current verified remission (p=0.1089), and number of prior HE episodes (p=0.0022). These data show that rifaximin treatment, resulted in a 60% reduction, when compared with placebo, in the risk of experiencing a breakthrough overt HE episode during the course of this study (p<0.0001).

Time to first HE-related hospitalization; and the frequencies of HE-related and all-cause hospitalizations Hepatic encephalopathy-related hospitalizations (hospitalization directly resulting from HE or hospitalization complicated by HE) were reported for 19 of 140 subjects and 36 of 159 subjects in the rifaximin and placebo groups, respectively. Rifaximin had a protective effect against HE-related hospitalization during the 6-month treatment period. Subjects in the rifaximin group had a 50% reduction in the risk of hospitalization due to HE during the 6-month treatment period when compared with placebo. The HE-related hospitalization rate was 0.38 events/PEY in the rifaximin group versus 0.78 event/PEY in the placebo group.

Hepatic encephalopathy-caused hospitalizations (hospitalization directly resulting from HE only) were reported for 15 of 140 subjects and 33 of 159 subjects in the rifaximin and placebo groups, respectively. Rifaximin had a significant protective effect against HE-caused hospitalization during the 6-month treatment period; hazard ratio in the rifaximin group relative to placebo was 0.438 (95% CI: 0.238 to 0.807) (p=0.0064) for the risk of HE-caused hospitalization. Subjects in the rifaximin group had a 56% reduction in the risk of hospitalization due to HE during the 6-month treatment period when compared with placebo. The HE-caused hospitalization rate was 0.30 events/PEY in the rifaximin group versus 0.72 event/PEY in the placebo group.

All-cause hospitalization was also lower in the rifaximin group (46 of 140) than in the placebo group (60 of 159) (30% reduction in the rifaximin group compared with placebo). The all cause hospitalization rate, after normalizing for subject exposure, was 0.90 events/PEY in the rifaximin group and 1.26 event/PEY in the placebo group. The HE-related hospitalization rate was 0.38 event/PEY in the rifaximin group and 0.78 event/PEY in the placebo group. Rifaximin treatment protects against HE-related hospitalization, thereby improving the quality of life for the patient and for his/her caregiver, and reducing the economic cost related to liver cirrhosis and associated HE.

Time to any increase from baseline in Conn score and time to any increase from baseline in asterixis grade Protective effects of rifaximin were observed with respect to both of these endpoints when analyzed independently; hazard ratio in the rifaximin group relative to placebo was 0.463 (95% CI: 0.312 to 0.685) (p<0.0001) for the risk of experiencing an increase in Conn score and 0.646 (95% CI: 0.414 to 1.008) (p=0.0523) for the risk of experiencing an increase in asterixis grade during the 6-month treatment period.

Changes from baseline in venous ammonia levels at end of treatment

Subjects in the rifaximin group had greater reductions in venous ammonia levels when compared to placebo-treated subjects (p=0.0391).

Venous ammonia levels, a quantitative assessment that is associated with the CNS effects underlying overt HE, was found to be highly correlated to the occurrence of breakthrough overt HE as determined by the clinical evaluation of Conn score (or a combination of Conn score and asterixis grade).

Tracking of Conn scores and asterixis grades: changes from baseline in Conn scores and asterixis grades A favorable treatment effect of rifaximin was observed, when compared with placebo, with respect to the proportions of subjects who had changes of −1 (improvement) or 0 (no change); or 1, 2, or 3 (worsening) in Conn score from baseline to end of treatment (last postbaseline assessment or assessment at time of breakthrough HE). In the rifaximin group compared to placebo, higher proportions of subjects experienced Conn score changes of −1 or no change (77.1% versus 53.9%) and lower proportions of subjects had Conn score changes of 1, 2, 3, or 4. Thus, treatment with rifaximin was more effective than placebo in the prevention of worsening of Conn score (2.46 times versus placebo, p=<0.0001).

For changes from baseline to end of treatment in asterixis grade, significantly higher proportions of subjects in the rifaximin group versus the placebo group had changes from baseline in asterixis grades of −2, −1, and 0 (88.5% versus 77.0%), and significantly lower proportions of subjects had changes of 1, 2, 3, or 4 (11.6% versus 23.2%). Thus, treatment with rifaximin was more effective than placebo in the prevention of worsening of asterixis grade (1.92 times versus placebo, p=0.0262).

Changes from Baseline in CFF Results

Increases in CFF results represent improvement in neurological function in patients with HE.[10,11] Subjects in the rifaximin group had significantly greater increases in CFF results from baseline to end of treatment when compared with placebo. Mean changes (±standard deviation [SD]) in CFF results were 0.945 (±4.75) in the rifaximin group versus 0.355 (±4.70) in the placebo group (p=0.0320 for between-group difference). Similar to venous ammonia levels, CFF was shown to be highly predictive of breakthrough HE.

Median exposure to study drug was 168 days (range: 10 to 178) in the rifaximin group and 110 days (range: 6 to 176) in the placebo group. A total of 64 subjects (33 [rifaximin] and 31 [placebo]) received treatment for 141 to 168 days and 98 subjects (57 [rifaximin] and 41 [placebo]) received treatment for >168 days. Duration of exposure results are consistent with the finding that lower proportions of subjects in the rifaximin group than in the placebo group experienced breakthrough overt HE resulting in study discontinuation (per protocol, subjects discontinued from the study after breakthrough overt HE).

The percentages of subjects who had treatment-emergent AEs, severe TEAEs, drug-related TEAEs, treatment-emergent SAEs, TEAEs resulting discontinuation, and who died were similar between placebo and rifaximin groups. A total of 79.9% of subjects (239 of 299) experienced TEAEs during the course of the study. The most common TEAEs (e.g., in ≥10% of total subjects [combined placebo plus rifaximin]) experienced by subjects were the following: diarrhea (10.7% [rifaximin] versus 13.2% [placebo]), nausea (14.3% versus 13.2%), peripheral edema (15% versus 8.2%), fatigue (12.1% versus 11.3%), dizziness (12.9% versus 8.2%), ascites (11.4% versus 9.4%), and headache (10% versus 10.7%).

The second study is an ongoing open-label, treatment-extension study evaluating the long-term safety of rifaximin 550 mg BID in subjects with a history of recurrent, overt, episodic HE. All eligible subjects had a history of overt HE episodes with a documented severity equivalent to Conn score ≥2 within 12 months prior to screening (≥1 qualifying episode was required), a Conn score of ≤2 at the baseline assessment, and either participated in the first study or were new subjects. Unlike the first study, subjects were not required to withdraw from the study after experiencing a breakthrough overt HE episode.

A total of 267 subjects were enrolled and 208 were active at the time of the interim clinical cutoff. Additional data were collected for the interim report up to the time of database freeze.

Conn scores and asterixis grades were assessed during the course of the study. Therefore, it was possible to determine time to breakthrough overt HE episode for subjects who completed 6 months of rifaximin treatment in the first study and then entered the second study, subjects who received placebo in the first study and then started rifaximin in the second study, and in new subjects who started rifaximin therapy in the second study. In subjects who took rifaximin for up to 680 days (1.9 years), breakthrough overt HE episodes during the treatment period were experienced by 72 of 266 subjects (27.1%) overall: 54 of 196 subjects (27.6%) in the new rifaximin group and 18 of 70 subjects (25.7%) in the continuing rifaximin group.

Time-to-first-breakthrough HE profiles were similar between the rifaximin group in the first study and the new rifaximin group in the second study. A durable protective effect of rifaximin was observed in subjects who received rifaximin starting in the first study and continuing in the second study (median exposures to rifaximin were 168 days in the first study and 253 days in the second study)

A total of 133 of 266 subjects were hospitalized for any cause: 98 in the new rifaximin group, and 35 in the continuing rifaximin group. Normalizing for subject exposure, this represents a hospitalization rate of 0.60 event/PEY. A total of 59 were hospitalized due HE episodes (e.g., HE-caused). Normalizing for subject exposure, this represents an HE-caused hospitalization rate of 0.29 event/PEY. The low HE-caused hospitalization rate was consistent between rifaximin therapy in the second study (0.29 event/PEY) and in the first study rifaximin (0.30 event/PEY) at least partly as a result of maintaining remission from demonstrated HE in subjects with end-stage liver disease. Tracking of Conn scores and asterixis grades: changes from baseline in Conn scores and asterixis grades Conn scores were generally maintained or improved with rifaximin use up to 18 months. At the last visit, 70.7% of subjects (188 of 266 subjects) had no change and 20.3% (54 of 266) had improvements in Conn scores compared with baseline, indicating that mental status was maintained or improved in the majority of subjects (91%) over the treatment period. Of the 84 subjects (70 new rifaximin and 14 continuing rifaximin) who entered the study with Conn scores of 1, 2, or 3 (e.g., those subjects for whom measurable improvement was possible), 54 subjects (54/84=64.3%) showed a 1-grade (47 subjects; 56.0%) or 2-grade (7 subjects; 8.3%) improvement from baseline at the last visit recorded for the interim analysis. All subjects were capable of worsening over time, and 24/266 subjects (9.0%) did so by 1 or 2 grades.

Like Conn scores, asterixis grades were generally maintained or improved with rifaximin use up to 18 months. At the last visit, 77.1% of subjects (205 of 266 subjects) had no change and 16.2% (43 of 266) had improvements in asterixis scores compared with baseline, indicating that neuromotor symptoms associated with increasing neurological impairment were maintained in 83.3% of subjects over the treatment period. Of the 67 subjects (55 new rifaximin and 12 continuing rifaximin) who entered the study with asterixis scores of 1, 2, or 3 (e.g., those subjects for whom improvement was possible), 43 subjects (43/67=64.2%) showed a 1-(34 subjects; 50.7%), 2-(4 subjects; 6.0%), or 3-grade (5 subjects; 7.5%) improvement from baseline at the last visit recorded for this interim analysis. All subjects were capable of worsening over time, and 18/266 subjects (6.8%) did so by 1, 2, or 4 grades; the incidence of worsening asterixis grades were similar between the new (12/196 subjects; 6.1%) and continuing (6/70 subjects; 8.6%) rifaximin groups.

Median exposures in study the second study were 253 days (range: 7 to 680) in the new rifaximin group (subjects who received placebo in the first study or subjects who did not participate in the first study), 265.5 days (range: 10 to 673) in the continuing rifaximin group (subjects who received rifaximin in the first study and the second study), and 255 days (range: 7 to 680) in the all rifaximin group (all subjects who received rifaximin in the second study). At the time of this interim analysis, most subjects had received rifaximin for 6 to <9 months (21.4%) or 9 to <12 months (32.3%).

At the time of this interim analysis, TEAEs were reported in 230 subjects (86.5%). The most common TEAEs (e.g., in ≥10% of total subjects) experienced by subjects were the following: peripheral edema (15.8%); urinary tract infection and nausea (12.8% each); and abdominal pain and ascites (10.5% each). Note that signs and symptoms associated with HE were not considered AEs unless they met the definition of an SAE, so the number of subject with HE counted in efficacy analysis (72 subjects; 27.1%) is higher than that counted for the safety analyses (57 subjects; 21.4%).

Most TEAEs were mild or moderate in intensity, with 40.2% of subjects experiencing at least 1 TEAE that was judged by the investigator to be severe. The incidence of TEAEs considered related to study drug was comparable between the new rifaximin group (7.7%) and the continuing rifaximin group (7.1%). Treatment-emergent SAEs were experienced by 47.4% of subjects.

FIG. 1 illustrates Kaplan-Meier estimates of time to first breakthrough overt HE episode by treatment group in the ITT population. Table 18 presents Kaplan-Meier estimates of the proportions of subjects who experienced breakthrough overt HE over the course of the Treatment Period and results of statistical analyses. Subjects who completed the study and did not experience a breakthrough overt HE event were censored at the time of their 6-month visit. Subjects who terminated early for reasons other than breakthrough overt HE (eg, liver transplant, AE, subject request) were contacted at 6 months from date of randomization to determine if subjects had experienced a breakthrough overt HE episode or other outcome (e.g., mortality status). Subjects without breakthrough overt HE were censored at the time of contact or death, whichever was earlier. Therefore, complete capture was achieved for breakthrough overt HE episodes up to 6 months.

TABLE 18

The First Study: Kaplan-Meier Estimates and Statistical Analyses of Time to First Breakthrough Overt HE (up to 6 Months of Treatment, Day 170) (ITT Population)

| Treatment interval (days) | Placebo (N = 159) | | | | | Rifaximin (N = 140) | | | | |
|---|---|---|---|---|---|---|---|---|---|---|
| | At risk[a] | Number of events[b] | Cumulative number of events | Event probability (SE)[c] | Probability of no breakthrough overt HE[d] | At risk[a] | Number of events[b] | Cumulative number of events | Event probability (SE)[c] | Probability of no breakthrough overt HE[d] |
| 0 to <28 | 158 | 20 | 20 | 0.13 (0.03) | 1.0000 | 140 | 13 | 13 | 0.09 (0.02) | 1.0000 |
| 28 to <56 | 137 | 23 | 43 | 0.17 (0.03) | 0.8734 | 126 | 4 | 17 | 0.03 (0.02) | 0.9071 |
| 56 to <84 | 113 | 14 | 57 | 0.12 (0.03) | 0.7262 | 120 | 6 | 23 | 0.05 (0.02) | 0.8783 |
| 84 to <140 | 98 | 10 | 67 | 0.10 (0.03) | 0.6363 | 112 | 7 | 30 | 0.06 (0.02) | 0.8344 |
| 140 to <168 | 84 | 6 | 73 | 0.07 (0.03) | 0.5713 | 98 | 1 | 31 | 0.01 (0.01) | 0.7820 |
| ≥168 | 38 | 0 | 73 | 0 | 0.5305 | 46 | 0 | 31 | 0 | 0.7740 |
| Hazard ratio: | | | | | | 0.421[e] | | | | |
| 95% CI: | | | | | | (0.276, 0.641) | | | | |
| p-value | | | | | | <0.0001 | | | | |

[a] Number of subjects at risk during the treatment interval, estimated using the life table method. Assuming that censored cases were at risk for half of the interval, they only counted for half in figuring the number at risk.
[b] Number of events occurring during the treatment interval.
[c] Estimate of the probability of experiencing breakthrough overt HE during the treatment interval. Standard error (SE) estimated by using Greenwood's formula.
[d] Estimate of the probability of no breakthrough overt HE until at least the beginning of the next treatment interval.
[e] Hazard ratio estimate (hazard of breakthrough overt HE in the rifaximin group compared with the placebo group) determined from the Cox proportional hazards model. P-value based on the Score statistic.

Breakthrough overt HE episodes were experienced by 31 of 140 subjects in the rifaximin group and by 73 of 159 subjects in the placebo group during the 6-month period since randomization (up to Day 170). Comparison of Kaplan-Meier estimates of time to breakthrough overt HE between groups showed a protective effect of rifaximin (p<0.0001). These data show that rifaximin treatment resulted in a 57.9% reduction, when compared with placebo, in the risk of experiencing breakthrough overt HE during the course of this study. Rifaximin treatment results in fewer overt HE episodes that may otherwise incapacitate the patient, may alleviate the burden on family members who are required to care for the patient, and reduces the burden of hospitalization in this patient population and the healthcare system.

To investigate the potential effect of prognostic factors on breakthrough overt HE episode, the following prognostic factors were examined:
Sex (male vs. female);
Age;
Race (white vs. non-white);
Analysis Region (North American vs. Russia);
MELD Level;
Conn Score (0 vs. 1);
Diabetes at Baseline (Yes vs. No);
Duration of current verified remission; and
Number of HE Episodes within the past 6 months prior to randomization.

Strong independent predictors of breakthrough overt HE episodes were the baseline age (p=0.0160), MELD score (p=0.0003), duration of current verified remission (p=0.1089), and number of prior HE episodes (p=0.0022).

These data show that rifaximin treatment, after adjusting for significant prognostic factors, resulted in a 60% reduction, when compared with placebo, in the risk of experiencing a breakthrough overt HE episode during the course of this study. The most influential prognostic factors were age (p=0.0315) and baseline MELD score (p=0.0003).

The results indicate that the highly significant protective effect of rifaximin (p<0.0001) against breakthrough overt HE episodes was maintained in the presence of statistically significant competing factors.

In the second study, median exposures were 253 days (range: 7 to 680) in the new rifaximin group (subjects who received placebo in the first study or subjects who did not participate in the first study), 265.5 days (range: 10 to 673) in the continuing rifaximin group (subjects who received rifaximin in the first study and the second study), and 255 days (range: 7 to 680) in the all rifaximin group (all subjects who received rifaximin in the second study In subjects who took rifaximin for up to 680 days (1.9 years), breakthrough overt HE episodes during the treatment period were experienced by 72 of 266 subjects (27.1%) overall: 54 of 196 subjects (27.6%) in the new rifaximin group and 18 of 70 subjects (25.7%) in the continuing rifaximin group. FIG. 2 compares subjects who participated in the double-blind, randomized the first study with new rifaximin subjects in the long-term, open-label study, the second study.

The Kaplan-Meier estimates of time to first breakthrough overt HE episode were similar between the rifaximin group in the first study and new rifaximin subjects in the second study. Also, similar proportions of subjects had breakthrough overt HE in the rifaximin group of the first study (22%, 31 of 140 [rifaximin group]) and in the new rifaximin group of the second study (27.6%, 54 of 196). Adjusted for exposure, rates of breakthrough HE episodes were 0.62 events/PEY in the rifaximin group from the first study compared to 0.38 events/PEY for new rifaximin subjects in the second study. These data demonstrate that protection against breakthrough overt HE in subjects who received rifaximin was consistent between the 2 studies.

Figure 7:
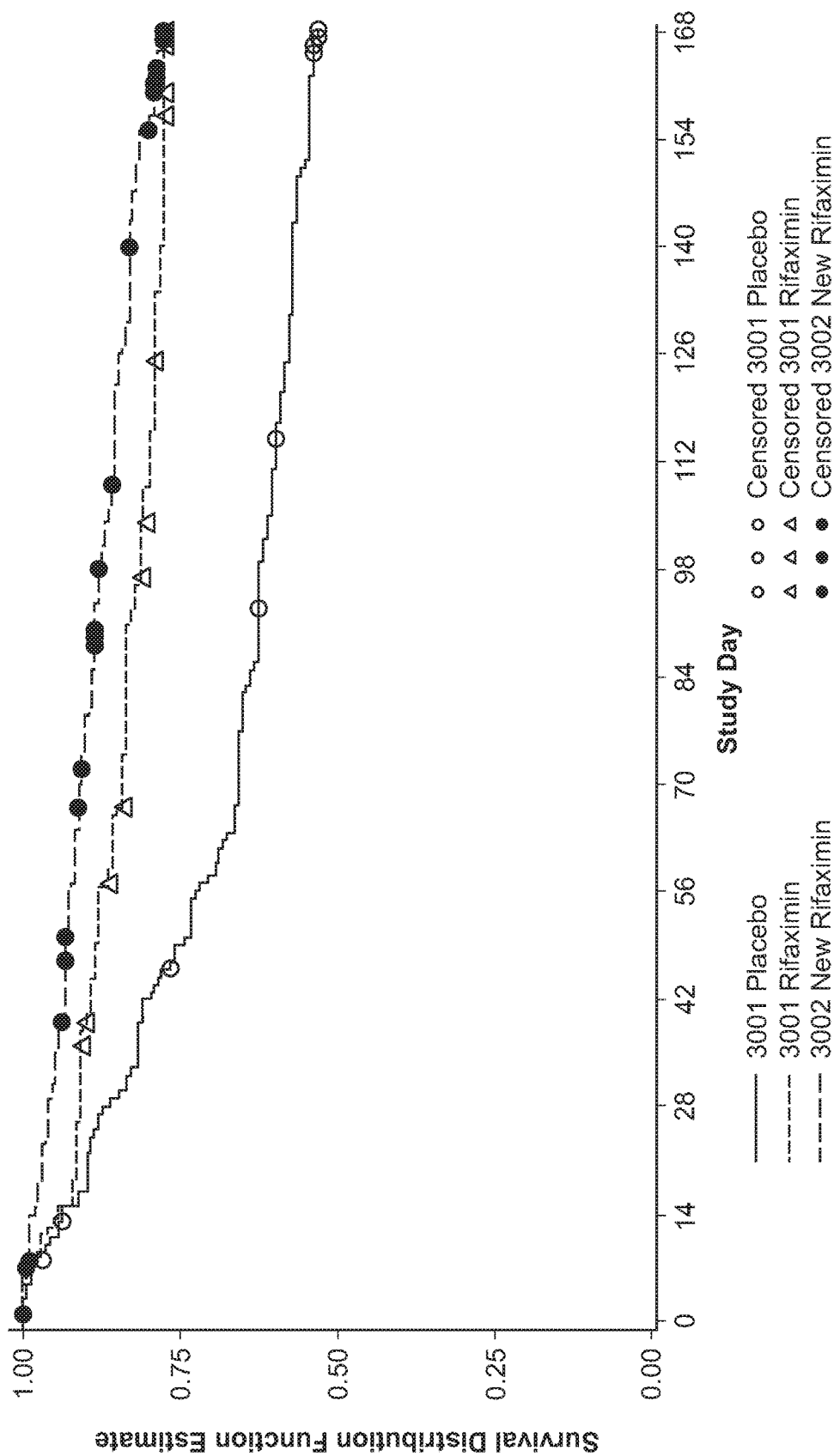
FIG. 7 is a comparison of time to first breakthrough over the episode in the first study (rifaximin versus placebo groups) and the second study (new to rifaximin group).

Note for FIG. 7, the survival distribution estimate on y-axis represents the proportion of subjects without breakthrough overt HE.

The first study data on time to first breakthrough overt HE episode are shown for the rifaximin group (small dashes) and the placebo group (straight line). The second study data on time to first breakthrough overt HE episode in the new rifaximin group are shown in large dashes.

Figure 8:
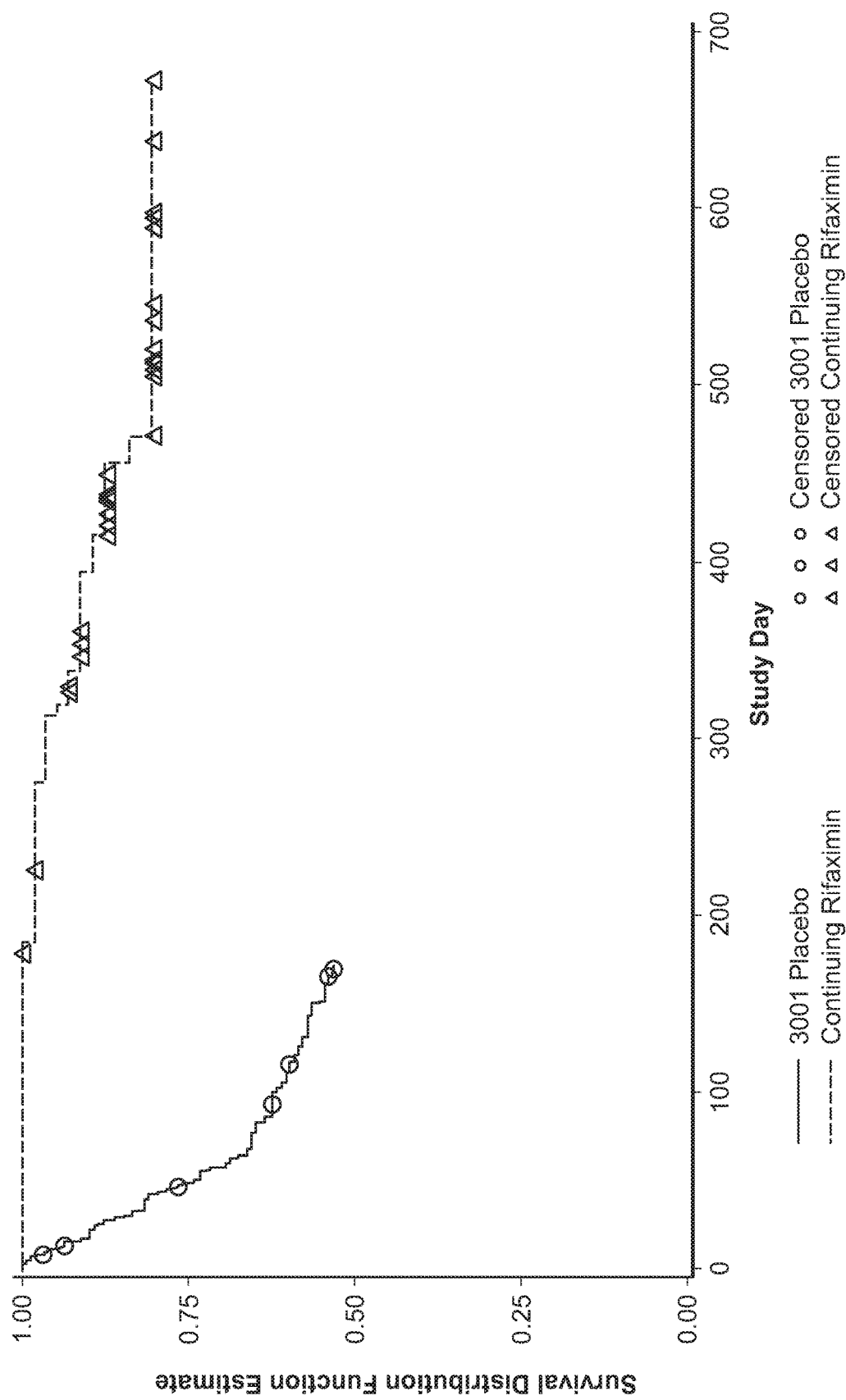
FIG. 8 depicts a comparison of time to first breakthrough over the episode during placebo experience (the first study) and after crossover to rifaximin experience (the second study) among the first study placebo subjects who started rifaximin in the second study.

In FIG. 8, the first study placebo subjects were followed after they crossed over to rifaximin therapy in the second study. Breakthrough overt HE was experienced by 15 of 82 during rifaximin treatment versus 39 of 82 during placebo treatment. A striking protective effect of rifaximin was observed in the comparison of Kaplan-Meier estimates of time to first breakthrough overt HE between placebo experience in the first study and rifaximin experience in the second study. The hazard ratio of rifaximin to placebo was 0.302 (95% CI: 0.166 to 0.549, p<0.0001 for between group difference in relative risk). This result represents 70% reduction in risk of experiencing breakthrough overt HE during rifaximin treatment in the second study when compared with their prior placebo experience in the first study.

Note for FIG. 8, the survival distribution estimate on y-axis represents the proportion of subjects without breakthrough overt HE. the first study data on time to first breakthrough overt HE episode are shown in the left panel for the placebo group. The right panel shows time to first breakthrough overt HE in the second study among the first study placebo subjects (n=82) who crossed over to rifaximin therapy in the second study. The vertical line between the left and right panels marks the end of the double-blind study and start of the open-label study.

Figure 9:
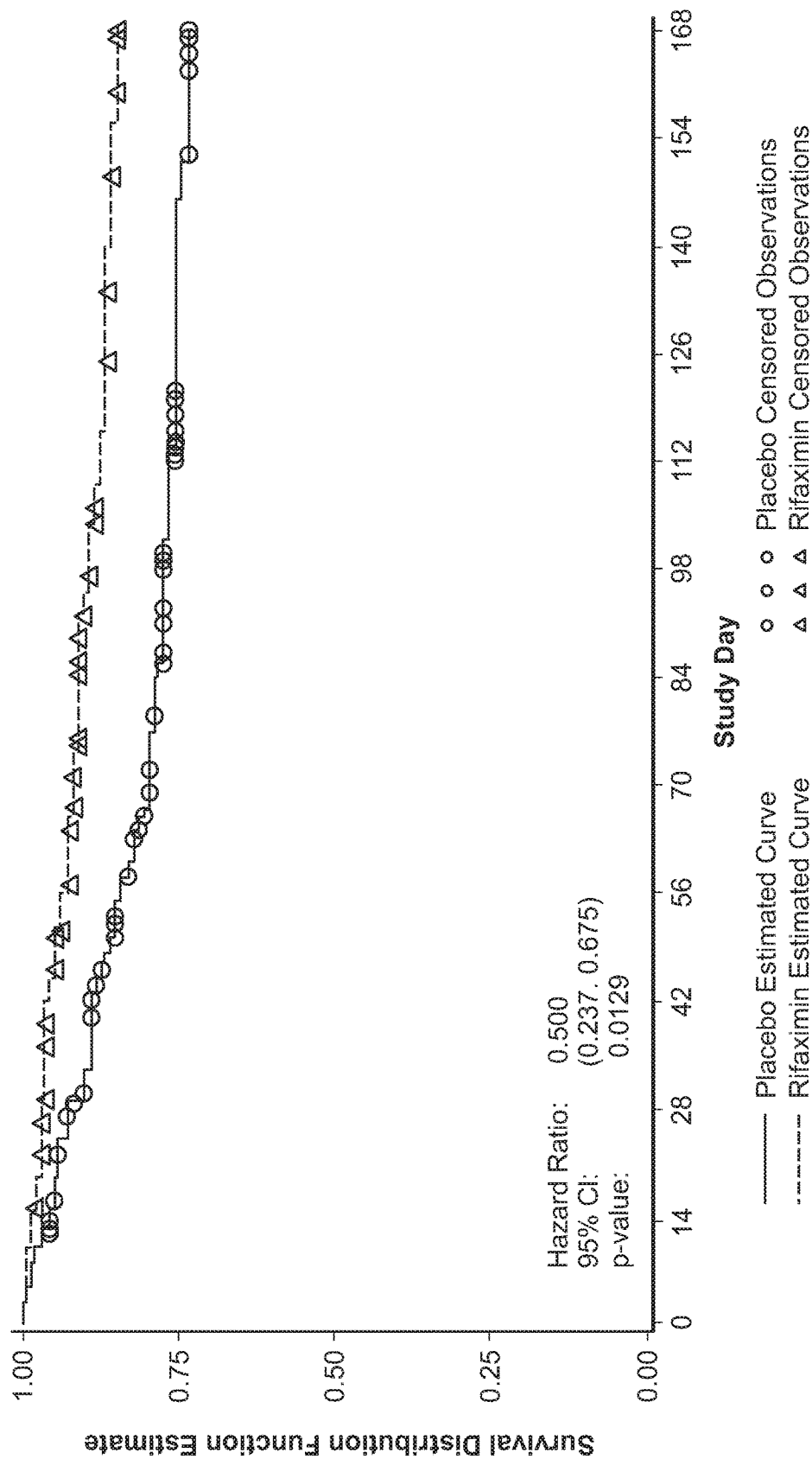
FIG. 9 depicts the time to first he-related hospitalization (up to 6 months of treatment, day 170, in the first study).

FIG. 9 illustrates time to first HE-related hospitalization (e.g., hospitalization directly resulting from HE or hospitalization caused by HE) by treatment group in the ITT population in the first study. Table 19 presents estimates of the proportions of subjects who had their first HE-related hospitalization over the course of the Treatment Period and results of statistical analyses. Subjects who discontinued prior to hospitalization due to HE and prior to completion of the 6-month treatment period were censored at the time of discontinuation. Hepatic encephalopathy-related hospitalizations were reported for 19 of 140 subjects and 36 of 159 subjects in the rifaximin and placebo groups, respectively. Rifaximin had a protective effect against HE-related hospitalization during the 6-month treatment period; hazard ratio in the rifaximin group relative to placebo was 0.500 (95% CI: 0.287 to 0.873) (p=0.0129) for the risk of HE-related hospitalization. This hazard ratio represents a 50% reduction, when compared with placebo, in the risk of hospitalization due to HE during the 6-month treatment period. Consistent with these results, the HE-related hospitalization rate was 51% lower (0.38 event/PEY, rifaximin versus 0.78 event/PEY, placebo) in the rifaximin group in the first study, after normalization to exposure.

Note for FIG. 9, the survival distribution estimate on y-axis represents the proportion of subjects without HE-related hospitalization. Dashed line represents rifaximin group and solid line represents placebo group. Open circles and open triangles represent censored subjects. Subjects who discontinued prior to hospitalization due to HE and prior to completion of the 6-month treatment period were censored at the time of discontinuation. Hepatic encephalopathy-related hospitalization was recorded on the HE-related hospitalization CRF.

TABLE 19

The First Study: Kaplan-Meier Estimates and Statistical Analyses of Time to First HE-Related Hospitalization (up to 6 Months of Treatment, Day 170) (ITT Population)

| Treatment interval (days) | Placebo (N = 159) | | | | | Rifaximin (N = 140) | | | | |
|---|---|---|---|---|---|---|---|---|---|---|
| | At risk[a] | Number of events[b] | Cumulative number of events | Event probability (SE)[c] | Probability of no HE-related hospitalization[d] | At risk[a] | Number of events[b] | Cumulative number of events | Event probability (SE)[c] | Probability of no HE-related hospitalization[d] |
| 0 to <28 | 155 | 11 | 11 | 0.07 (0.02) | 1.0000 | 139 | 4 | 4 | 0.03 (0.01) | 1.0000 |
| 28 to <56 | 132 | 12 | 23 | 0.09 (0.03) | 0.9288 | 130 | 4 | 8 | 0.03 (0.02) | 0.9711 |
| 56 to <84 | 108 | 7 | 30 | 0.06 (0.02) | 0.8440 | 119 | 4 | 12 | 0.03 (0.02) | 0.9411 |
| 84 to <140 | 88 | 4 | 34 | 0.05 (0.02) | 0.7893 | 106 | 5 | 17 | 0.05 (0.02) | 0.9094 |
| 140 to <168 | 72 | 2 | 36 | 0.03 (0.02) | 0.7535 | 92 | 2 | 19 | 0.02 (0.02) | 0.8665 |
| ≥168 | 34 | 0 | 36 | 0 | 0.7525 | 43 | 0 | 19 | 0 | 0.8475 |

Abbreviations:
CI = confidence interval;
SE = standard error.
[a]Number of subjects at risk during the treatment interval, estimated using the life table method. Assuming that censored cases were at risk for half of the interval, they only counted for half in figuring the number at risk.
[b]Number of events occurring during the treatment interval.
[c]Estimate of the probability of experiencing HE-related hospitalization during the treatment interval. Standard error (SE) estimated by using Greenwood's formula.
[d]Estimate of the probability of no HE-related hospitalization until at least the beginning of the next treatment interval.
[e]Hazard ratio estimate (hazard of HE-related hospitalization in the rifaximin group compared with the placebo group) determined from the Cox proportional hazards model. P-value based on the Score statistic.

The effect of rifaximin therapy on HE-caused hospitalizations (e.g., hospitalization directly resulting from HE only) was also determined. FIG. 5 illustrates time to first HE-caused hospitalizations by treatment group in the first study.

Hepatic encephalopathy-caused hospitalizations were reported for 15 of 140 subjects and 33 of 159 subjects in the rifaximin and placebo groups, respectively. Rifaximin had a significant protective effect against HE-caused hospitalization during the 6-month treatment period; hazard ratio in the rifaximin group relative to placebo was 0.438 (95% CI: 0.238 to 0.807) (p=0.0064) for the risk of HE-caused hospitalization. Subjects in the rifaximin group had a 56% reduction in the risk of hospitalization due to HE during the 6-month treatment period when compared with placebo. The HE-caused hospitalization rate was 0.30 events/PEY in the rifaximin group versus 0.72 event/PEY in the placebo group.

Figure 10:
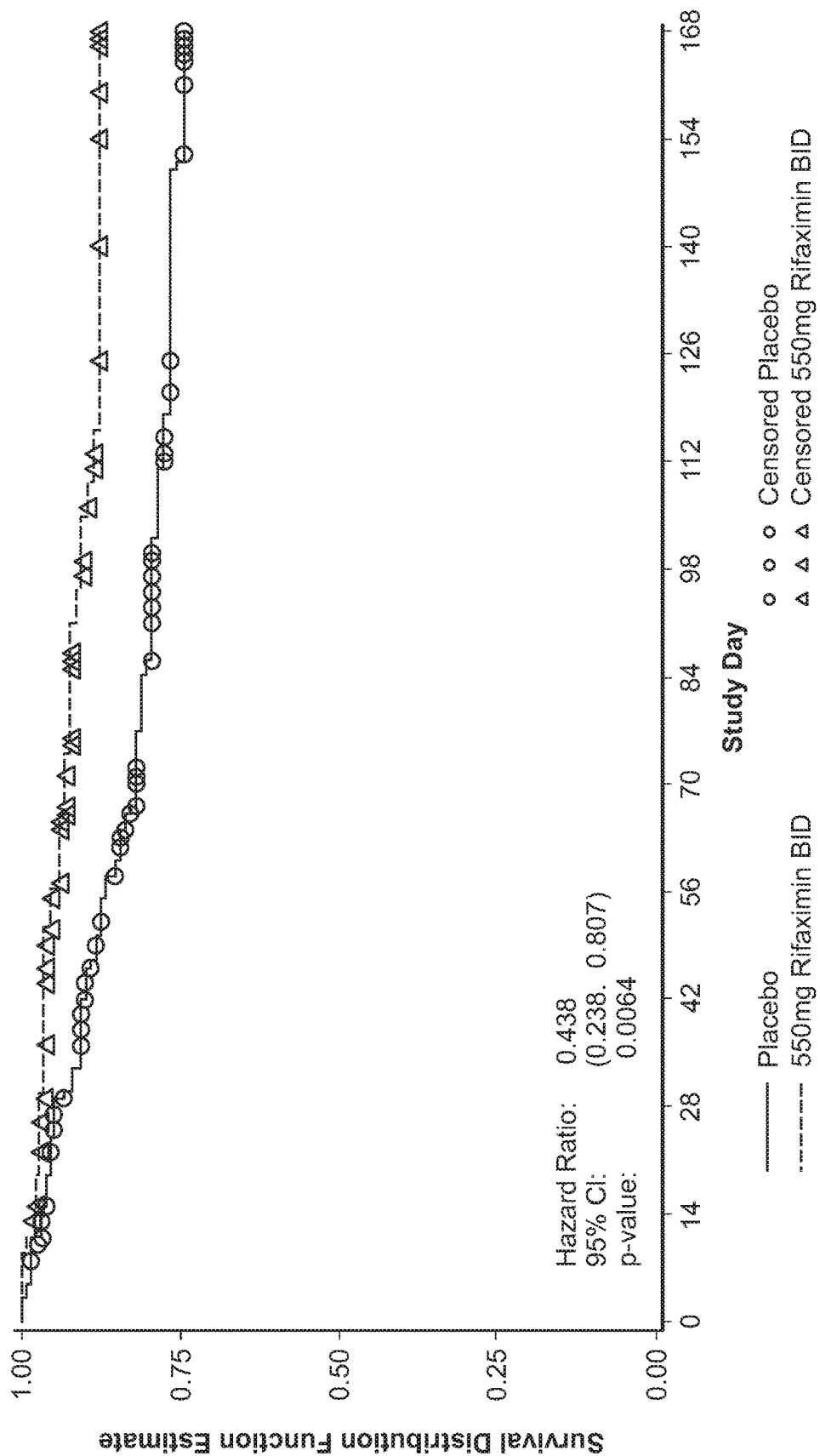
FIG. 10 depicts the time to first HE-caused hospitalization in the first study (ITT population).

Note for FIG. 10, the survival distribution estimate on y-axis represents the proportion of subjects without HE-caused hospitalizations. Dashed line represents rifaximin group and solid line represents placebo group. Open circles and open triangles represent censored subjects. Subjects who discontinued prior to hospitalization were censored at the time of discontinuation.

The effect of rifaximin therapy on all-cause hospitalizations was also determined. In the double-blind the first study, 46 of 140 rifaximin subjects and 60 of 159 placebo subjects were hospitalized due to any SAE. The risk of all-cause hospitalization was reduced by 30% in the rifaximin group when compared to placebo (p=0.0793 for between-group difference in relative risk). The all-cause hospitalization rate was 0.92 events/PEY in the rifaximin group versus 1.31 event/PEY in the placebo group. These data demonstrated that rifaximin treatment reduced the burden of HE-related/caused hospitalization when compared to placebo treatment in the first study. Also, a low HE-related/caused hospitalization rate was consistently observed during rifaximin therapy in the first study (0.38 event/PEY) and in the second study (0.29 event/PEY), at least partly as a result of maintaining remission from demonstrated HE in subjects with end-stage liver disease.

Figure 11:
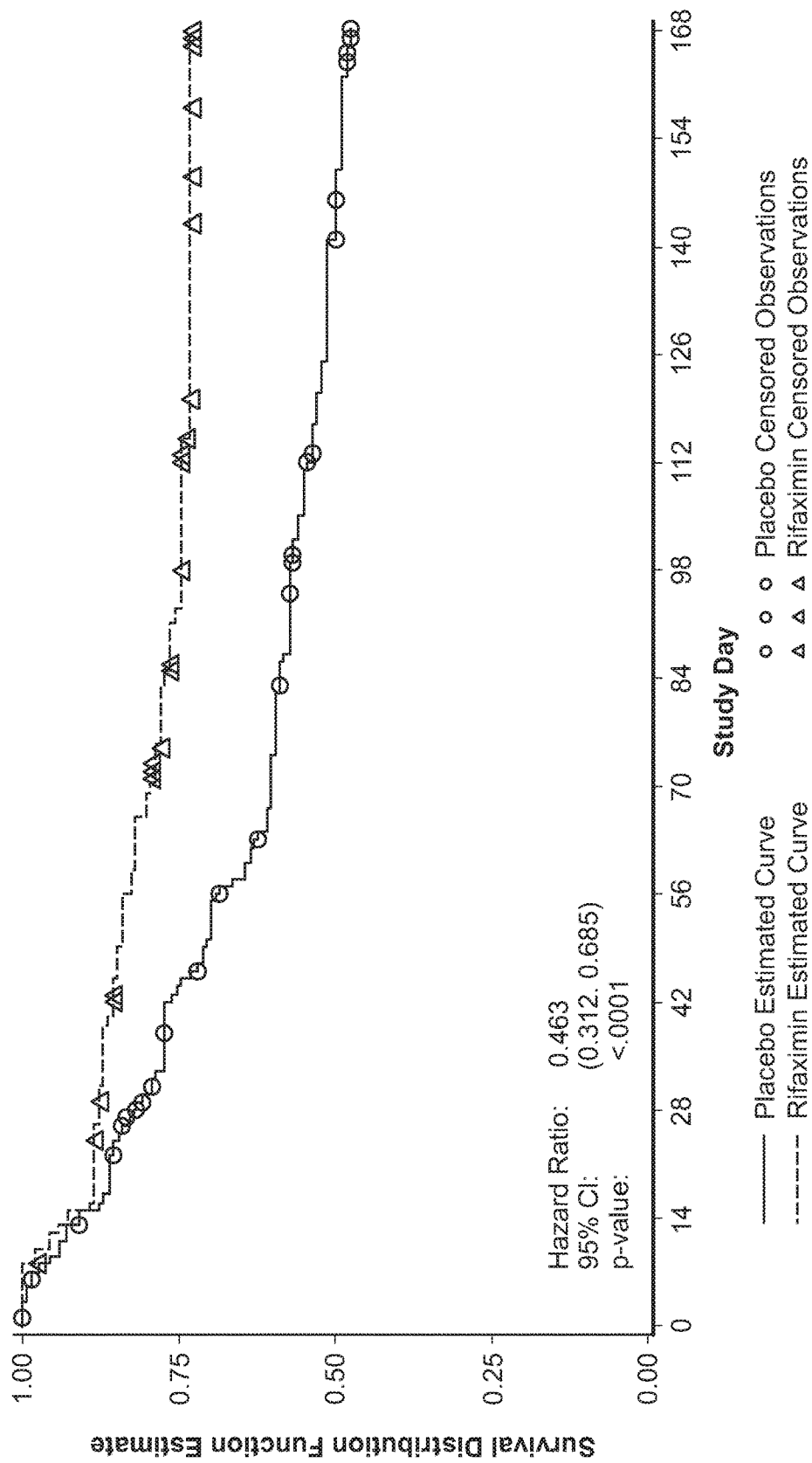
FIG. 11 depicts the time to First Increase in Conn Score (up to 6 months of treatment, day 170, the first study) (ITT Population).

FIG. 11 illustrates time to any increase from baseline in Conn score by treatment group in the ITT population. Table 20 presents estimates of the proportions of subjects who had any increase in Conn score over the course of the Treatment Period and results of statistical analyses. Subjects who discontinued prior to experiencing an increase in Conn score and prior to completion of the 6-month treatment period were censored at the time of discontinuation. By evaluating the time to any increase from baseline in Conn score, it was possible to compare the earliest worsening in mental status between subjects in the rifaximin and placebo treatment groups, even if the worsening did not reach the definition of breakthrough HE (eg, increase inConn score from 0 to 1). Increases in Conn score were reported for 37 of 140 subjects and 77 of 159 subjects in the rifaximin and placebo groups, respectively. A highly significant protective effect of rifaximin was observed; hazard ratio in the rifaximin group relative to placebo was 0.463 (95% CI: 0.312 to 0.685) (p<0.0001) for the risk of experiencing an increase in Conn score (e.g., worsening in mental status) during the 6-month treatment period.

TABLE 20

The First Study: Kaplan-Meier Estimates and Statistical Analyses of Time to First Increase in Conn Score (up to 6 Months of Treatment, Day 170) (ITT Population)

| Treatment interval (days) | Placebo (N = 159) | | | | | Rifaximin (N = 140) | | | | |
|---|---|---|---|---|---|---|---|---|---|---|
| | At risk[a] | Number of events[b] | Cumulative number of events | Event probability (SE)[c] | Probability of no increase in Conn score[d] | At risk[a] | Number of events[b] | Cumulative number of events | Event probability (SE)[c] | Probability of no increase in Conn score[d] |
| 0 to <28 | 156 | 26 | 26 | 0.07 (0.03) | 1.0000 | 139 | 17 | 17 | 0.012 (0.03) | 1.0000 |
| 28 to <56 | 125 | 21 | 47 | 0.17 (0.03) | 0.8333 | 119 | 5 | 22 | 0.04 (0.02) | 0.8777 |
| 56 to <84 | 100 | 15 | 62 | 0.15 (0.04) | 0.6928 | 109 | 9 | 31 | 0.08 (0.03) | 0.8407 |
| 84 to <140 | 80 | 10 | 72 | 0.13 (0.04) | 0.5883 | 94 | 5 | 36 | 0.05 (0.02) | 0.7713 |
| 140 to <168 | 62 | 5 | 77 | 0.08 (0.03) | 0.5143 | 79 | 0 | 36 | 0 | 0.7302 |
| ≥168 | 27 | 0 | 77 | 0 | 0.4729 | 37 | 1 | 37 | 0.03 (0.03) | 0.7302 |

Abbreviations:
CI = confidence interval;
SE = standard error.
[a]Number of subjects at risk during the treatment interval, estimated using the life table method.
[b]Number of events occurring during the treatment interval. Assuming that censored cases were at risk for half of the interval, they only counted for half in figuring the number at risk.
[c]Kaplan-Meier estimate of the probability of experiencing an increase in Conn score during the treatment interval. Standard error (SE) estimated by using Greenwood's formula.
[d]Estimate of the probability of no increase in Conn score until at least the beginning of the next treatment interval.
[e]Hazard ratio estimate (hazard of experiencing an increase in Conn score in the rifaximin group compared with the placebo group) determined from the Cox proportional hazards model. P-value based on the Score statistic.

Figure 12:
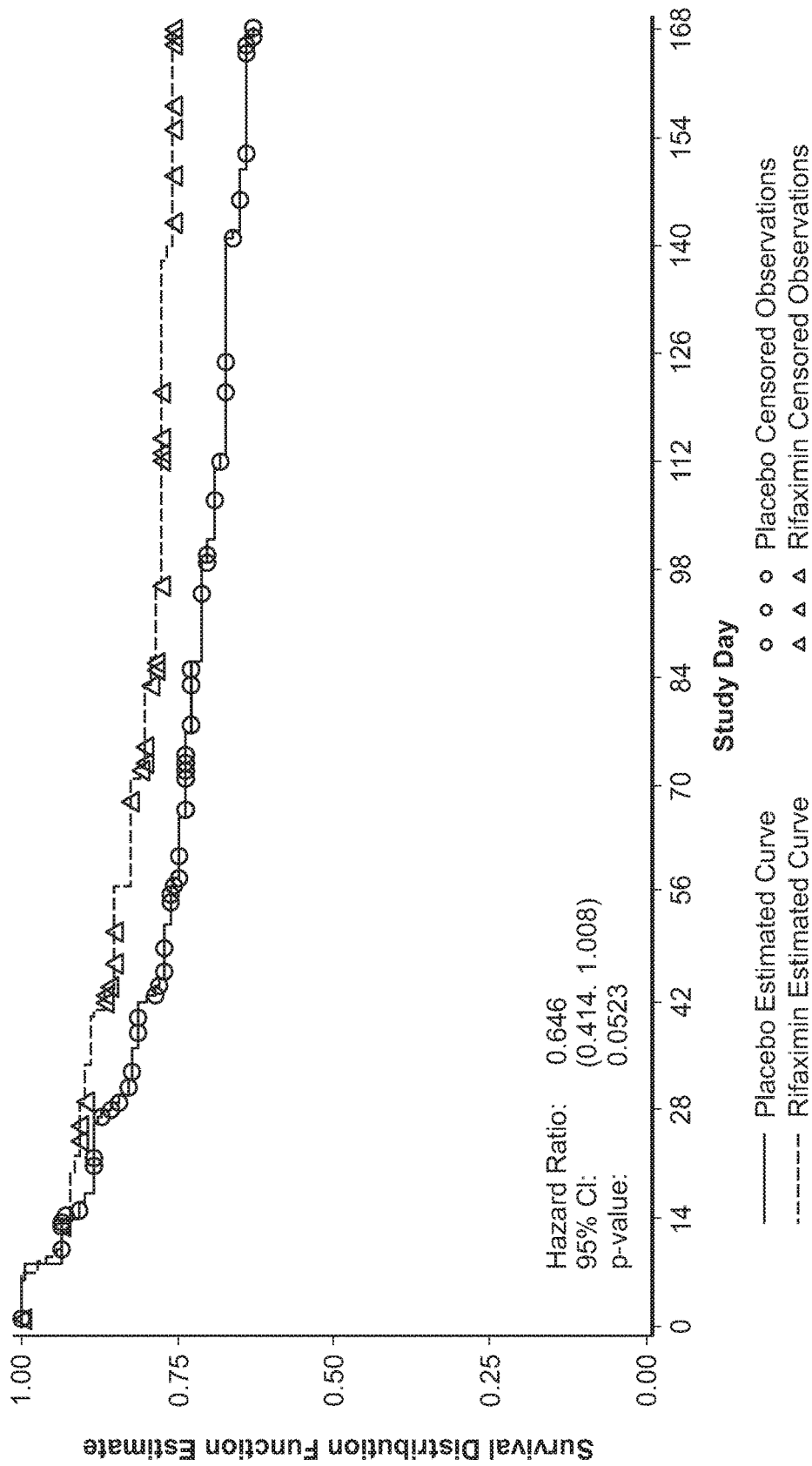
FIG. 12 depicts the time to first Increase in asterixis grade (up to 6 months of treatment, day 170, the first study) (ITT Population).

FIG. 12 illustrates time to any increase from baseline in asterixis grade by treatment group in the ITT population in the first study. Table 21 presents estimates of the proportions of subjects who had any increase in asterixis grade over the course of the Treatment Period and results of statistical analyses. Subjects who discontinued prior to experiencing an increase in asterixis grade and prior to completion of the 6-month treatment period were censored at the time of discontinuation.

By evaluating the time to any increase from baseline in asterixis grade, it was possible to compare the earliest worsening in neuromotor functioning between subjects in the rifaximin and placebo treatment groups. Increases in asterixis grade were reported for 32 of 140 subjects and 50 of 159 subjects in the rifaximin and placebo groups, respectively. A protective effect of rifaximin against an increase in asterixis grade (e.g., worsening in neuromotor functioning) was observed that showed a trend toward statistical significance; hazard ratio in the rifaximin group relative to placebo was 0.646 (95% CI: 0.414 to 1.008) (p=0.0523) for the risk of experiencing an increase in asterixis grade during the 6-month treatment period.

TABLE 21

The First Study: Kaplan-Meier Estimates and Statistical Analyses of Time to First
Increase in Asterixis Grade (up to 6 Months of Treatment, Day 170) (ITT Population)

| Treatment interval (days) | Placebo (N = 159) | | | | | Rifaximin (N = 140) | | | | |
|---|---|---|---|---|---|---|---|---|---|---|
| | At risk[a] | Number of events[b] | Cumulative number of events | Event probability (SE)[c] | Probability of no increase in asterixis grade[d] | At risk[a] | Number of events[b] | Cumulative number of events | Event probability (SE)[c] | Probability of no increase in asterixis grade[d] |
| 0 to <28 | 154 | 20 | 20 | 0.13 (0.03) | 1.0000 | 137 | 13 | 13 | 0.10 (0.03) | 1.0000 |
| 28 to <56 | 120 | 15 | 35 | 0.13 (0.03) | 0.8697 | 116 | 7 | 20 | 0.06 (0.02) | 0.9048 |
| 56 to <84 | 91 | 4 | 39 | 0.04 (0.02) | 0.7610 | 101 | 7 | 27 | 0.07 (0.03) | 0.8499 |
| 84 to <140 | 76 | 6 | 45 | 0.08 (0.03) | 0.7275 | 87 | 3 | 30 | 0.03 (0.02) | 0.7910 |
| 140 to <168 | 61 | 4 | 49 | 0.07 (0.03) | 0.6701 | 74 | 1 | 31 | 0.01 (0.01) | 0.7637 |
| ≥168 | 27 | 1 | 50 | 0.04 (0.04) | 0.6262 | 34 | 1 | 32 | 0.03 (0.03) | 0.7534 |

Abbreviations:
CI = confidence interval;
SE = standard error.
[a]Number of subjects at risk during the treatment interval, estimated using the life table method. Assuming that censored cases were at risk for half of the interval, they only counted for half in figuring the number at risk.
[b]Number of events occurring during the treatment interval.
[c]Estimate of the probability of experiencing an increase in asterixis grade during the treatment interval. Standard error (SE) estimated by using Greenwood's formula.
[d]Estimate of the probability of no increase in asterixis grade until at least the beginning of the next treatment interval.
[e]Hazard ratio estimate (hazard of experiencing an increase in asterixis grade in the rifaximin group compared with the placebo group) determined from the Cox proportional hazards model. P-value based on the Score statistic.

Subjects ranked their level of fatigue by using a 7-point scale from the worst response (1, high degree of fatigue) the best response (7, minimal fatigue) Minimal differences between placebo and rifaximin groups were observed in the changes from baseline in CLDQ fatigue scores. Mean (SD) fatigue scores were 3.34 (1.406) versus 3.28 (1.326) at baseline and 3.51 (1.529) versus 3.57 (1.527) in the placebo and rifaximin groups, respectively. Because of altered mental and neuromotor status, it was not possible for subjects to complete the CLDQ assessment during an overt HE breakthrough episode.

Table 22 summarizes changes from baseline to end of treatment in venous ammonia level by treatment group in the first study.

In the first study, venous ammonia levels were highly variable over the course of the study. However, subjects in the rifaximin group had significantly greater reductions in venous ammonia levels when compared to placebo-treated subjects (p=0.0391). Venous ammonia levels, a quantitative assessment that is associated with the CNS effects underlying overt HE, was shown to be highly predictive of the occurrence of breakthrough overt HE as determined by the clinical evaluation of Conn score (or a combination of Conn score and asterixis grade), thereby underscoring the reliability and clinical relevance of the primary efficacy measure. The significant correlation of the primary efficacy endpoint to a venous ammonia levels demonstrates the reliability and clinical relevance of the primary efficacy measure in the first study.

TABLE 22

The First Study: Mean (SD) Changes from Baseline in Venous
Ammonia Level by Treatment Group (ITT Population)

| | Placebo N = 159 (μg/dL) | Rifaximin N = 140 (μg/dL) |
|---|---|---|
| Baseline | n = 146 | n = 132 |
| Mean (SD) ammonia level | 90.3 (52.48) | 87.9 (47.76) |
| End of treatment | n = 141 | n = 132 |
| Mean (SD) ammonia level | 88.4 (45.75) | 83.9 (45.02) |
| Change than baseline to end of treatment | n = 131 | n = 125 |
| Mean (SD) change in ammonia level | −0.3 (58.13) | −5.7 (46.77) |

Note:
Baseline value was the last available value prior to first dose of study drug, and end of treatment value was the last available post-baseline value during the treatment period.

The Second Study

In the second study, Conn scores were generally maintained or improved with rifaximin use up to 18 months. At the last visit, 70.7% of subjects (188 of 266 subjects) had no change and 20.3% (54 of 266) had improvements in Conn scores compared with baseline, indicating that mental status was maintained or improved in the majority of subjects (91%) over the treatment period. Like Conn scores, asterixis grades were generally maintained or improved with rifaximin use up to 18 months. At the last visit, 77.1% of subjects (205 of 266 subjects) had no change and 16.2% (43 of 266) had improvements in asterixis scores compared with baseline, indicating that neuromotor symptoms associated with increasing neurological impairment were maintained in 83.3% of subjects over the treatment period. The last visit for the second study is the last visit recorded for the interim analysis.

Maintenance or improvement in Conn scores were observed for >85% of subjects during rifaximin treatment for up to 840 days; mean (±SD) exposure for all rifaximin experience was 273.8 (160.92) days (exposure results are present in detail in the ISS, Module 5.3.5.3.2). A total of 65.5% of subjects (220 of 337) had no change in Conn score and 21.1% (71 of 337) had improvements in Conn score from baseline to last visit. Similarly, maintenance or improvements in asterixis grades were observed for >90% of subjects during rifaximin treatment. No change from baseline in asterixis grade was reported for 75.2% of subjects (252 of 337), and 17.3% had improvements.

Of the 118 subjects who entered the study with a Conn score of ≥1, e.g., those subjects for whom improvement was possible, 62.2% (71 of 118) showed an improvement from baseline to Conn score 0 at last assessment. Also, of the 99 subjects who entered with an asterixis grade of ≥1, ie those subjects for whom improvement in asterixis grade was possible, 58.6% (58 of 99) showed improvement in asterixis grade from baseline to end of study.

Changes from baseline in Conn scores and asterixis grades to last visit were similar among new rifaximin subjects in the second study (e.g., started rifaximin in 3002), continuing rifaximin subjects (e.g., received rifaximin in the first study and in the second study), and all rifaximin experience subjects (e.g., received rifaximin in the first study or in the second study).

These results support those from the first study, in which treatment with rifaximin was significantly more effective than placebo in the prevention of worsening of Conn score (2.46 times versus placebo, p<0.0001) and in the prevention of worsening of asterixis grade (1.92 times versus placebo, p=0.0262).

Changes from Baseline in CFF Results (the First Study)

Increases in CFF results represent improvement in neurological function in patients with HE. Subjects in the rifaximin group had significantly greater increases in CFF results from baseline to end of treatment when compared with placebo (Table 23). Mean changes (±SD) in CFF results were 0.945 (±4.75) in the rifaximin group versus 0.355 (±4.70) in the placebo group (p=0.0320 for between-group difference).

Similar to the correlation for venous ammonia levels, there was a strong correlation between the quantitative assessment of CFF results and the occurrence of breakthrough overt

TABLE 23

Mean (SD) Changes from Baseline in CFF Test Results by Treatment Group (ITT Population)

|  | Placebo N = 159 (Hz) | Rifaximin N = 140 (Hz) |
| --- | --- | --- |
| Baseline | n = 159 | n = 140 |
| Mean (SD) CFF result | 37.41 (6.03) | 36.90 (5.47) |
| End of treatment | n = 155 | n = 139 |
| Mean (SD) CFF result | 37.60 (5.98) | 37.81 (4.88) |
| Change from baseline to end of treatment | n = 155 | n = 139 |
| Mean (SD) change in CFF result | 0.355 (4.70) | 0.945 (4.75) |

Note:
Baseline value was the last available value prior to first dose of study drug, and end of treatment value was the last available post-baseline value during the treatment period.

A retrospective chart review was performed for 145 patients with HE who received lactulose 30 mL twice daily for ≥6 months followed by treatment with rifaximin 400 mg 3 times/day for ≥6 months. Dramatic differences were observed in favor of rifaximin treatment. Compliance of ≥75% was significantly better during rifaximin treatment than during lactulose treatment; 92% versus 31% of patients received ≥75% of scheduled rifaximin and lactulose doses, respectively. Total number of hospitalizations, duration of hospitalizations, HE endpoints, and cost of therapy were compared between the 2 treatment regimens. Significantly fewer hospitalizations (0.5 versus 1.6) and days hospitalized (2.5 versus 7.3 days) were reported for rifaximin treatment versus lactulose treatment (p<0.001), and hospitalization charges per patient were $14,222 compared with $56,635 during rifaximin and lactulose treatments, respectively.

With respect to HE endpoints at the end of the treatment periods, asterixis was reported for 63% (rifaximin) versus 93% (lactulose) of patients (p<0.001), and Conn scores of 3 or 4 were observed for 6% (rifaximin) versus 25% (lactulose) (p<0.001). In addition, significantly more patients had diarrhea, flatulence, and abdominal pain during lactulose therapy than during rifaximin therapy (p<0.001).

Hospitalizations and cost of therapy were analyzed in a chart review of 39 liver transplant patients who presented with HE Conn scores of 2 during the interval from January 2004 to November 2005. Twenty-four patients were treated with lactulose and 15 were treated with rifaximin Nineteen hospitalizations were reported for the lactulose group and 3 hospitalizations for the rifaximin group. The average length of stay was significantly shorter in the rifaximin group than in the lactulose group (3.5 days [range, 3-4] versus 5.0 days [range, 3 to 10] [p<0.001]). The average annual total cost of treatment (hospitalization, emergency room visit, and drug cost) per patient was $7,958 for the rifaximin group and $13,285 for the lactulose group. Although the cost of rifaximin was substantially higher than the cost of lactulose, total cost of treatment (hospitalization plus drug cost) was 1.67-fold higher in patients who were treated with lactulose.

Durability of Rifaximin Treatment Effect

Data from the second study provide information on the long-term durability of rifaximin for the protection against breakthrough overt HE episodes. Rifaximin treated subjects from the first study who were in remission at the end of the first study (6 months treatment) were followed during open-label study the second study (n=60). Time to first breakthrough HE episode is shown for the rifaximin rollover subjects (the first study plus the second study) and the first study placebo subjects in FIG. 15. The incidence of breakthrough overt HE in these rollover rifaximin subjects was compared to placebo subjects in the first study. The incidence of breakthrough HE episode for rifaximin subjects was dramatically lower than the first study placebo group (ratio of rollover rifaximin to placebo was 0.0797 after adjusting for exposure time, p<0.0001 for difference between rifaximin and placebo.

These results demonstrated that rifaximin had a durable protective effect beginning in the first study and continuing in the second study (median exposures to rifaximin were 168 days in the first study and 253 days in the second study).

Figure 13:
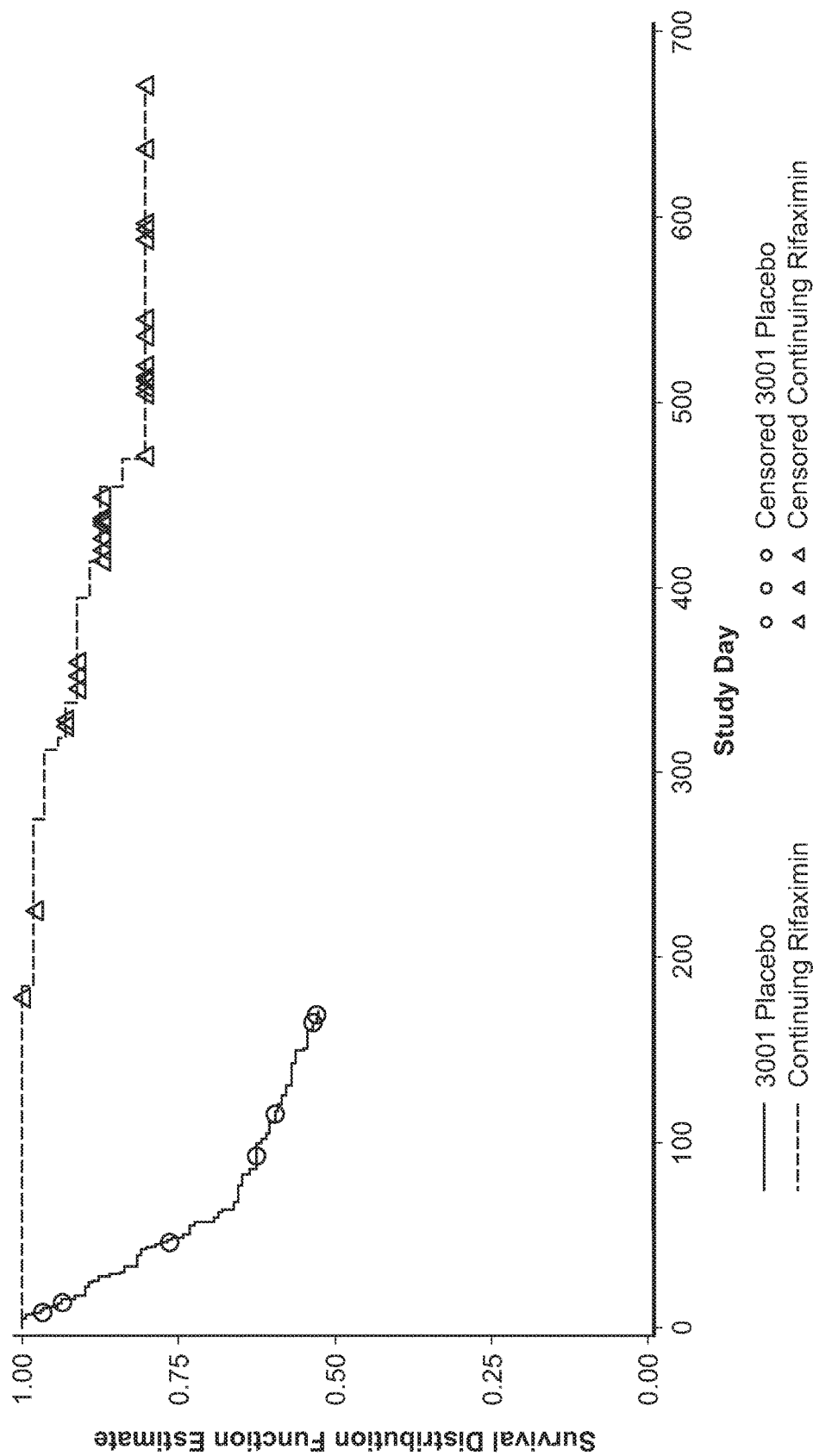
FIG. 13 depicts the Kaplan Meier estimates of distribution of time to first breakthrough HE for continuing rifaximin subjects who did not have an HE episode in the first study vs placebo.

Note for FIG. 13, the survival distribution estimate on y-axis represents the proportion of subjects without breakthrough overt HE. Dashed lines represents rifaximin treated subjects from the first study who were in remission at the end of the first study (6 months treatment) and were followed during open-label study the second study (n=60), and solid line represents the placebo group in the first study. The vertical line marks the end of the double-blind study and start of the open-label study. Open circles represent censored subjects in the first study placebo group and open triangles represent censored subjects in the continuing rifaximin group. Subjects who discontinued prior to the first breakthrough overt HE episode were censored at the time of discontinuation.

Unlike the first study, in which subjects were discontinued from the study after experiencing their first breakthrough overt HE episode, subjects had the option of continuing rifaximin therapy in the second study after experiencing breakthrough overt HE. Therefore, the incidence of breakthrough overt HE over time during rifaximin therapy was evaluated. Table 24 presents breakthrough overt HE episodes by total number of HE episodes during the course of the study.

In the all rifaximin group, 27.1% of subjects (72 of 266) had ≥1 breakthrough overt HE episode. Of the 72 subjects with breakthrough HE, most had 1 (44 subjects) or 2 (18 subjects) episodes. Ten subjects had 3 or more breakthrough HE episodes in the second study.

TABLE 24 the second study: Breakthrough Overt HE Episodes by Number of Repeat Episodes

|  | New Rifaximin N = 196 n (%) | Continuing Rifaximin N = 70 n (%) | All Rifaximin N = 266 n (%) |
|---|---|---|---|
| Subjects with ≥1 breakthrough overt HE episode | 54 (27.6) | 18 (25.7) | 72 (27.1) |
| Total number of HE episodes[a] during the study: | | | |
| 1 | 34 (17.3) | 10 (14.3) | 44 (16.5) |
| 2 | 12 (6.1) | 6 (8.6) | 18 (6.8) |
| 3 | 4 (2.0) | 0 | 4 (1.5) |
| 4 | 1 (0.5) | 1 (1.4) | 2 (0.8) |
| 5 | 1 (0.5) | 0 | 1 (0.4) |
| 6 | 0 | 1 (1.4) | 1 (0.4) |
| 10 | 2 (1.0) | 0 | 2 (0.8) |

Abbreviation: HE = hepatic encephalopathy
[a]Number of HE episodes. Subjects were counted only once for each number of overt HE episodes. For example, if a subject experienced 3 episodes, he/she was included in the row showing 3 episodes only, and was not also counted in the rows for 2 and 1 episodes.

Effect of Rifaximin on the Incidence of Overt HE Episodes (HE burden)

The effect of rifaximin therapy on the incidence of overt HE episodes (e.g., burden of HE), the numbers of HE episodes in the first study or the second study were compared to the numbers of HE episodes in the absence of rifaximin therapy. The 6-month interval prior to the first study or the 12-month interval prior to the second study was compared against rifaximin therapy in either study. The time of participation in the first study did not reflect experience in the absence of rifaximin therapy, therefore, for subjects who rolled over to the second study without an HE episode in the first study, the 12-month interval prior to the second study was used for comparison. Most subjects in the second study (152 of 266) were also in the first study. Overt HE episodes in the second study were combined with the first study because, unlike the first study, subjects in the second study had the option of remaining on rifaximin after experiencing their first breakthrough HE episode. The numbers of overt HE episodes experienced during the 6-month or 12-month intervals prior to the first study or prior to the second study were known. While 30.8% of subjects had >2 HE episodes during the 6-month or 12-month interval prior to rifaximin therapy, only 3.6% of subjects had >2 HE episodes during rifaximin therapy for up to 840 days (median exposure=253 days [~8 months]) in the first study plus the second study. This difference in the incidence of HE episodes while subjects were receiving rifaximin when compared to the absence of rifaximin therapy suggests a strong effect of rifaximin in relieving the burden of overt HE episodes in patients with recurrent, overt HE associated severe liver disease.

Hepatic encephalopathy is a serious, rare, complex, episodic, neuropsychiatric syndrome associated with advanced liver disease. Hepatic encephalopathy is a formidable burden on the patient, his/her family, and the healthcare system. Overt HE episodes are debilitating, render the patient incapable of self-care, and frequently result in hospitalization. Rifaximin has been granted orphan drug status for the HE indication because the disease is serious and chronically debilitating (further described in Section 1.1), and there is a low incidence of HE in the general population. Also, there is an unmet medical need for patients with HE because of limitations of the current standard of care.

Without wishing to be bound by any specific scientific theories, it is believed that the mechanism of action of rifaximin depends on the inhibition of DNA-dependent RNA polymerase of the target microorganisms, leading to the suppression of initiation of chain formation in RNA synthesis. Rifaximin has a lower rate of fecal eradication of pathogens compared with other commonly used antibacterial drugs and causes minimal alterations in gut flora suggesting that rifaximin has a different mechanism of action than other commonly used drugs in enteric bacterial infection, such as the fluoroquinolones. The antibacterial properties of rifaximin appear to result from bactericidal activity at rifaximin concentrations greater than or equal to the MIC, and from alterations in bacterial morphology and physiological functioning, which have been observed at sub-MIC concentrations.

It was unexpectedly discovered herein, that the risk of the development of antibiotic resistance is low during chronic treatment with rifaximin when compared to other systemic antibiotics such as neomycin. The low risk of antibiotic resistance during rifaximin therapy is likely due to the fact that resistance to rifaximin is not plasmid-mediated but instead requires a stable mutation in host cell DNA; therefore, dissemination of resistance and cross-resistance to other antibiotics by plasmid-based mechanisms are eliminated. Also, bacteria at sites outside of the GI tract are not exposed to appreciable selective pressure because of negligible systemic concentrations of rifaximin. Additionally, microbiological data from a study of patients with ulcerative colitis who were receiving high doses of rifaximin showed that rifaximin-resistant bacterial colonies generated during in vivo exposure to rifaximin were unstable and susceptibility returned after a brief period of treatment interruption.

Rifaximin treatment results in fewer overt HE episodes that may otherwise incapacitate the patient, may alleviate the burden on family members who are required to care for the patient, and reduces the burden of hospitalization in this patient population and the healthcare system. The following are results from the second study with respect to time to first breakthrough overt HE episode:

The protective effect was reproducible: the time to first breakthrough overt HE episode results were similar between the rifaximin group in the first study and new rifaximin subjects in the second study; and 22% and 27.6% had breakthrough overt HE in the first study rifaximin group and the second study new rifaximin group, respectively. Adjusted for exposure, rates of breakthrough HE episodes were 0.62 events/PEY in the rifaximin group from the first study compared to 0.38 events/PEY for new rifaximin subjects in the second study. These data demonstrate that protection against breakthrough overt HE in subjects who received rifaximin was consistent between the 2 studies. Additionally, when the first study placebo subjects crossed over to rifaximin therapy by entering the second study, a striking protective effect of rifaximin was observed in the comparison of Kaplan-Meier estimates of time to first breakthrough overt HE between placebo experience in the first study and rifaximin experience in the second study. The hazard ratio of rifaximin to placebo was 0.302 (95% CI:

0.166 to 0.549, p<0.0001 for between group difference in relative risk). This result represents 70% reduction in risk of experiencing breakthrough overt HE during rifaximin treatment in the second study when compared with their prior placebo experience in the first study. This reduction took place in spite of the aging and presumably progressing nature of the population with chronic liver disease.

The protective effect was durable: the Kaplan-Meier estimate of time-to-first breakthrough HE demonstrated long-term maintenance of remission from breakthrough HE when rifaximin subjects in remission after participation in the first study were followed in the second study (up to 680 days of rifaximin therapy; median exposure durations were 168 days in the first study and 253 days in the second study). The incidence of breakthrough HE episode for these rifaximin subjects relative to the first study placebo was dramatically low, an indication of fewer breakthrough HE episodes with rifaximin treatment (p<0.0001 for difference in relative risk between rifaximin and placebo).

Results for other efficacy endpoints also demonstrated statistically significant protective effects of rifaximin. In the first study, the analysis of time to first HE-related hospitalization (e.g., hospitalization directly resulting from HE or hospitalization complicated by HE) demonstrated that the reduction in risk of hospitalization due to HE was 50% in the rifaximin group, when compared with placebo, during the 6-month treatment period (p=0.0129 for between-group difference in relative risk). In the first study, the risk of HE-caused hospitalization (e.g., hospitalization directly resulting from HE only) was reduced by 56% (p=0.0064 for between-group difference in relative risk), and the risk of all-cause hospitalization was reduced by 30% in the rifaximin group compared with the placebo group (p=0.0793 for between-group difference in relative risk). In the first study, the risk of all-cause hospitalization rate was reduced by 30% in the rifaximin group when compared to placebo (p=0.0793 for between-group difference in relative risk). The all-cause hospitalization rate was 0.92 events/PEY in the rifaximin group versus 1.31 event/PEY in the placebo group.

In the second study, the low HE-caused hospitalization rate was maintained at rates consistent with those in the first study: HE-caused hospitalization rate was 0.29 event/PEY and all cause hospitalization in the second study was 0.66 event/PEY. The consistently low HE-related/HE-caused hospitalization rate in rifaximin-treated subjects in the first study and in the second study was at least partly a result of maintaining remission from demonstrated HE in subjects with end-stage liver disease.

The invention now being fully described, it will be apparent to one of ordinary skill in the art that many changes and modifications can be made thereto without departing from the spirit or scope of the appended claims.

What is claimed is:

1. A method of reducing a subject's risk of experiencing a breakthrough overt hepatic encephalopathy (HE) episode, comprising administering to the subject between about 1000 mg to about 1200 mg of rifaximin daily for a period of about 12 months or longer, wherein the subject has a Conn score of 0 or 1.

2. The method of claim 1, wherein a breakthrough overt HE episode comprises an increase in the Conn score to Grade greater than or equal to 2.

3. The method of claim 1, wherein a breakthrough overt HE episode for subjects having a Conn score of 0 comprises a Conn and Asterixis score increase of 1 grade.

4. The method of claim 1, wherein the subject has had two or more overt HE episodes within 6-months prior to the administration of rifaximin.

5. The method of claim 1, wherein the subject has a Model for End-Stage Liver Disease (MELD) score of 1 to 24.

6. The method of claim 1, wherein the subject has a MELD score of less than or equal to 10.

7. The method of claim 1, wherein the subject has a MELD score of between 11 and 18.

8. The method of claim 1, wherein the subject has a MELD score of between 19 and 24.

9. The method of claim 1, wherein the rifaximin is administered orally.

10. The method of claim 9, wherein 1100 mg of rifaximin is administered per day.

11. The method of claims 10, wherein 550 mg of rifaximin is administered twice daily.

12. The method of claim 1, further comprising administering lactulose.

13. A method of reducing a subject's risk of experiencing a breakthrough overt hepatic encephalopathy (HE) episode, comprising orally administering to the subject 550 mg rifaximin twice daily for a period of about 12 months or longer, wherein the subject has a Conn score of 0 or 1, a MELD score of 1 to 24, and has had two or more overt HE episodes within 6-months prior to the administration of rifaximin.

* * * * *